US010487172B2

(12) United States Patent
Sampson et al.

(10) Patent No.: US 10,487,172 B2
(45) Date of Patent: Nov. 26, 2019

(54) ALKENE ISOMERIZATION AS AN ENTRY TO EFFICIENT ALTERNATING RING-OPENING METATHESIS POLYMERIZATION (I-AROMP)

(71) Applicant: The Research Foundation for The State University of New York, Albany, NY (US)

(72) Inventors: Nicole S. Sampson, Setauket, NY (US); Li Tan, Centereach, NY (US); Kathlyn Parker, Centereach, NY (US)

(73) Assignee: The Research Foundation for The State University of New York, Albany, NY (US)

(*) Notice: Subject to any disclaimer, the term of this patent is extended or adjusted under 35 U.S.C. 154(b) by 35 days.

(21) Appl. No.: 15/545,580

(22) PCT Filed: Mar. 21, 2016

(86) PCT No.: PCT/US2016/023457
§ 371 (c)(1),
(2) Date: Jul. 21, 2017

(87) PCT Pub. No.: WO2016/154135
PCT Pub. Date: Sep. 29, 2016

(65) Prior Publication Data
US 2018/0002481 A1 Jan. 4, 2018

Related U.S. Application Data

(60) Provisional application No. 62/136,436, filed on Mar. 20, 2015.

(51) Int. Cl.
*C08G 61/08* (2006.01)
*B01J 31/22* (2006.01)
(Continued)

(52) U.S. Cl.
CPC .......... *C08G 61/08* (2013.01); *B01J 31/2265* (2013.01); *C07C 13/06* (2013.01); *C07C 13/18* (2013.01);
(Continued)

(58) Field of Classification Search
CPC .... C08F 232/00; C08F 232/02; C08F 232/04; C08F 232/08; C08F 4/70; C08G 61/08
See application file for complete search history.

(56) References Cited

U.S. PATENT DOCUMENTS 8,232,360 B2 * 7/2012 Sampson ............... A61K 51/06
526/171
8,795,647 B2 * 8/2014 Sampson ............... A61K 47/58
424/78.08
(Continued)

FOREIGN PATENT DOCUMENTS

WO WO 2010/022284 A1 * 2/2010 .............. C08F 4/44
WO 2015/013317 A1 1/2015

OTHER PUBLICATIONS

Song, A.; Parker, K.A.; Sampson, N.S. J. Am. Chem. Soc. 2009, 131, 3444-3445. (Year: 2009).*
(Continued)

*Primary Examiner* — Rip A Lee
(74) *Attorney, Agent, or Firm* — Fox Rothschild LLP

(57) ABSTRACT

This invention relates to the field of polymers and olefin polymerization, and more specifically olefin metathesis polymerization. Specifically, the present invention provides a polymer comprising rigorously alternating AB subunits and methods of formation of the AB alternating polymers. In the polymers and process of the invention, the A monomer is derived from a cyclobutene derivative, and the B mono-
(Continued)

$^1$H NMR spectra of amides 1c (top) and 1c' (bottom) in CDCl$_3$.

mer is derived from a cyclohexene derivative. The polymerization takes place in the presence of an olefin metathesis catalyst.

13 Claims, 58 Drawing Sheets

(51) Int. Cl.
  *C07C 13/06* (2006.01)
  *C07C 13/18* (2006.01)
  *C07C 13/32* (2006.01)
  *C08F 232/04* (2006.01)
  *C09D 165/00* (2006.01)
(52) U.S. Cl.
  CPC ............ *C07C 13/32* (2013.01); *C08F 232/04* (2013.01); *C09D 165/00* (2013.01); *C08G 2261/124* (2013.01); *C08G 2261/1426* (2013.01); *C08G 2261/3323* (2013.01); *C08G 2261/3325* (2013.01); *C08G 2261/418* (2013.01)

(56) References Cited

U.S. PATENT DOCUMENTS

| | | | |
|---|---|---|---|
| 9,624,338 B2 * | 4/2017 | Sampson | ............... A61K 31/74 |
| 2003/0236377 A1 | 12/2003 | Choi et al. | |
| 2011/0212046 A1 | 9/2011 | Sampson et al. | |

OTHER PUBLICATIONS

Tan, L.; Parker, K.A.; Sampson, N.S. Macromolecules 2014, 47, 6572-6579. (Year: 2014).*
Tan, L.; Li, G.; Parker, K.A.; Sampson, N.S. Macromolecules 2015, 48, 4793-4800. (Year: 2015).*
Romulus, J.; Tan, L.; Weck, M.; Sampson, N.S. ACS Macro Lett. 2013, 2, 749-752. (Year: 2013).*
Song, A. et al., "Synthesis of Copolymers by Alternating ROMP (AROMP)"; J. Am. Chem. Soc. (2009); vol. 131:10; pp. 3444-3445.
Song, A. et al., "Scope of the Ring Opening Metathesis Polymerization (ROMP) Reaction of 1-Substituted Cyclobutenes"; J. Am. Chem. Soc. (2010); vol. 132:30; pp. 10513-10520.
Tan, L. et al., "A Bicyclo[4.2.0]octene-Derived Monomer Provides Completely Linear Alternating Copolymers via Alternating Ring-Opeining Metathesis Polymerization (AROMP)"; Macromolecules (2014); vol. 47; pp. 6572-6579.

* cited by examiner

HSQC spectrum of amide 1e' in CDCl₃.

Fig. 4

Partial $^{13}$C NMR spectra of AROMP polymers illustrate the absence of AA dyad or BB dyad $^{13}$C resonances.

$^1$H NMR spectra of poly(1d'-alt-3)$_n$ with (bottom) and without (top) deuterium labeling in CD$_2$Cl$_2$.

Fig. 9. $^{13}$C NMR spectrum of amide 1a in CDCl$_3$.

Fig. 12 $^{13}$C NMR spectrum of amide 1b in CDCl$_3$.

Fig. 14. $^{13}$C NMR spectrum of amide 1c in CDCl$_3$.

Partial 13C NMR spectrum of amide 1e in CDCl3.

Fig. 21. $^{13}$C NMR spectrum of amide 1f in CDCl$_3$.

Fig. 23. $^{13}$C NMR spectrum of amide 1f* in CDCl$_3$.

Fig. 25. $^{13}$C NMR spectrum of amide 4 in CDCl$_3$.

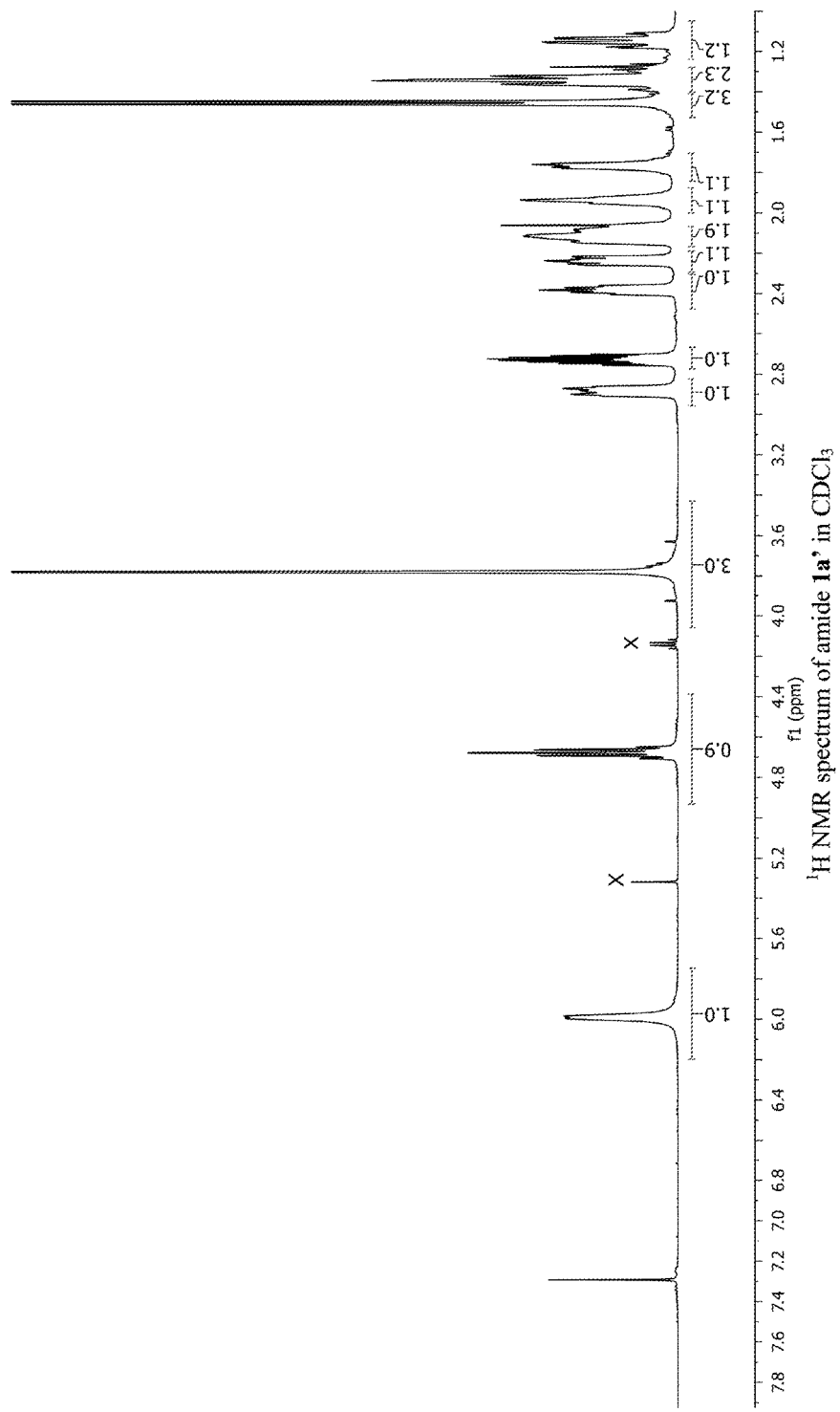
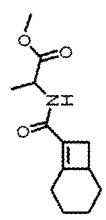
Fig. 27
$^1$H NMR spectrum of amide 1a' in CDCl$_3$

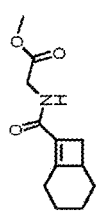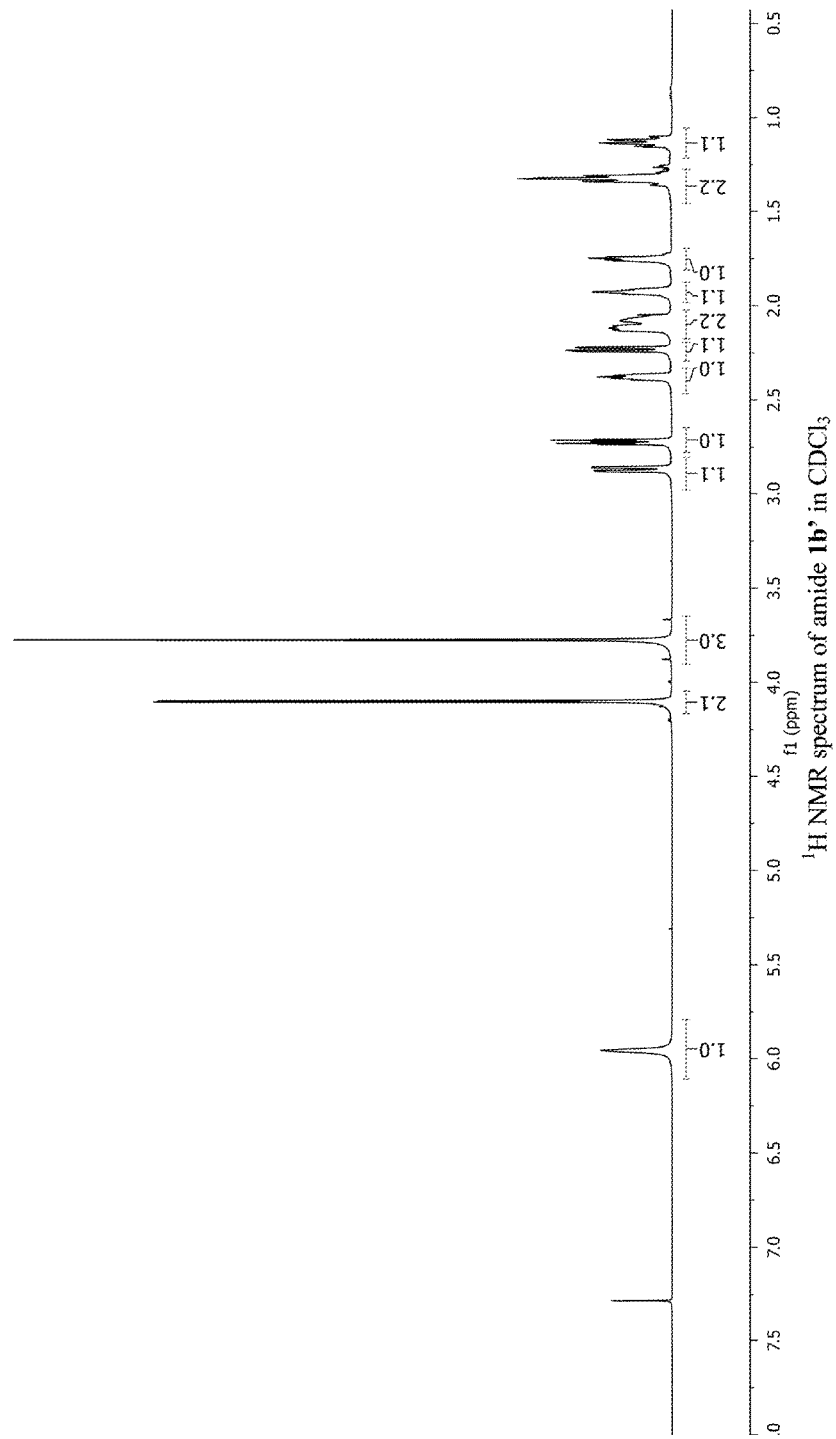
Fig. 28

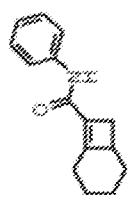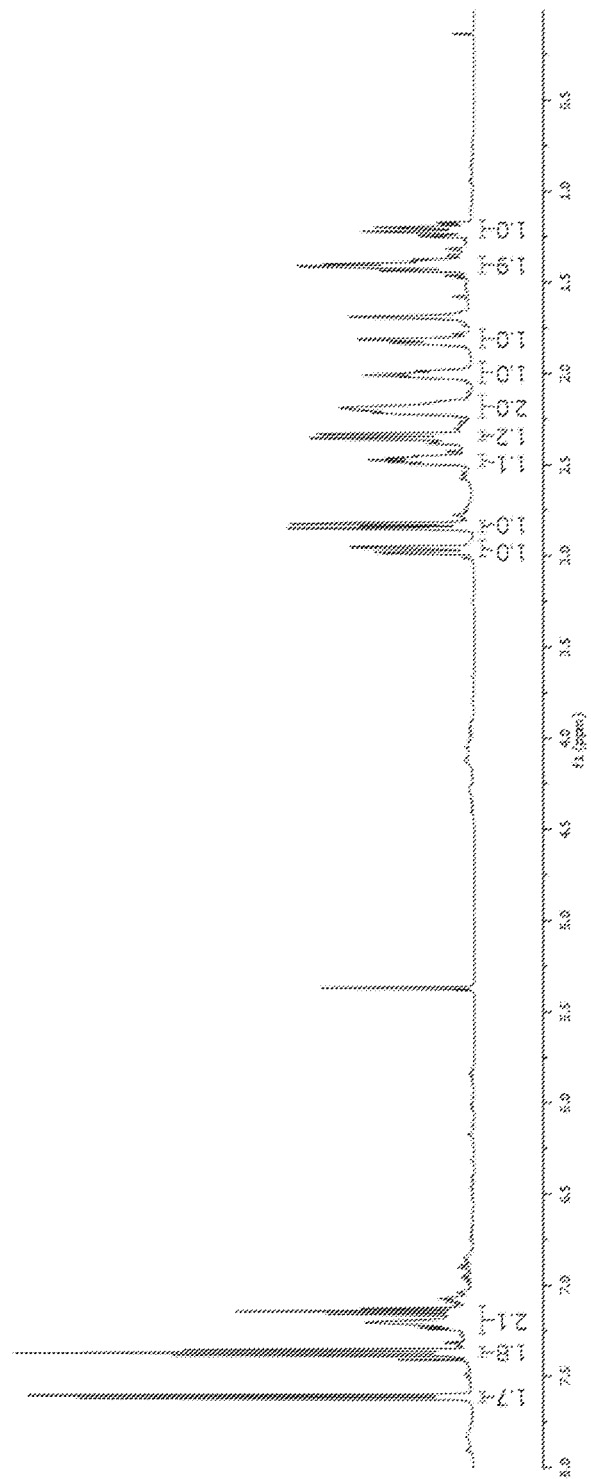
Fig. 32 $^1$H NMR spectrum of crude amide 1d and alkylidene 2 in $CD_2Cl_2$ with 100% 1d isomerized to 1d'.

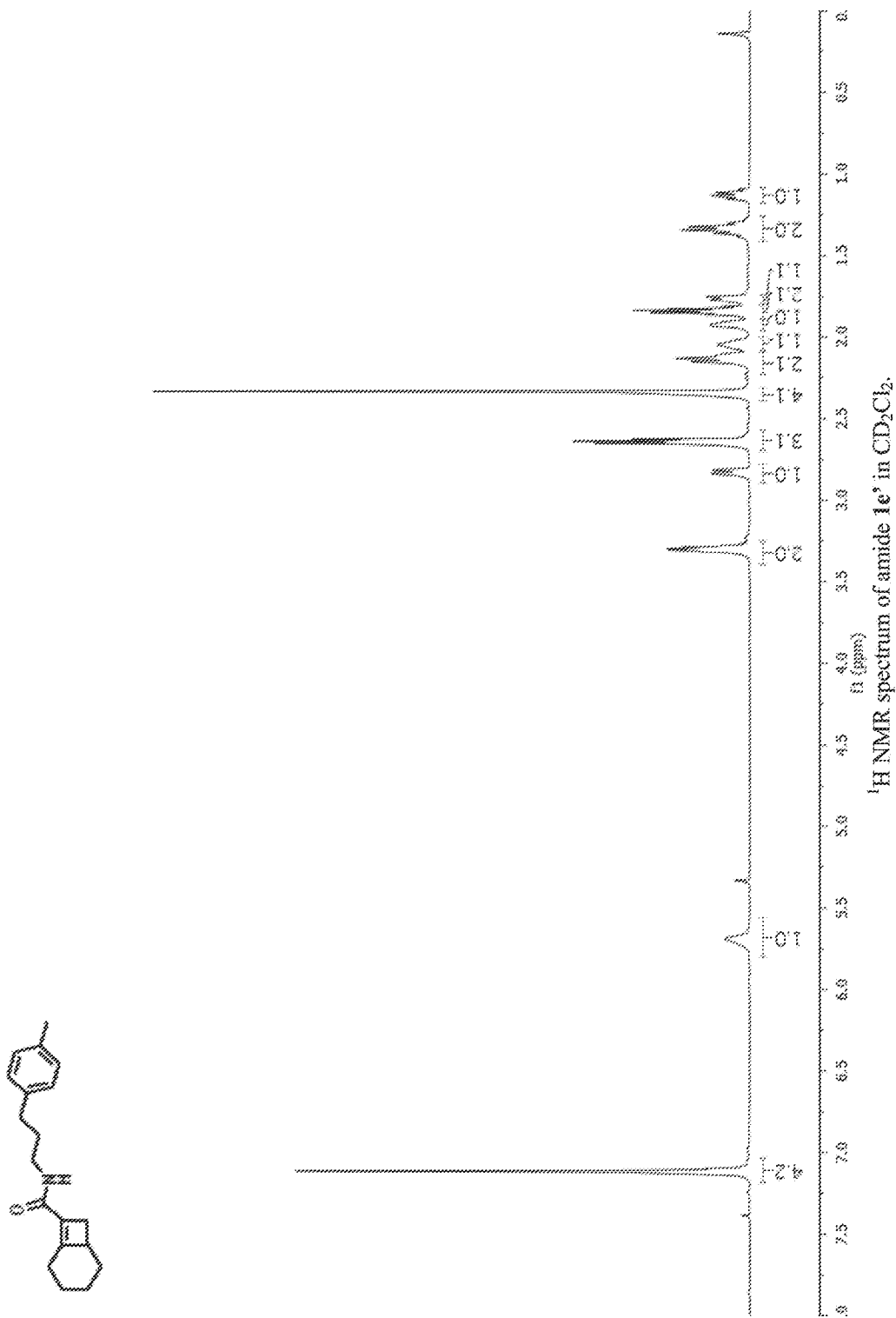

$^1$H NMR spectrum of amide 1f and alkylidene 2 in $CD_2Cl_2$ with 90% 1f isomerized to 1f'.

$^1$H NMR spectrum of amide 4 and alkylidene 2 in CD$_2$Cl$_2$. No isomerization is observed.

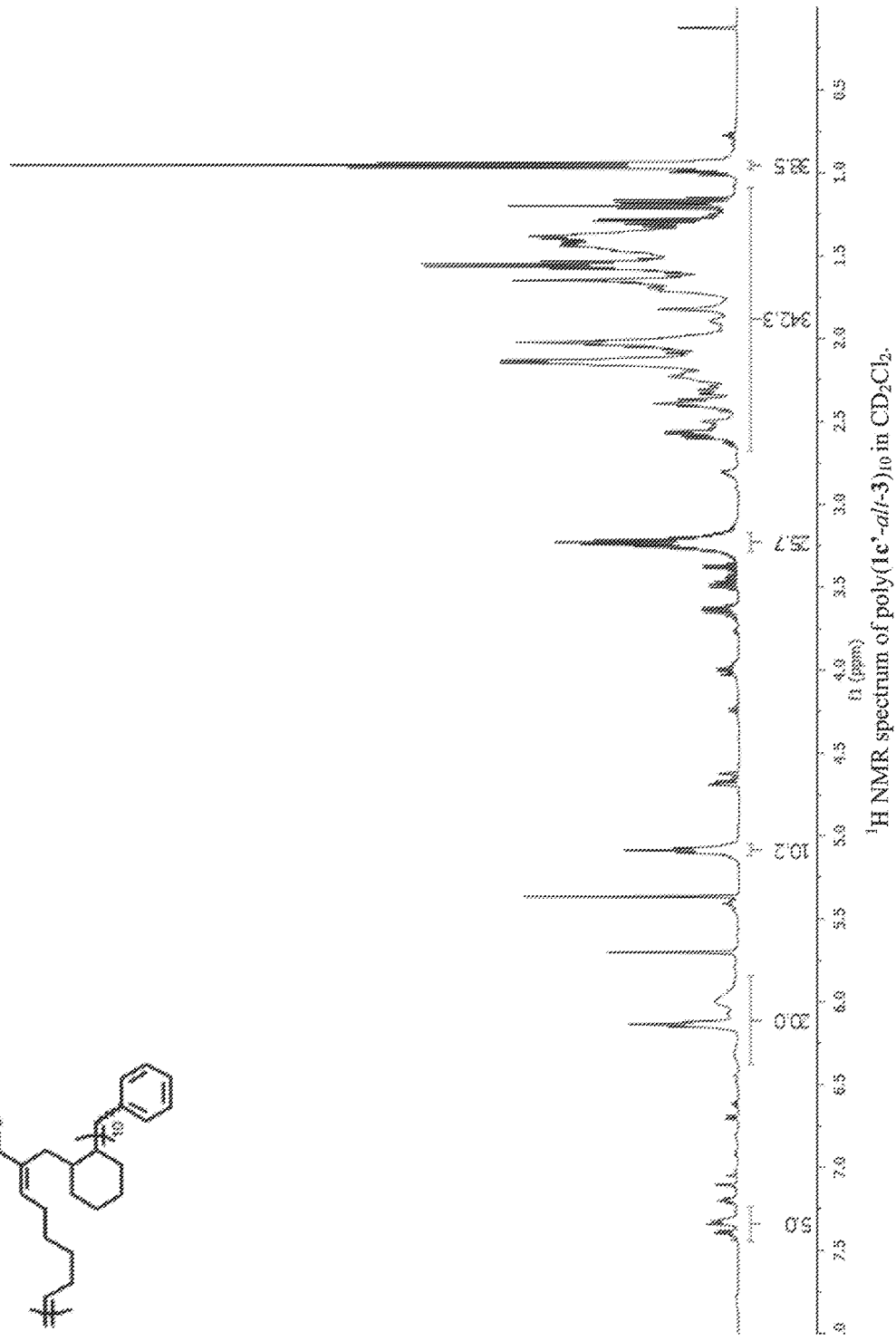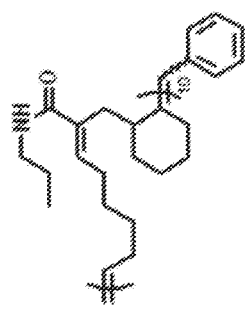
Fig. 40

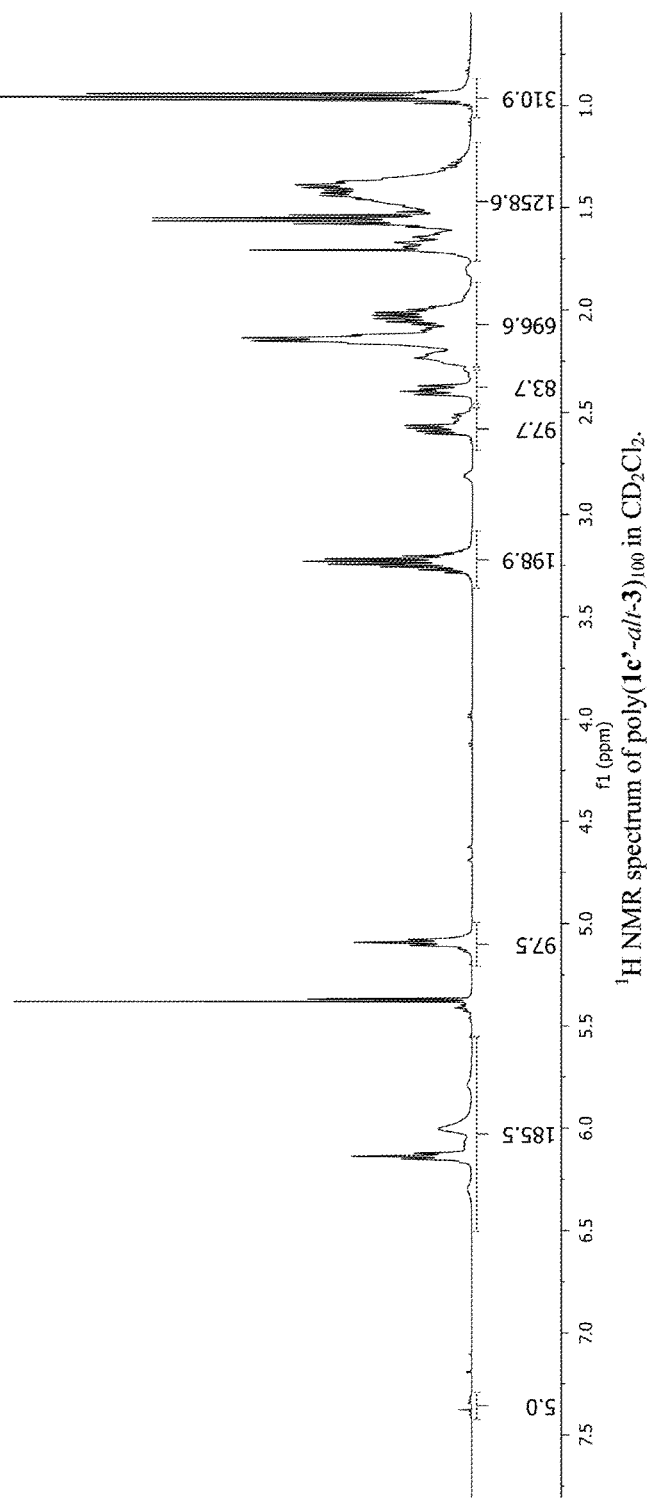
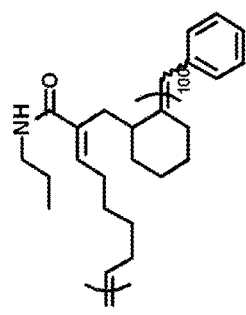
Fig. 42
$^1$H NMR spectrum of poly(1c'-*alt*-3)$_{100}$ in CD$_2$Cl$_2$.

Fig. 45. $^1$H NMR spectrum of poly(1b'-*alt*-3)$_{140}$ in CD$_2$Cl$_2$.

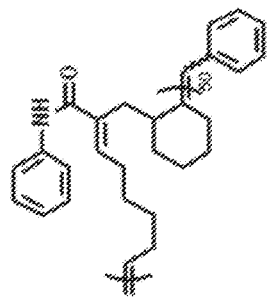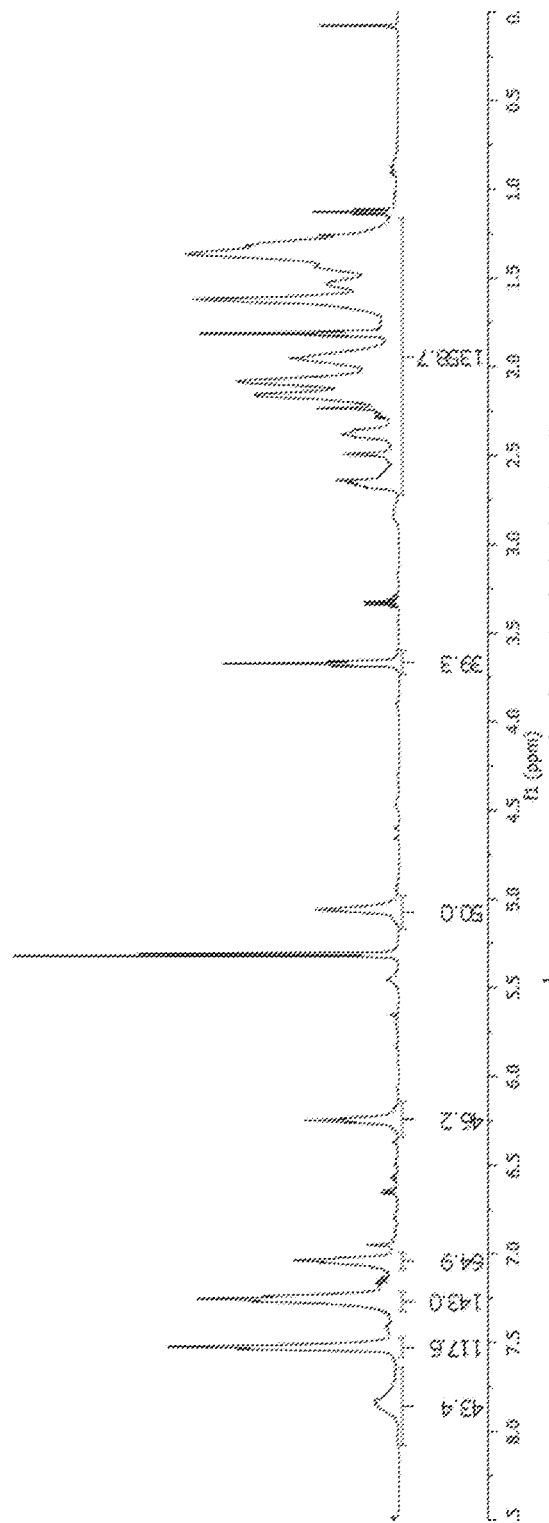
Fig. 52

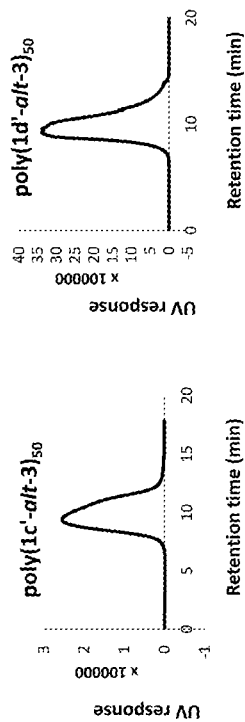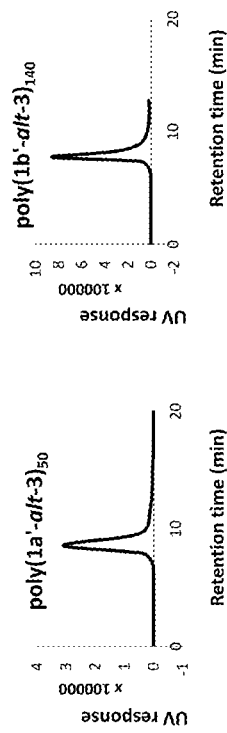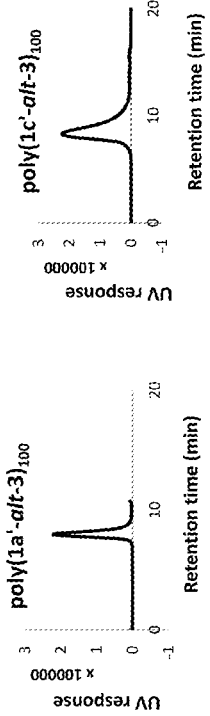
Fig. 55

ALKENE ISOMERIZATION AS AN ENTRY TO EFFICIENT ALTERNATING RING-OPENING METATHESIS POLYMERIZATION (I-AROMP)

CROSS REFERENCE TO RELATED APPLICATIONS

This application is a 371 of PCT/US2016/023457 which claims the benefit of priority to U.S. Application No. 62/136,436, filed Mar. 20, 2015, each of which is incorporated herein by reference in its entirety.

STATEMENT OF GOVERNMENT INTEREST

This invention was made with government support under GM097971, GM074776, and HD038519 awarded by the National Institutes of Health. The government has certain rights in the invention.

FIELD OF THE INVENTION

This invention relates to the field of polymers and olefin polymerization, and more specifically olefin metathesis polymerization. Specifically, the present invention provides a polymer comprising rigorously alternating AB subunits and methods of formation of the AB alternating polymers.

BACKGROUND

Copolymers are employed in a wide range of materials, ranging from bulk plastics to specialized coatings, pharmaceutical compositions, and biomedical and electronic devices. Among the most commonly used are block copolymers, which often rely on phase separation of the two blocks for their functional properties, for example in drug delivery nanoparticles, and random copolymers, which incorporate two or more functional moieties that act co-operatively, for example in organic light emitting diodes. Regularly alternating polymers allow for controlled positioning of functional substituents, but they are difficult to access synthetically.

Regioregular alternating polymers (for example, SAN, styrene-acrylonitrile, an alternating copolymer used in plastics) are generally synthesized by radical polymerization with kinetic control of alternation in the polymerization reaction. (Hawker, C. J.; Bosman, A. W.; Harth, E. *Chemical Reviews* 2001, 101, 3661-3688; Matyjaszewski, K.; Xia, J. H. *Chemical Reviews* 2001, 101, 2921-2990). Recently, ring opening metathesis polymerization (ROMP) and ring opening insertion metathesis polymerization (ROIMP) have been employed to synthesize alternating polymers: Ilker, M. F.; Coughlin, E. B. *Macromolecules* 2002, 35, 54-58; Choi, T. L.; Rutenberg, I. M.; Grubbs, R. H. *Angewandte Chemie-Intl. Ed.* 2002, 41, 3839-3841; PCT publication WO 03/070779.

The existing methods of formation of alternating polymers are limited, and there remains a need for new and more structurally diverse substrates and polymers. The present invention provides substrate and catalyst combinations that can generate a wider range of alternating polymers, having a range of diverse properties.

BRIEF DESCRIPTION OF THE INVENTION

The invention provides an AB copolymer and a method for producing an alternating AB copolymer comprising the repeating unit I,

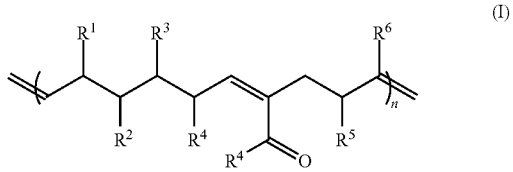

in which the A monomer is derived from a cyclobutene derivative III or III', and the B monomer is derived from a cyclohexene derivative II.

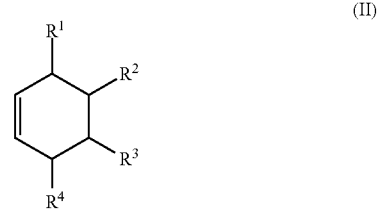

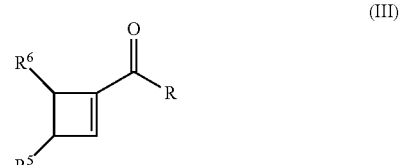

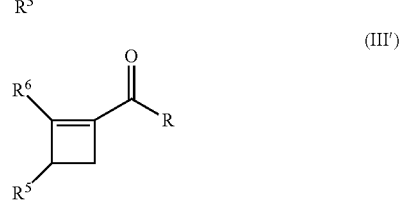

In embodiments starting from cyclobutene III, in a first step the cyclobutene III is isomerized to III' in the presence of an olefin metathesis catalyst.

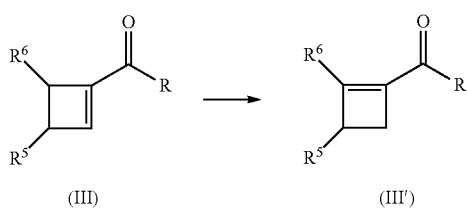

The method comprises isomerizing the cyclobutene 1-carboxyl or 1-carbonyl derivative III to isomerized cyclobutene 1-carboxyl or 1-carbonyl derivative III' in the presence of an olefin metathesis catalyst. The method further comprises contacting the cyclohexene derivative II with the isomerized cyclobutene 1-carboxyl or 1-carbonyl derivative III' in the presence of an olefin metathesis catalyst. In certain embodiments of the invention, the cyclobutene III' is prepared separately and treated with the cyclohexene II in the presence of an olefin metathesis catalyst to provide the polymer I. These polymerization methods enable the facile preparation of amphiphilic and bifunctional alternating polymers from simple and readily available starting materials.

BRIEF DESCRIPTION OF THE FIGURES

FIG. 4 shows the kinetic $^{13}$C NMR spectra of 1e isomerization in the presence of catalyst 2 (1:1 ratio) in CD$_2$Cl$_2$; (a) 70-90 min after mixing, (b) from bottom to top, spectra were obtained at 0-20 min, 40-55 min, 70-90 min, and 110-130 min.

FIG. 27 shows the $^1$H NMR spectrum of amide 1a' in CDCl$_3$.

FIG. 28 shows the $^1$H NMR spectrum of amide 1b' in CDCl$_3$.

FIG. 32 shows the $^1$H NMR spectrum of crude amide 1d and alkylidene 2 in CD$_2$Cl$_2$ with 100% 1d isomerized to 1d'.

FIG. 33 shows the $^1$H NMR spectrum of amide 1e' in CD$_2$Cl$_2$.

FIG. 40 shows the $^1$H NMR spectrum of poly(1c'-alt-3)$_{10}$ in CD$_2$Cl$_2$.

FIG. 42 shows the $^1$H NMR spectrum of poly(1c'-alt-3)$_{100}$ in CD$_2$Cl$_2$.

FIG. 52 shows the $^1$H NMR spectrum of poly(1d'-alt-3)$_{50}$ in CD$_2$Cl$_2$.

FIG. 55 shows the molar mass dispersity ($Ð_M$) traces of isomerized amide AROMP polymers. Phenogel 5 µm MXL LC column (300×7.8 mm, 100 KDa exclusion limit), Phenomenex, was used with a flow rate of 0.7 mL/min in methylene chloride at 30° C. 50-mers of 1c' and 1d' were prepared in a one-pot procedure from 1c or 1d. All others were prepared with isomerized and purified amides.

DETAILED DESCRIPTION OF THE INVENTION

Figure 1:
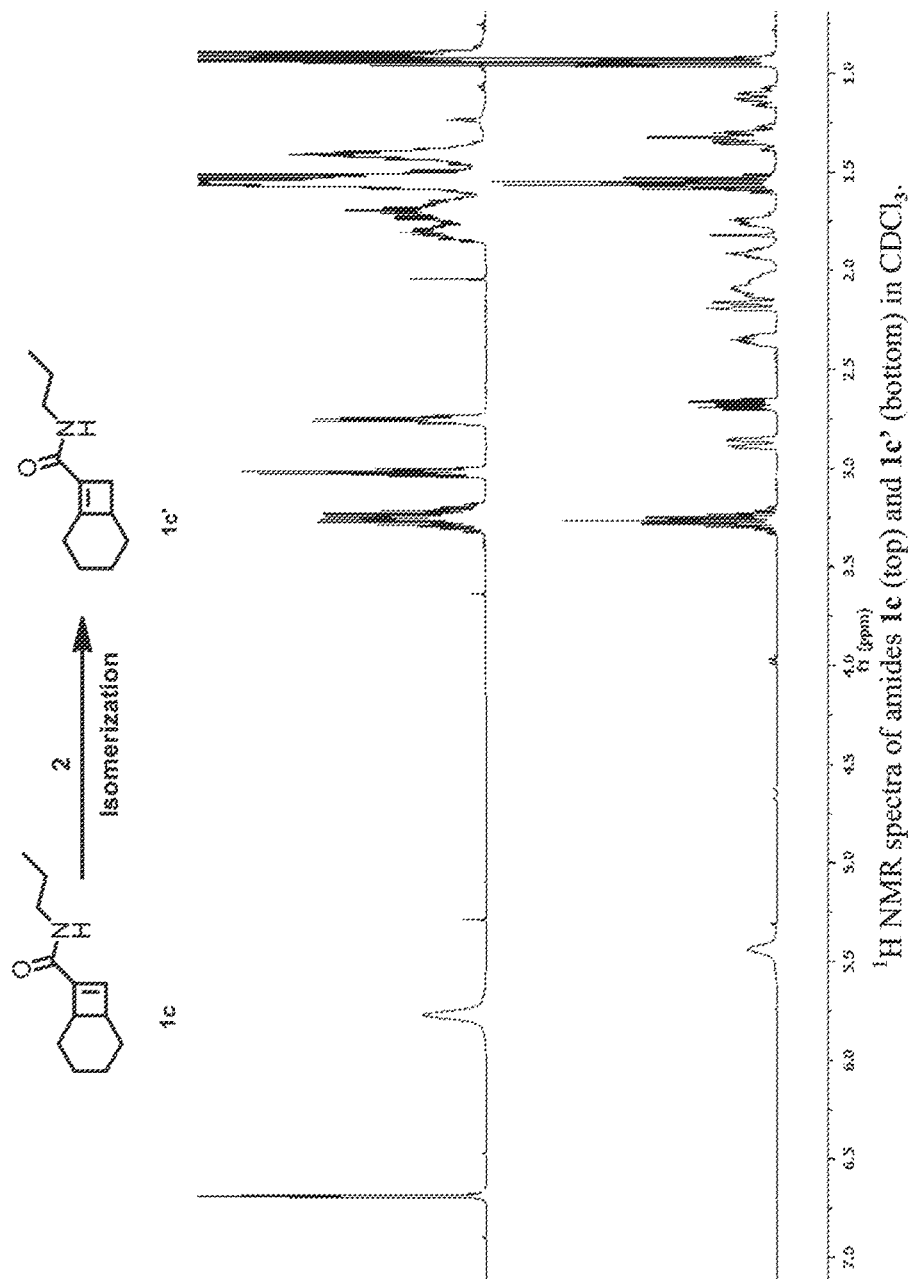
FIG. 1 shows the $^1$H NMR spectra of amides 1c (top) and 1c' (bottom) in CDCl$_3$.

Most sequence-controlled polymers lack rigorous fidelity, e.g. the chain microstructures are not completely well controlled or they are homo polymers with simple chain microstructures or copolymers, such as random or block copolymers, in which the monomer sequence is not precisely controlled. Polymers of imprecise sequence are widely employed, but do not provide the same structural and functional complexity as sequence-controlled biopolymers created by nature. The present method provides a facile approach to prepare long and alternating AB copolymers. According to the present method, these copolymers may be formed in a single reaction mixture in which isomerization occurs first, followed by alternating ring-opening cross metathesis of type A monomer and ring opening cross metathesis of type B monomer.

Accordingly, the invention provides methods for the preparation of polymers in which the backbone chain has a regular alternating pattern of functional group arrangement. The method further allows for the preparation of copolymers having low polydispersities and long lengths.

The invention provides an alternating AB copolymer and a method for producing an alternating AB copolymer comprising the repeating unit I,

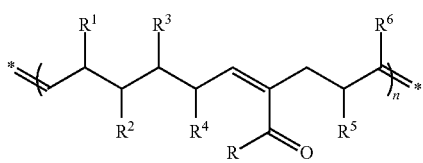
(I)

The method comprises the polymerization of cyclobutene derivative III' and cyclohexene derivative II in the presence of an olefin metathesis catalyst. In embodiments of the process that use the cyclobutene III, the process further comprises isomerizing a cyclobutene of structure III in the presence of an olefin metathesis catalyst to form a cyclobutene III' and contacting an olefin of structure II with an isomerized cyclobutene III'

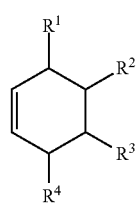
(II)

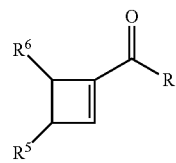
(III)

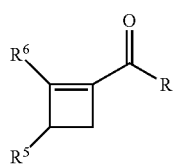
(III')

in the presence of an olefin metathesis catalyst.

In the above structures: R may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, NO₂, oxo, amino, alkyl, cycloalkyl, alkenyl, alkynyl, aralkyl, aryl, and a heterocyclic group. In certain embodiments, the repeating unit, n, is between 2 and 500. Each substituent $R^1$ through $R^6$ may independently be selected from, but is not limited to, H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen. It is understood that any carbon-carbon double bonds in $R^a$ or in $R^1$ through $R^6$ are essentially unreactive toward metathesis reactions with the catalyst. It will be also understood that adjacent substitutions of $R^1$-$R^6$ may be taken together to form a 5- to 7-membered ring which may be optionally substituted with up to three substituents selected from halo, CN, NO₂, oxo, amino, alkyl, cycloalkyl, alkenyl, alkynyl, aralkyl, aryl, and a heterocyclic group.

In preferred embodiments of the invention, $R^5$ and $R^6$ are taken together to form a 5- or 6-membered ring, which may optionally contain up to 2 heteroatoms in the ring selected from O or N, and which may be unsubstituted or substituted with up to four substituents selected from halo, CN, NO₂, oxo, amino, alkyl, cycloalkyl, alkenyl, alkynyl, aralkyl, aryl, and a heterocyclic group. In particularly preferred embodiments, $R^5$ and $R^6$ are taken together to form a cyclohexyl ring, which may be optionally substituted.

In certain embodiments, the invention provides a method for producing an alternating AB copolymer comprising the repeating unit Ia

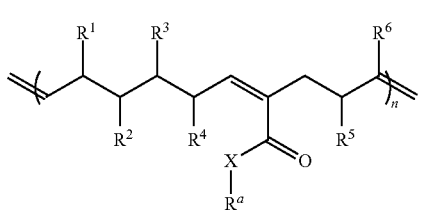
(Ia)

In the above structures, X may be either O or NH, and is preferably NH; and $R^a$ may be, but is not limited to, H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, amino, alkyl, cycloalkyl, alkenyl, alkynyl, aralkyl, aryl, and a heterocyclic group. In certain embodiments, the repeating unit, n, is between 2 and 500. Each substituent $R^1$ through $R^6$ may independently be, but is not limited to, H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen. It is understood that any carbon-carbon double bonds in $R^a$ or in $R^1$ through $R^6$ are essentially unreactive toward metathesis reactions with the catalyst. It will be also understood that adjacent substitutions of $R^1$-$R^6$ may be taken together to form a 5- to 7-membered ring which may be optionally substituted with up to three substituents selected from halo, CN, $NO_2$, oxo, amino, alkyl, cycloalkyl, alkenyl, alkynyl, aralkyl, aryl, and a heterocyclic group.

In preferred embodiments of the invention, $R^5$ and $R^6$ are taken together to form a 5- or 6-membered ring, which may optionally contain up to 2 heteroatoms in the ring selected from O or N, and which may be unsubstituted or substituted with up to four substituents selected from halo, CN, $NO_2$, oxo, amino, alkyl, cycloalkyl, alkenyl, alkynyl, aralkyl, aryl, and a heterocyclic group. In particularly preferred embodiments, $R^5$ and $R^6$ are taken together to form a cyclohexyl ring, which may be optionally substituted.

In a preferred embodiment, the invention provides a method for producing an alternating AB copolymer comprising the repeating unit Ib

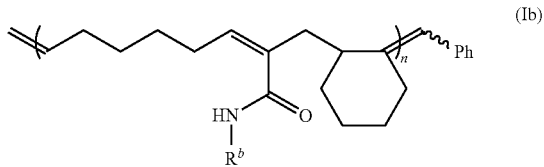
(Ib)

In the above structure, $R^b$ may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, amino, alkyl, cycloalkyl, alkenyl, alkynyl, aralkyl, aryl, and a heterocyclic group, with the proviso that any carbon-carbon double bonds in $R^b$ are essentially unreactive toward metathesis reactions with the catalyst. In certain embodiments, the repeating unit, n, is between 2 and 500.

In certain embodiments, the invention provides a method for producing an alternating AB copolymer from a monomer comprising a cyclohexene of structure IIa

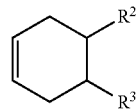
(IIa)

In the above structures, each substituent $R^2$ and $R^3$ may independently be, but is not limited to, H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, arylamino or halogen, and may be optionally substituted with up to three substituents selected from halo, CN, $NO_2$, oxo, amino, alkyl, cycloalkyl, alkenyl, alkynyl, aralkyl, aryl, and a heterocyclic group; with the proviso that any carbon-carbon double bonds in $R^2$ and $R^3$ are essentially unreactive toward metathesis reactions with the catalyst. It will be also understood that $R^2$ and $R^3$ may be taken together to form a 5- to 7-membered ring which may be optionally substituted with up to three substituents selected from halo, CN, $NO_2$, oxo, amino, alkyl, cycloalkyl, alkenyl, alkynyl, aralkyl, aryl, and a heterocyclic group.

In a preferred embodiment, the invention provides a method for producing an alternating AB copolymer from a monomer comprising a cyclohexene of structure

In certain embodiments, the invention provides a method for producing an alternating AB copolymer from a monomer comprising an cyclobutene of structure IIIa or IIIa', in which the cyclobutene of structure IIIa is isomerized to a cyclobutene of structure IIIa'

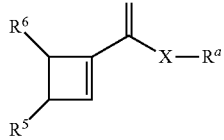
(IIIa)

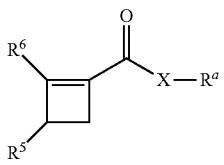
(IIIa')

in the presence of an olefin metathesis catalyst.

In the above structures, X may be either O, or NH, and $R^a$ may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, alkyl, cycloalkyl, alkenyl, alkynyl, aralkyl, aryl, and a heterocyclic group. Each substituent $R^5$ and $R^6$ may independently be, but is not limited to, H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen. It is understood that any carbon-carbon double bonds in $R^a$, $R^5$ or $R^6$ are essentially unreactive toward metathesis reactions with the catalyst. It will be also understood that $R^5$ and $R^6$ may be taken together to form a 5- to 7-membered ring which may be optionally substituted with up to three substituents selected from halo, CN, $NO_2$, oxo, amino, alkyl, cycloalkyl, alkenyl, alkynyl, aralkyl, aryl, and a heterocyclic group.

In certain embodiments, the invention provides a method for producing an alternating AB copolymer from a monomer comprising an cyclobutene of structure IIIb or IIIb', in which the cyclobutene of structure IIIb is isomerized to a cyclobutene of structure IIIb'

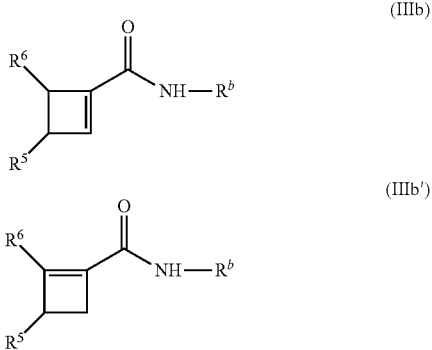

in the presence of an olefin metathesis catalyst.

In the above structures, $R^b$ may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, amino, alkyl, cycloalkyl, alkenyl, alkynyl, aralkyl, aryl, and a heterocyclic group. Each substituent $R^5$ and $R^6$ may independently be, but is not limited to, H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen. It is understood that any carbon-carbon double bonds in $R^a$, $R^5$ or $R^6$ are essentially unreactive toward metathesis reactions with the catalyst. It will be also understood that $R^5$ and $R^6$ may be taken together to form a 5- to 7-membered ring which may be optionally substituted with up to three substituents selected from halo, CN, $NO_2$, oxo, amino, alkyl, cycloalkyl, alkenyl, alkynyl, aralkyl, aryl, and a heterocyclic group.

In preferred embodiments of the invention, for each of IIIa, IIIa', IIIb, IIIb', $R^5$ and $R^6$ are taken together to form a 5- or 6-membered ring, which may optionally contain up to 2 heteroatoms in the ring selected from O or N, and which may be unsubstituted or substituted with up to four substituents selected from halo, CN, $NO_2$, oxo, amino, alkyl, cycloalkyl, alkenyl, alkynyl, aralkyl, aryl, and a heterocyclic group. In particularly preferred embodiments, $R^5$ and $R^6$ are taken together to form a cyclohexyl ring, which may be optionally substituted.

In a preferred embodiment, the invention provides a method for producing an alternating AB copolymer from a monomer comprising an cyclobutene of structure IIIc or IIIc', in which the cyclobutene of structure IIIc is isomerized to a cyclobutene of structure IIIc'

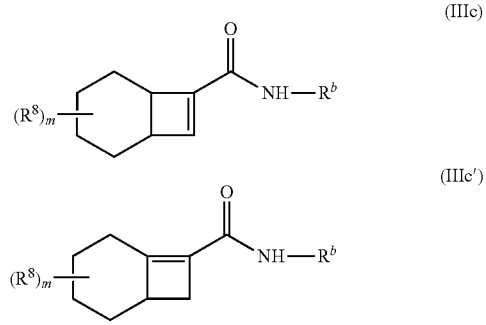

in the presence of an olefin metathesis catalyst.

In the above structures, $R^b$ may be, but is not limited to, H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_1$-$C_{20}$ alkenyloxy, $C_3$-$C_6$ cycloalkyloxy, aryloxy, heterocyclyloxy, $C_1$-$C_{20}$ alkylamino, $C_1$-$C_{20}$ alkenylamino, $C_3$-$C_8$ cycloalkylamino, heterocyclylamino, or arylamino and may be optionally substituted with up to three substituents selected from halo, CN, $NO_2$, oxo, amino, alkyl, cycloalkyl, alkenyl, alkynyl, aralkyl, aryl, and a heterocyclic group. It will be understood that m may be between 0 and 4, and that for each m, the substituent $R^8$ may independently be, but is not limited to, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen. It is understood that any carbon-carbon double bonds in $R^b$ or $R^8$ are essentially unreactive toward metathesis reactions with the catalyst. It will be also understood that adjacent substitutions of $R^8$ may be taken together to form a 5- to 7-membered ring which may be optionally substituted with up to three substituents selected from halo, CN, $NO_2$, oxo, amino, alkyl, cycloalkyl, alkenyl, alkynyl, aralkyl, aryl, and a heterocyclic group.

By way of example, suitable cyclohexene and cyclobutene species include but are not limited to the following:

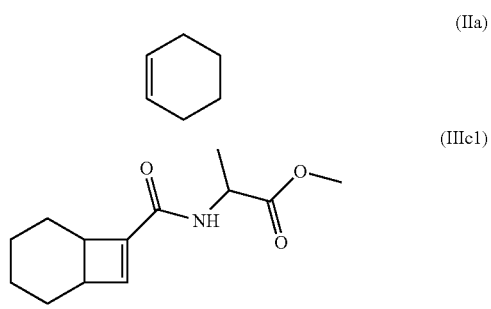

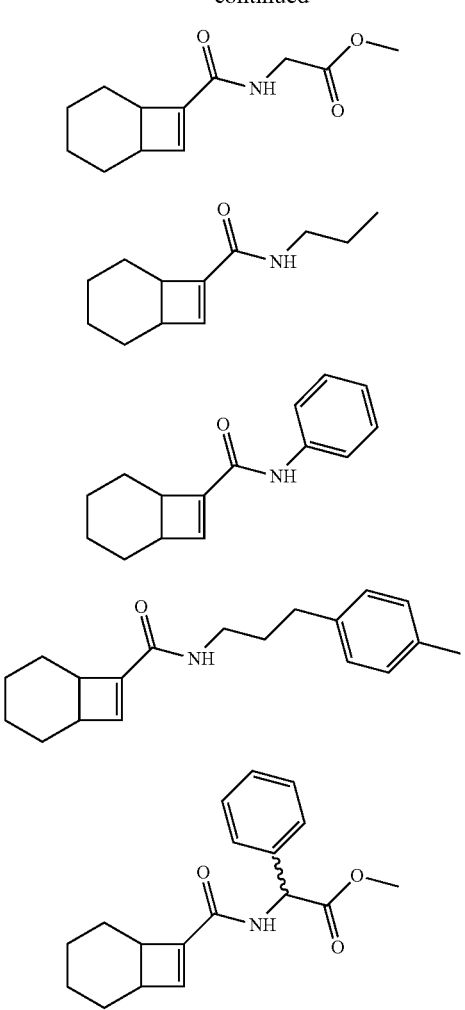

(IIIc2)
(IIIc3)
(IIIc4)
(IIIc5)
(IIIc6)

It will be understood that any olefins or other functional groups in the substituents of the A and B monomers should be essentially unreactive with the metathesis catalyst under the reaction conditions, so that the metathesis polymerization involves the cyclobutene and cyclohexene double bonds exclusively, or nearly so. Generally, any carbon-carbon double bonds in R or in $R^1$ through $R^6$ should be trisubstituted or tetrasubstituted, or otherwise rendered unreactive with the catalyst.

Aryl, as used herein, includes but is not limited to optionally substituted phenyl, naphthyl, anthracenyl, and phenanthryl groups. Heterocycle and heterocyclyl refer to monocyclic and fused polycyclic heteroaromatic and heteroaliphatic ring systems containing at least one N, O, S, or P atom. Aryl and heterocyclic groups may contain from 1 to 60 carbon atoms, and may range from furan, thiophene, and benzene to large chromophores such as phthalocyanines and fullerenes. For some applications, aryl and heterocyclic groups will preferably contain from 1 to 20 carbon atoms.

It will be apparent that alkyl, alkenyl, cycloalkyl, heterocyclyl, acyl, and aryl moieties in the substituents R and $R^1$ through $R^6$ may be substituted with functional groups known to be compatible with the catalyst. Examples include, but are not limited to, $C_1$-$C_4$ acyl, acyloxy, acylamino, amido, aryloxy, alkoxy and alkylthio groups; halogens; protected amino groups such as BocNH— and FmocNH—; protected hydroxy groups such as TMSO—, BzO—, and BnO—; and protected carboxyl groups such as —$CO_2$-t-Bu and —$CO_2$Bn. Accordingly, the terms alkyl, alkenyl, cycloalkyl, acyl, aryl, and heterocyclyl as used herein encompass such substituents.

The method may be used to prepare rigorously alternating AB copolymers. In the copolymers of the present invention, an A monomer derived from a cyclobutene derivative III selected from a compound of formula III, IIIa, IIIb and IIIc alternates with a B monomer selected from a cyclohexene derivative II or IIa. In certain embodiments of the invention, the cyclobutene III is isomerized to provide the cyclobutene III' which is followed by the polymerization with the cyclohexene in the presence of an olefin metathesis catalyst to provide the AB polymer. These reactions may be run in a single reaction vessel.

In certain other embodiments of the invention, the cyclobutene III', IIIa', IIIb' and IIIc' is prepared separately. The cyclobutene III', IIIa', IIIb' and IIIc' is treated with the cyclohexene II or IIa in the presence of an olefin metathesis catalyst to provide the AB copolymer.

The catalyst may be any olefin metathesis catalyst known in the art, such as those disclosed in WO 03/070779. It is preferably an alkylidene ruthenium complex, and more preferably a complex of formula $(L)_2(L')X_2Ru=CHR'$, wherein R' may be, for example, H, $C_1$-$C_{10}$ alkyl, $C_2$-$C_{10}$ alkenyl, $C_3$-$C_6$ cycloalkyl, or aryl. The ligand L is typically a trialkyl phosphines, triarylphosphines, tri(cycloalkyl) phosphines, pyridines, aryl, wherein aryl is optionally substituted with a halogen. L' is a second ligand, and may be a trialkyl phosphine, triarylphosphine, tri(cycloalkyl)phosphine, or a pyridine. L' may also be an imidazolin-2-ylidine carbene of formula IV:

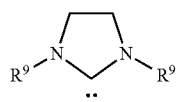

(IV)

wherein $R^9$ may be selected from the group, but is not limited to a $C_1$-$C_6$ alkyl group or aryl. In certain embodiments, X is a halogen or pseudohalogen such as F, Cl, Br, $NO_3$, $CF_3$, or $CF_3COO^-$.

In certain embodiments, L is a pyridine, optionally 3-bromopyridine; and L' is an imidazolin-2-ylidine carbene. In another embodiment, $R^9$ is preferably mesityl, 2-methylphenyl, 2-ethylphenyl, 2-isopropylphenyl, 2,3-diisopropylphenyl, 2,6-difluorophenyl, or 3,5-di-t-butylphenyl.

The polymers of the present invention may be prepared according to the representative Scheme 1.

Scheme 1

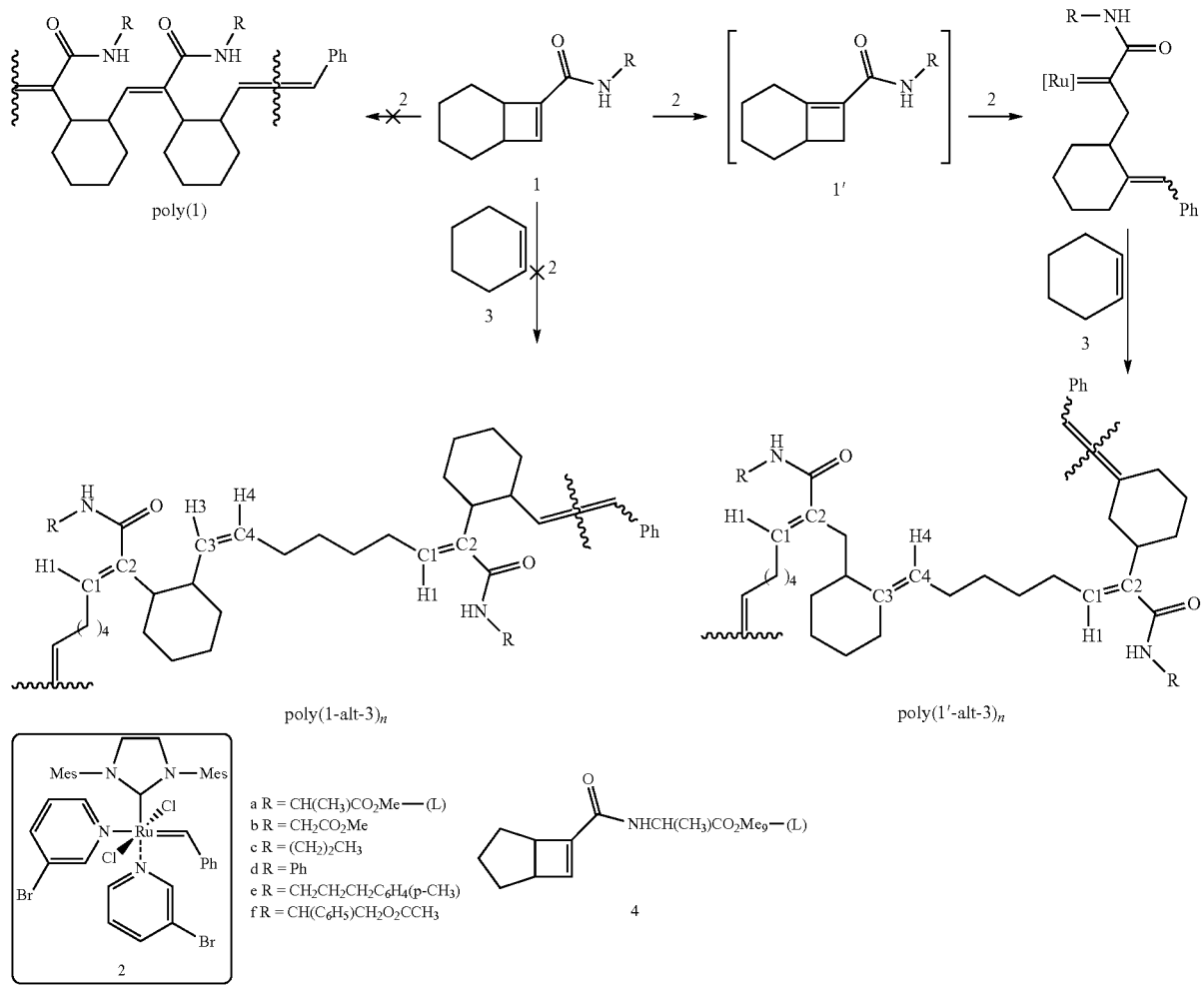

We tested the corresponding bicyclo[4.2.0]oct-7-ene-7-carboxamides 1a-f in ROMP reactions with the Grubbs III catalyst 2 (Scheme 1). Surprisingly, under ROMP conditions, each of the amides 1 isomerized to the bicyclo[4.2.0]oct-1(8)-ene-8-carboxamide 1'. None of the amides showed evidence of homopolymerization in the presence of catalyst 2.

On the other hand, addition of cyclohexene 3 to isomerized amides 1' in the presence of catalyst 2 provided a reaction manifold for the isomerized amides that led to linear, alternating copolymers, poly(1'-alt-3)$_n$, of impressive length. We now refer to this tandem reaction as i-AROMP for isomerization, alternating ring-opening metathesis polymerization.

Alternatively, bicyclo[4.2.0]oct-1(8)-ene-8-carboxamides can be prepared from bicyclo[4.2.0]oct-1(8)-ene-8-carboxylic acids prepared by methods known in the art. See (i) Fleming, I.; Harley-Mason, J. J. Chem. Soc. 1964, "403. The reaction of enamines with electrophilic olefins. A synthesis of cyclobutanes," 2165-2174. DOI: 10.1039/JR9640002165; (ii) Banwell, M. G.; Vogt, F.; Wu, A. W. Australian Journal of Chemistry 2006, "Assembly of the 1-Azaspiro[5.5]undecane Framework Associated with Perhydrohistrionicotoxin via Electrocyclic Ring-Opening of a Ring-Fused gem-Dichlorocyclopropane and Trapping of the Resulting π-Allyl Cation by a Tethered, Nitrogen-Centered Nucleophile," 59, 415-425. DOI: http://dx.doi.org/10.1071/CH06218.

EXAMPLES

The following examples further illustrate the invention, but should not be construed to limit the scope of the invention in any way.

All metathesis reactions were performed under an $N_2$ atmosphere. Solvents, e.g. $CH_2Cl_2$ and THF were purified with Pure Process Technology (PPT). Deuterated solvents for all ring-opening reactions were degassed and filtered through basic alumina before use. Catalyst $Cl_2(H_2IMes)(PCy_3)Ru$=CHPh was purchased from Aldrich. Cyclohexene-$D_{10}$ was purchased from CDN Isotope Inc. The synthesis of catalyst (3-Br-Pyr)$_2Cl_2$(H$_2$IMes)Ru=CHPh, 2, was performed according to the procedure of Love et al. (Love, J. A.; Morgan, J. P.; Trnka, T. M.; Grubbs, R. H. Angew. Chem. Int. Ed. 2002, 41, 4035-4037). Experimental procedures for the preparation of amides 1 and 4 are below.

Solvents, e.g. $CH_2Cl_2$ and THF were purified with Pure Process Technology (PPT). Mallinckrodt silica gel 60 (230-400 mesh) was used for column chromatography. Analytical thin layer chromatography (TLC) was performed on precoated silica gel plates (60F$_{254}$), flash chromatography on silica gel-60 (230-400 mesh), and Combi-Flash chromatography on RediSep normal phase silica columns (silica gel-60, 230-400 mesh). Bruker Nanobay 400, Avance III 500, Avance III 700 NMR instruments were used for analysis. Chemical shifts were calibrated from residual undeuterated solvents; they are denoted in ppm (δ). Molecular weights and molar-mass dispersities except poly(1c'-alt-3)$_{424}$ were measured with a gel phase chromatography system constructed from a Shimadzu pump coupled to a Shimadzu UV detector. THF served as the eluent with a flow rate of 0.700 mL/min on a Phenogel 5μ MXL GPC column (10$^5$ Da exclusion limit), Phenomenex. The dispersity of poly(1c'-alt-3)$_{424}$ was measured on a size exclusion chromatography system constructed from a GPCmax VE-2001 pump coupled to a model 305 TDA detector. CHCl$_3$ served as the eluent with a flow rate of 1.00 mL/min on a TSKgel GMH$_{HR}$-H(S) column (13 μm, 4×10$^8$ exclusion limit). Both GPCs were calibrated with poly(styrene) standards at 30° C. The T$_g$ was measured by differential scanning calorimetry (DSC) using a Perkin-Elmer DSC-7 thermal analysis system (Shelton, Conn., USA), at a scan rate of 10° C./min. Polymer samples (each weighing approx. 1.2 mg) were sealed in aluminum cassettes under dry conditions.

Example 1: Synthesis of Monomers

Bicyclo[4.2.0] and [3.2.0] esters were synthesized by a modification of Snider's approach (Snider, B. B.; Rodini, D. J.; Cionn, R. S. E.; Sealfon, S. *J. Am. Chem. Soc.* 1979, 101, 5283-5493) as previously described. (Tan, L.; Parker, K. A.; Sampson, N. S. *Macromolecules* 2014, 47, 6572-6579). Basic hydrolysis provided the carboxylic acids that were coupled to selected amines to yield amides 1a-1e and 4. Diastereomers 1f and 1f* were prepared from the mixture of racemic bicyclo[4.2.0]oct-7-ene-7-carboxylic acid and (S)-phenylglycinol, separated, and then, individually acylated. Relative stereochemistry was not assigned to the diastereomers.

Example 2: Attempted ROMP of Bicycloamides: Discovery of Isomerization

We submitted the bicyclo[4.2.0] amides 1 to ROMP conditions with catalyst 2 in CDCl$_3$ and monitored the reactions by $^1$H NMR. The bicyclic monomers underwent rapid reactions. The olefinic proton signals at ~6.7 ppm disappeared or nearly disappeared (FIGS. 57a and b) within 15 minutes to 24 hours (Table 1, entries 1-7). However, no polymerization could be detected. In contrast, when amide 4 was stirred with catalyst 2 for 18 hours at 25° C., only a 2% decrease in the intensity of the olefinic resonance was observed.

Figure 57:
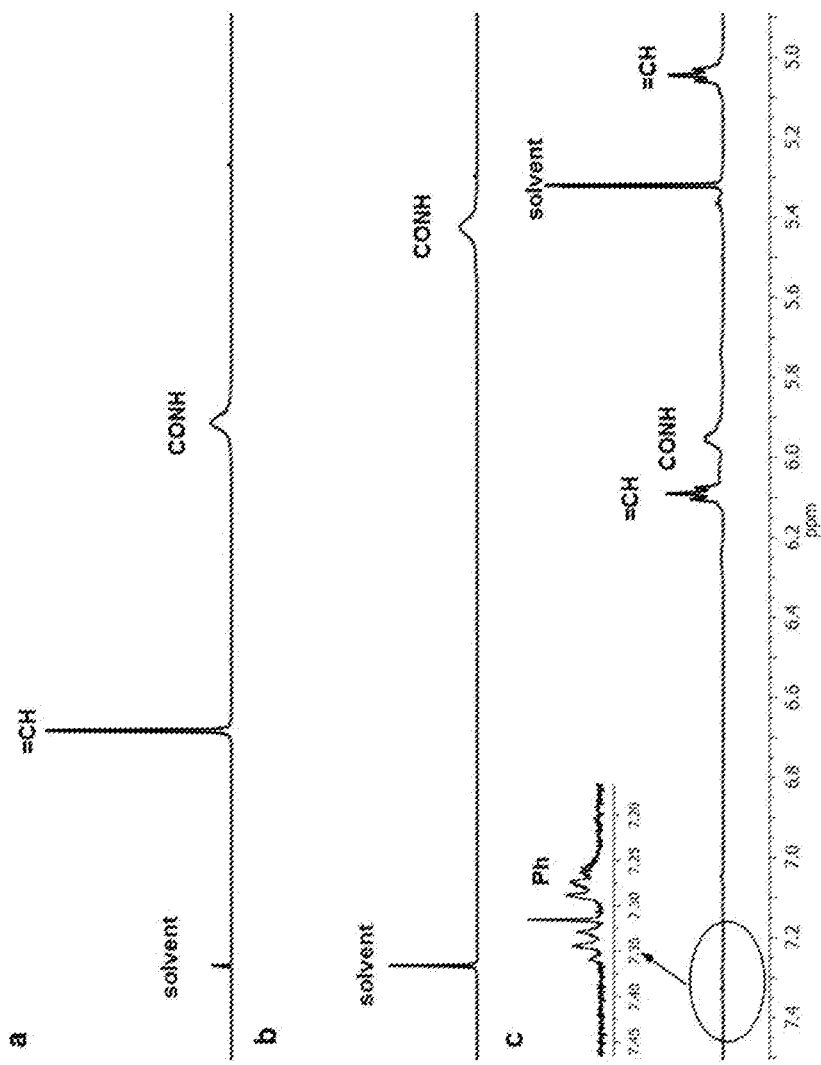
FIG. 57 shows the $^1$H NMR spectra of the alkene and aromatic region of i-AROMP starting material, intermediate, and product. (a) Monomer 1c in CDCl$_3$; (b) Formation of the tetrasubstituted isomer 1c' in the presence of catalyst 2 in CDCl₃; (c) Alternating copolymer poly(1c'-alt-3)$_{424}$ formed upon addition of cyclohexene 3 to 1c' in CD₂Cl₂. CD₂Cl₂ was used to avoid overlap with aromatic proton signals and to allow their integration. The two alkene signals correspond to H1 and H4 of poly (1c'-alt-3)$_{424}$.
Figure 58:
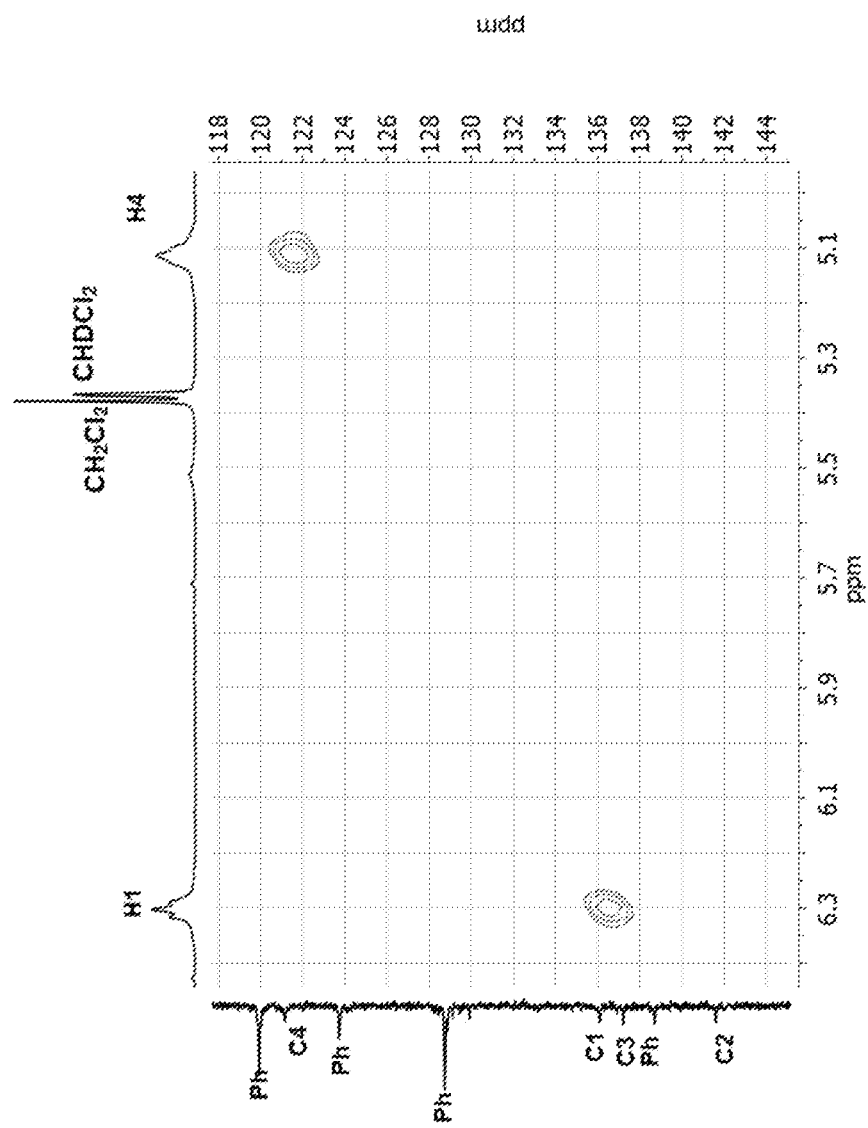
FIG. 58 shows the alkene region of the HSQC spectrum of poly(1d'-alt-3)$_{50}$ in CD₂Cl₂. The polymer backbone has only four alkene carbons and two alkene hydrogens corresponding to C1-C4 and H1 and H4 in Scheme 1.

The products derived from monomers 1c and 1d were selected for further study. Purification yielded compounds 1c' and 1d' with molecular masses identical to those of the starting materials. The spectroscopic signatures of 1c' and 1d' were distinct from those of 1c and 1d indicating that isomerization had occurred. Relative to the $^1$H NMR spectra of the starting materials, those of 1c' and 1d' contained one more methylene proton signal, one less methine signal, and no olefinic proton resonance (FIGS. 57 and 1). Further spectroscopic characterization of 1c' by HSQC NMR spectroscopy indicated that it retains the unsaturated bicyclic structure of 1c, but that the double bond had migrated (Scheme 1 and FIGS. 2-3).

TABLE 1

Isomerization of amides effected by catalyst 2.

| entry | 1 | [1]:[cat] | Catalyst/additive | Time (h) | % conv[b] |
|---|---|---|---|---|---|
| 1 | 1a | 20:1[a] | 2 | 16 | 90 |
| 2 | 1b | 50:1[a] | 2 | 8 | 95 |
| 3 | 1c | 50:1[a] | 2 | 1.5 | 100 |
| 4 | 1d | 20:1[a] | 2 | 0.3 | 100 |
| 5 | 1e | 50:1[a] | 2 | 6 | 100 |
| 6 | 1f | 10:1[a] | 2 | 24 | 70 |
| 7 | 1f* | 10:1[a] | 2 | 24 | 90 |
| 8 | 1e | 10:1[c] | 2 | 14 | 100 |
| 9 | 1e | 10:1[c] | 2/3-Br-pyridine (50 eq) | 14 | 35 |
| 10 | 1e | 5:1[a] | 2 | 1 | 100 |
| 11 | 1e | 5:1[a] | (Cl)$_2$(H$_2$IMes)(PCy$_3$)Ru=CHPh | 14 | 5 |
| 12 | 1e | 10:1[c] | 2/1,4-benzoquinone (5 eq) | 14 | 100 |
| 13 | 1c | 10:1[c] | 2 | 1.5 | 100 |
| 14 | 1c | 10:1[c] | 2/8% MeOH | 24 | 65 |

[a][cat] = 0.01M, CD$_2$Cl$_2$, 35° C.
[b]% conv was determined by monitoring the monomer alkene resonances in $^1$H NMR spectra.
[c][cat] = 0.005M, CD$_2$Cl$_2$, 35° C.

Typically, tetra-substituted olefins are not obtained with catalyst 2. (Stewart, I. C.; Ung, T.; Pletnev, A. A.; Berlin, J. M.; Grubbs, R. H.; Schrodi, Y. *Org. Lett.* 2007, 9, 1589-1592; Berlin, J. M.; Campbell, K.; Ritter, T.; Funk, T. W.; Chlenov, A.; Grubbs, R. H. *Org. Lett.* 2007, 9, 1339-1342; Rost, D.; Porta, M.; Gessler, S.; Blechert, S. *Tetrahedron Lett.* 2008, 49, 5968-5971; Ackermann, L.; Fürstner, A.; Weskamp, T.; Kohl, F. J.; Herrmann, W. A. *Tetrahedron Lett.* 1999, 40, 4787-4790). In our system, further isomerization to the bicyclo[4.2.0]oct-1(2)-ene-8-carboxamide is unfavorable because in this compound the alkene is not in conjugation with the amide. We observed that the bicyclo[3.2.0] system 4 does not undergo appreciable isomerization. As noted above, regioisomer 4' is not formed upon addition of catalyst 2 to amide 4.

Example 3: Mechanism of Isomerization

Control experiments support the role of species 2 as the isomerization catalyst. No isomerization was observed upon incubation of 1c in CH$_2$Cl$_2$ at 35° C. for 16 hours in the absence of catalyst 2. Over the course of our experiments, we utilized four different batches of 2. All four preparations of 2 catalyzed isomerization to the same extent and at the same rate. Furthermore, addition of 50 equivalents of 3-bromopyridine to amide 1e and catalyst 2 reduced the percentage of isomerization 3-fold over a 14-hour time period as compared to isomerization in the absence of exogenous 3-bromopyridine ([2]=0.005 M, Table 1, entry 8 vs 9). Likewise, we found that 20 mol % of (Cl)$_2$(H$_2$IMes)(PCy$_3$) Ru=CHPh, for which PCy$_3$ ligand dissociation is less favored, catalyzed less than 5% isomerization of amide 1e in 14 hours as compared to 100% conversion with 20 mol % catalyst 2 within 1 hour (Table 1, entry 10 vs 11). These experiments indicate that coordination of the substrate to the Ru catalyst is involved in the isomerization.

Cyclobutenes are sensitive to acid-catalyzed decomposition and/or reaction. In order to exclude the possibility that substrates 1 were being converted to isomers 1' by adventitious acid, we repurified the monomers by passing them through dry basic alumina before subjecting them to catalyst 2. The isomerization rates and product distributions were unchanged.

Ruthenium catalysts promote olefin isomerization. Previous reports (Cadot, C.; Dalko, P. I.; Cossy, J. *Tetrahedron Lett.* 2002, 43, 1839-1841; Dinger, M. B.; Mol, J. C. *Organometallics* 2003, 22, 1089-1095; Dinger, M. B.; Mol, J. C. *Eur. J. Inorg. Chem.* 2003, 2003, 2827-2833; Schmidt, B. *Eur. J. Org. Chem.* 2004, 2004, 1865-1880) have proposed that either a Ru hydride species (McGrath, D. V.; Grubbs, R. H. *Organometallics* 1994, 13, 224-235; Bourgeois, D.; Pancrazi, A.; Nolan, S. P.; Prunet, J. *J. Organomet. Chem.* 2002, 643-644, 247-252; van Rensburg, W. J.; Steynberg, P. J.; Meyer, W. H.; Kirk, M. M.; Forman, G. S. *J Am. Chem. Soc.* 2004, 126, 14332-14333; van Rensburg, W. J.; Steynberg, P. J.; Kirk, M. M.; Meyer, W. H.; Forman, G. S. *J. Organometallic Chem.* 2006, 691, 5312-5325; Ashworth, I. W.; Hillier, I. H.; Nelson, D. J.; Percy, J. M.; Vincent, M. A. *Eur. J Org. Chem.* 2012, 2012, 5673-5677) or a π-allyl Ru complex (McGrath, D. V.; Grubbs, R. H. *Organometallics* 1994, 13, 224-235; Bourgeois, D.; Pancrazi, A.; Nolan, S. P.; Prunet, J. *Organomet. Chem.* 2002, 643-644, 247-252; Higman, C. S.; Plais, L.; Fogg, D. E. *Chem. Cat. Chem* 2013, 5, 3548-3551; Schmidt, B. *J. Mol. Catal. A: Chem.* 2006, 254, 53-57; Trost, B. M.; Kulawiec, R. J. *J. Am. Chem. Soc.* 1993, 115, 2027-2036) is responsible. The Ru hydride can form upon decomposition that occurs with extended reaction times or extreme reaction conditions. (Dinger, M. B.; Mol, J. C. *Organometallics* 2003, 22, 1089-1095; Dinger, M. B.; Mol, J. C. *Eur. J. Inorg. Chem.* 2003, 2003, 2827-2833). The rapid isomerization rates we observe are inconsistent with the formation of a Ru hydride species through decomposition of 2. Moreover, we did not observed Ru hydride resonances at the expected upheld region between 0 and −30 ppm in the $^1$H NMR spectra of the above reactions. Addition of 1,4-benzoquinone, which has been reported to oxidize Ru hydride species and prevent olefin isomerization, (Hong, S. H.; Sanders, D. P.; Lee, C. W.; Grubbs, R. H. *J. Am. Chem. Soc.* 2005, 127, 17160-17161), to our amide 1e did not suppress isomerization. Therefore, a reduced, electron-rich species is unlikely to be responsible for initiation of isomerization (Table 1, entry 8 vs 12).

Alcohols can act as ruthenium reducing agents to enhance Ru hydride formation. (Higman, C. S.; Plais, L.; Fogg, D. E. *Chem. Cat. Chem* 2013, 5, 3548-3551). However, their coordination with Ru can suppress isomerization that proceeds via a π-allyl mechanism. (Schmidt, B. *J. Mol. Catal. A: Chem.* 2006, 254, 53-57; Bielawski, C.; Scherman, O.; Grubbs, R. *Polymer* 2001, 42, 4939-4945; Hillmyer, M. A.; Nguyen, S. T.; Grubbs, R. H. *Macromolecules* 1997, 30, 718-721). Therefore, we tested isomerization of 1c with and without methanol in the presence of 10 mol % catalyst 2. The 1c isomerization reaction containing 8% methanol in $CD_2Cl_2$ proceeded much more slowly than the reaction without methanol; only 65% isomerization was observed over 24 hours as compared to complete isomerization in 1.5 hours in the absence of methanol (Table 1, entry 13 vs 14). Our observations are consistent with isomerization via a π-allyl Ru complex formed upon coordination of amide 1 with catalyst 2. Evidence in hand does not distinguish between direct formation of this species from amide 1 or its formation by a "ring-walking" mechanism. (Curran, K.; Risse, W.; Hamill, M.; Saunders, P.; Muldoon, J.; Asensio de la Rosa, R.; Tritto, I. *Organometallics* 2012, 31, 882-889).

The isomerization rate depends on the nature of the amide nitrogen substituent: 1d>1c>1e>1b>1a>1f/1f*. The rate is slower for amides of α-substituted amines and for amides of amines that include an ester in the alkyl chain.

To investigate further the electronic influence on isomerization, we undertook a control experiment to establish the amount of isomerization with the corresponding methyl bicyclo[4.2.0]oct-7-ene-7-carboxylate. When subjected to catalyst 2 (2 mol %) at 50° C. for 2 days, the ester underwent ROM without isomerization as judged by the disappearance of the catalyst alkylidene proton signal and the remaining signals for the ester starting material. Therefore, the amide moiety assists rapid equilibration of isomers of 1 in the presence of 2.

Without being limited by theory, the kinetic data taken together with the structure-activity data strongly support a mechanism in which equilibration of regioisomers takes place via initial coordination involving the amide functional group and subsequent formation of a transient Ru π-allyl species.

Example 4: Alternating Ring-Opening Metathesis Polymerization of i-Amides

Figure 4:
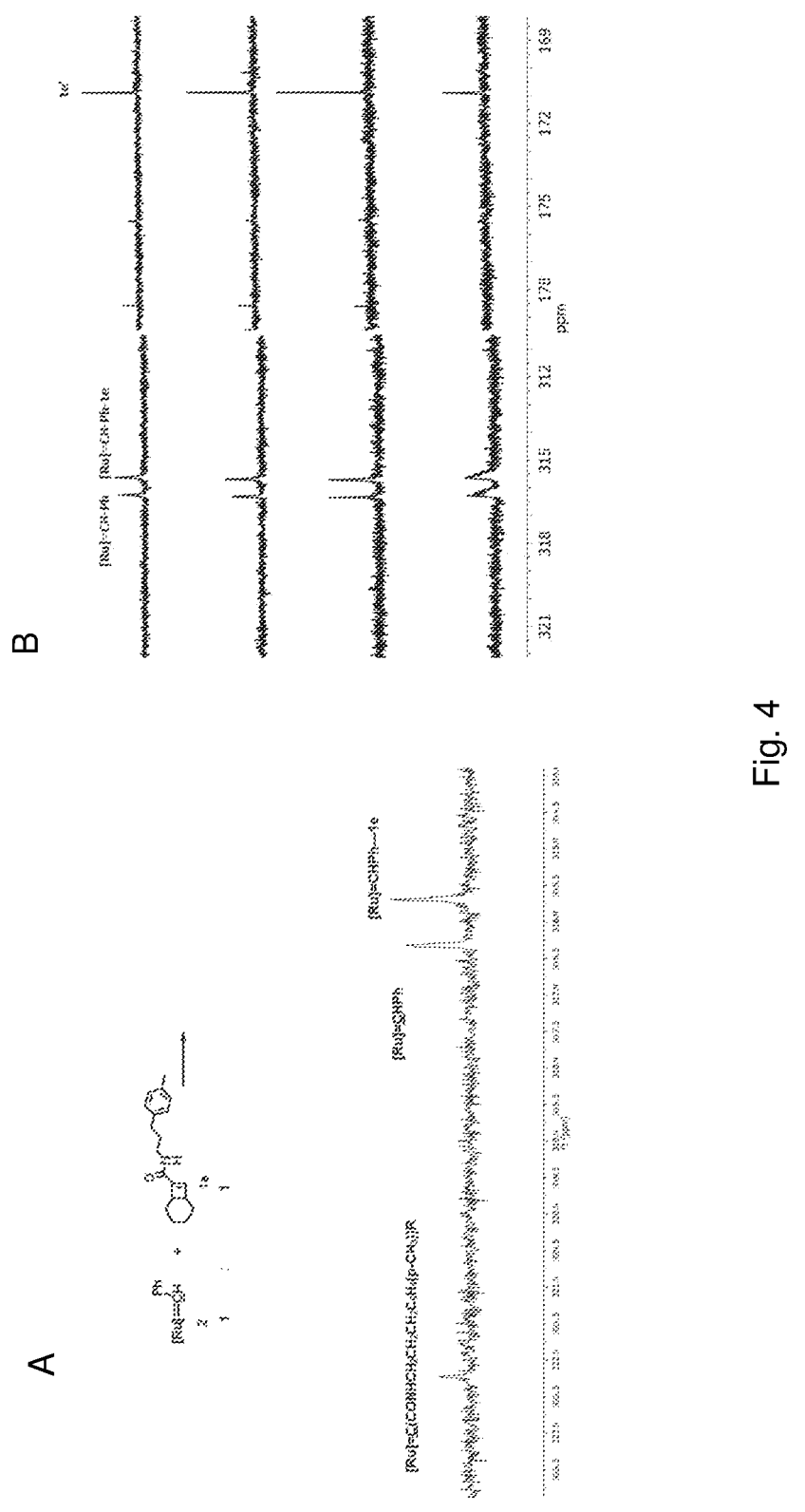

We monitored the isomerization of amide 1e to amide 1e' in the presence of 1 equivalent of catalyst 2 by $^{13}$C NMR spectroscopy. In addition to the growth of the signals corresponding to the formation of amide 1e', remarkably we observed the appearance of new peaks at 322.3 and 178.5 ppm, presumably representing the carbene carbon and the amide carbon respectively in the [Ru]=C(R)CONHR' species (FIG. 4). We also observed a peak at 315.5, representing a second ruthenium carbene species. On the basis of this experiment, we concluded, much to our surprise since monomer 1e' is a tetra-substituted alkene, that ROM occurs upon formation of 1'. Unlike the ruthenium carbenes from amide-substituted cyclobutenes, previously studied in our laboratory, (Lee, J. C.; Parker, K. A.; Sampson, N. S. *J. Am. Chem. Soc.* 2006, 128, 4578-9; Song, A.; Lee, J. C.; Parker, K. A.; Sampson, N. S. *J. Am. Chem. Soc.* 2010, 132, 10513-10520) the amide-substituted carbene derived from 1' does not undergo metathesis with remaining monomer, as noted above.

We reasoned that the amide-substituted carbene derived from 1' might undergo ring-opening cross-metathesis with cyclohexene 3, in a reaction analogous, but not identical, to the reaction of Ru enoic carbenes in our previous AROMP work. (Song, A.; Parker, K. A.; Sampson, N. S. *J. Am. Chem. Soc.* 2009, 131, 3444-3445; Lee, J. C.; Parker, K. A.; Sampson, N. S. *J. Am. Chem. Soc.* 2006, 128, 4578-9; Romulus, J.; Tan, L.; Weck, M.; Sampson, N. S. *Macromol. Lett.* 2013, 2, 749-752; Tan, L.; Parker, K. A.; Sampson, N. S. *Macromolecules* 2014, 47, 6572-6579). Indeed, copolymer was rapidly formed upon addition of cyclohexene 3 (Table 2). The copolymerization of monomer 1c' or 1d' with 3, yields a 50-AB-mer in approximately 2 hours. Remarkably, in light of the steric hindrance in the system, this AROMP is faster under similar conditions than that of the less hindered 1-cyclobutene carboxylic methyl ester/cyclohexene AROMP which yields a 50-AB-mer in 3 hours (Song, A.; Parker, K. A.; Sampson, N. S. *J. Am. Chem. Soc.* 2009, 131, 3444-3445) and that of the corresponding bicyclo[4.2.0]oct-7-ene-7-carboxylic ester which yields a 50-AB-mer in 8 hours. (Tan, L.; Parker, K. A.; Sampson, N. S. *Macromolecules* 2014, 47, 6572-6579).

$^1$H NMR spectroscopy of the copolymers displayed two alkene signals consistent with product from AROMP of isomer 1'. In contrast, AROMP of the original amide 1 would have given copolymer for which the NMR spectrum displayed three alkene signals (Scheme 1).

In order to investigate the possibility of AROMP of the original amide 1c, we premixed cyclohexene 3 with catalyst 2 before addition of amide. However, no polymer resonances were detected before a significant amount of amide 1c had isomerized to amide 1c'. Furthermore, the polymer obtained was identical to poly(1c'-alt-3)$_{10}$ as judged by comparison of the $^1$H NMR spectra. Therefore, isomerization of 1c is faster than ROM, and thus faster than ROMP or AROMP of 1c. Likewise, in the case of amide 1d, isomerization to amide 1d' was complete before polymer appeared.

In the cases of 1a, 1b, 1e, and one of the diastereomers of 1f/1f*, we obtained mixtures of starting materials and alternating polymers. In these systems, then, the rate of isomerization is slower than or similar to the rate of ROM. Owing to their fast isomerization and polymerization, amides 1c' and 1d' were selected for the further characterization of their AROMP products. Polymers poly(1c'-alt-3)$_{97}$, poly(1c'-alt-3)$_{424}$, and poly(1d'-alt-3)$_{50}$ were fully characterized.

Figure 2:
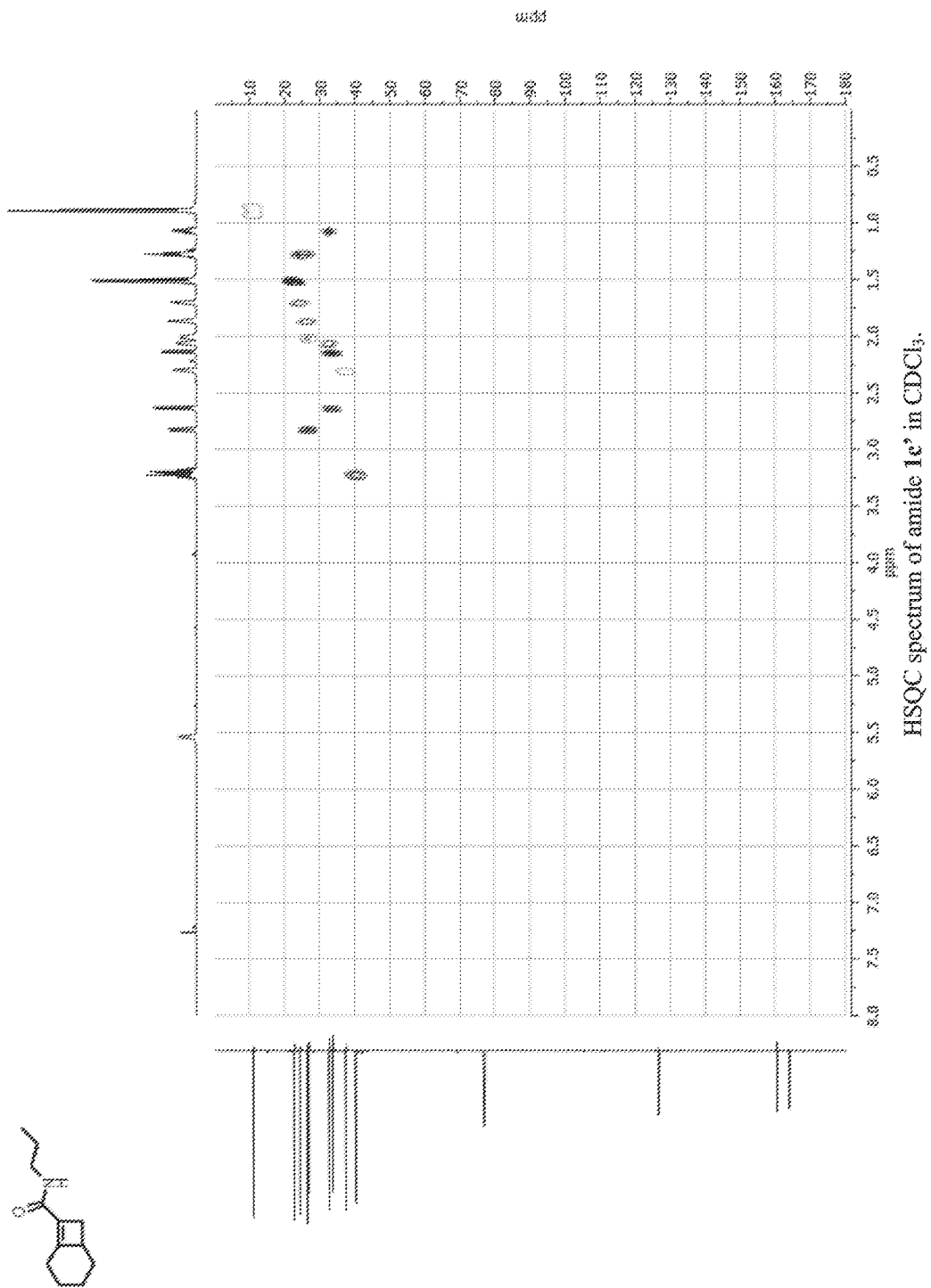
FIG. 2 shows the HSQC spectrum of amide 1c' in CDCl$_3$.
Figure 3:
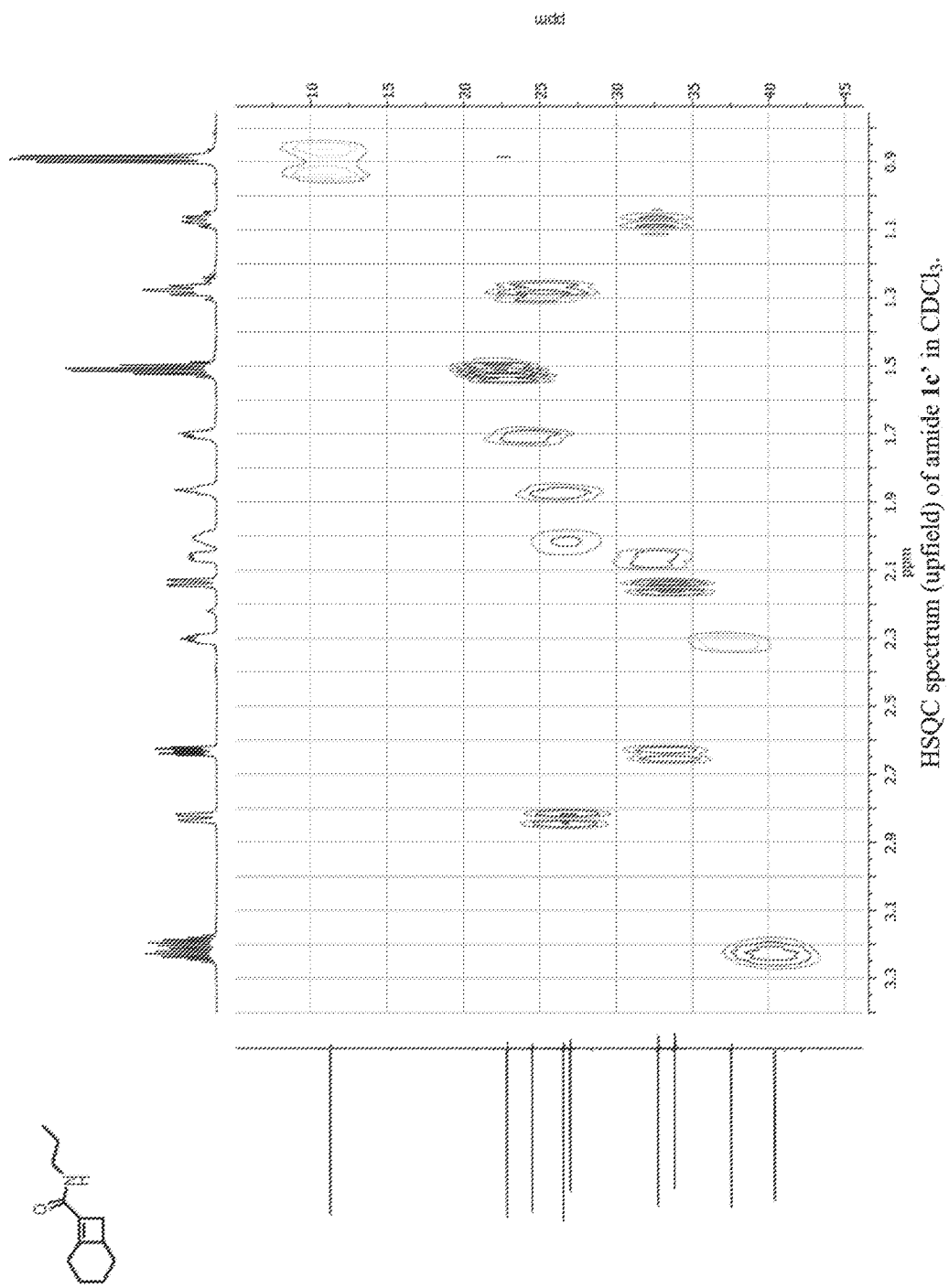
FIG. 3 shows the HSQC spectrum (upheld) of amide 1c' in CDCl$_3$.
Figure 5:
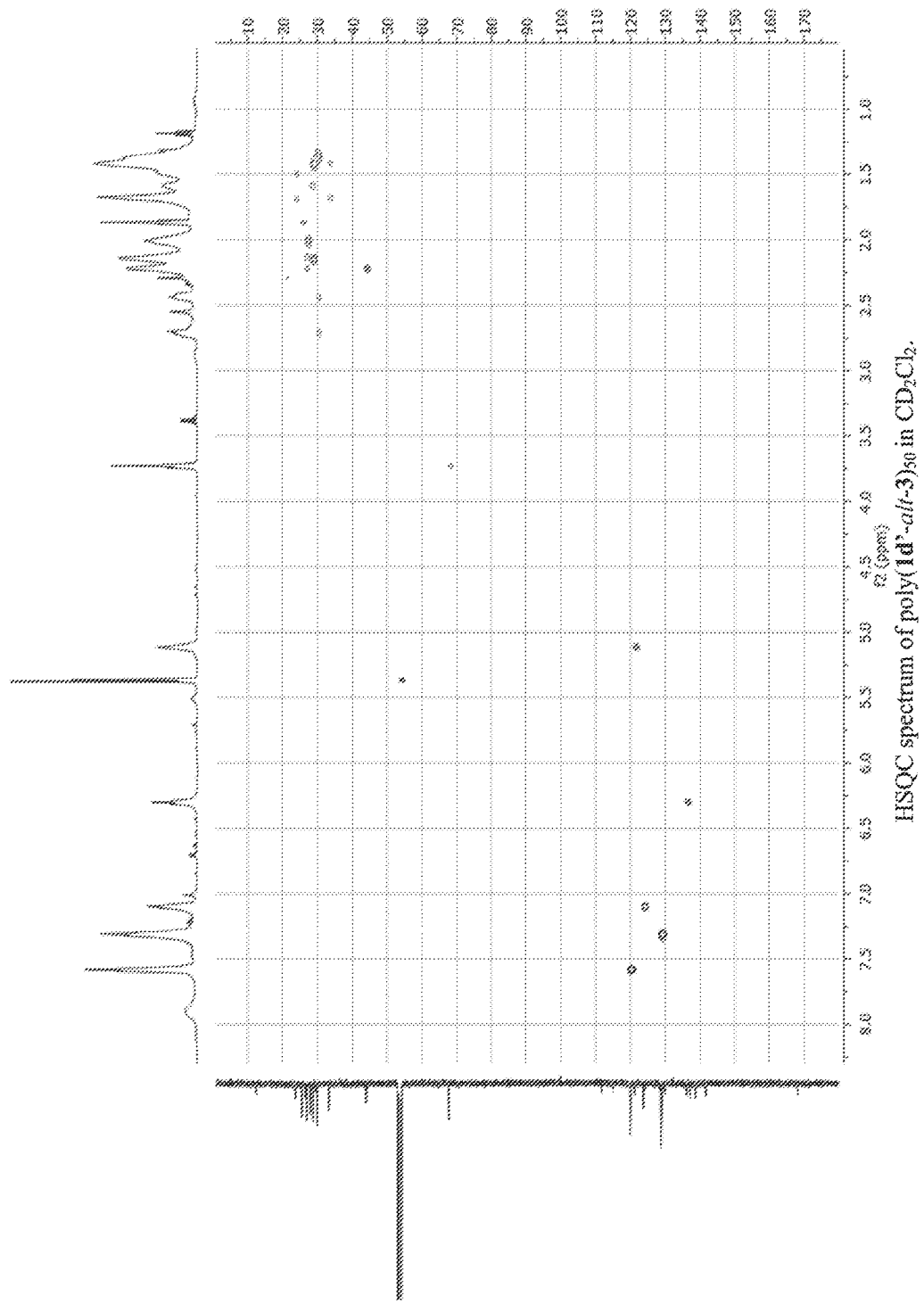
FIG. 5 shows the HSQC spectrum of poly(1d'-alt-3)$_{50}$ in CD$_2$Cl$_2$.

Analysis of poly(1d'-alt-3)$_{50}$ by $^1$H NMR, $^{13}$C NMR, APT and HSQC spectroscopy revealed that the polymer backbone has four alkene carbons and two alkene hydrogens corresponding to C1-C4 and H1 and H4 (Scheme 1, FIG. 5). HSQC spectroscopy confirmed that the amide-substituted olefin is a single stereoisomer; there is a single H1 signal, at 6.29 ppm that correlates with C1 at 136 ppm (FIG. 2). On the basis of comparison of the H1 alkene chemical shift with model compounds, we conclude that the conjugated alkene is of E-configuration. A single H4 signal at 5.11 ppm correlates with C4 at 121 ppm. Because of peak broadening in the polymer, we could not determine if the C3-C4 alkene is stereoregular.

Figure 6:
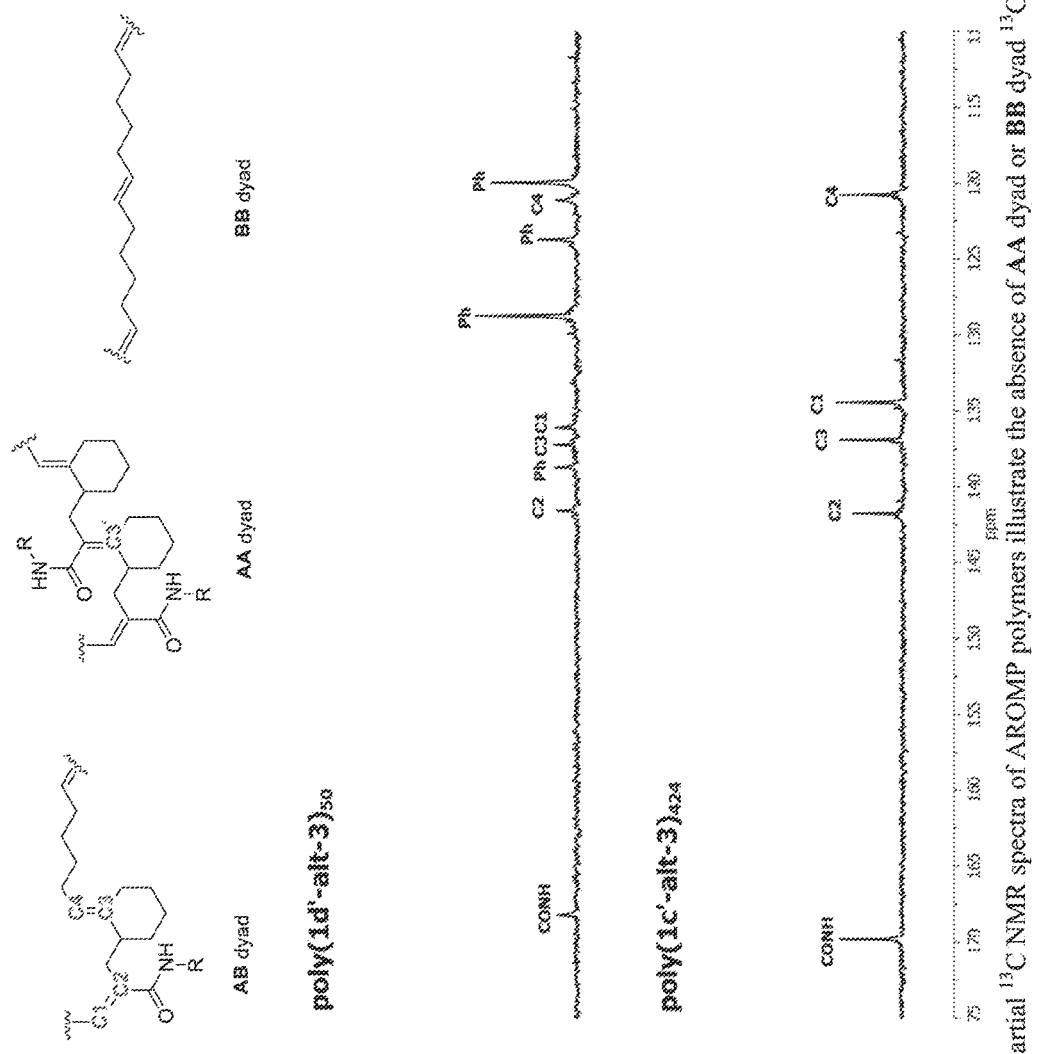
FIG. 6 shows the partial $^{13}$C NMR spectra of AROMP polymers illustrate the absence of AA dyad or BB dyad $^{13}$C resonances.
Figure 7:
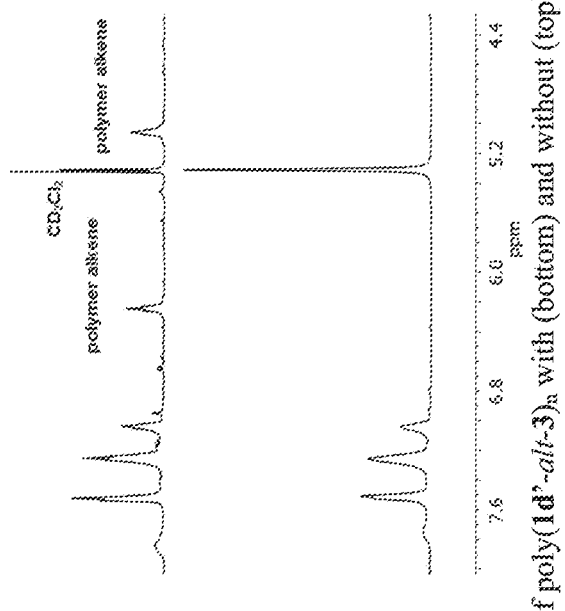
FIG. 7 shows the $^1$H NMR spectra of poly(1d'-alt-3)$_n$ with (bottom) and without (top) deuterium labeling in CD$_2$Cl$_2$.
Figure 8:
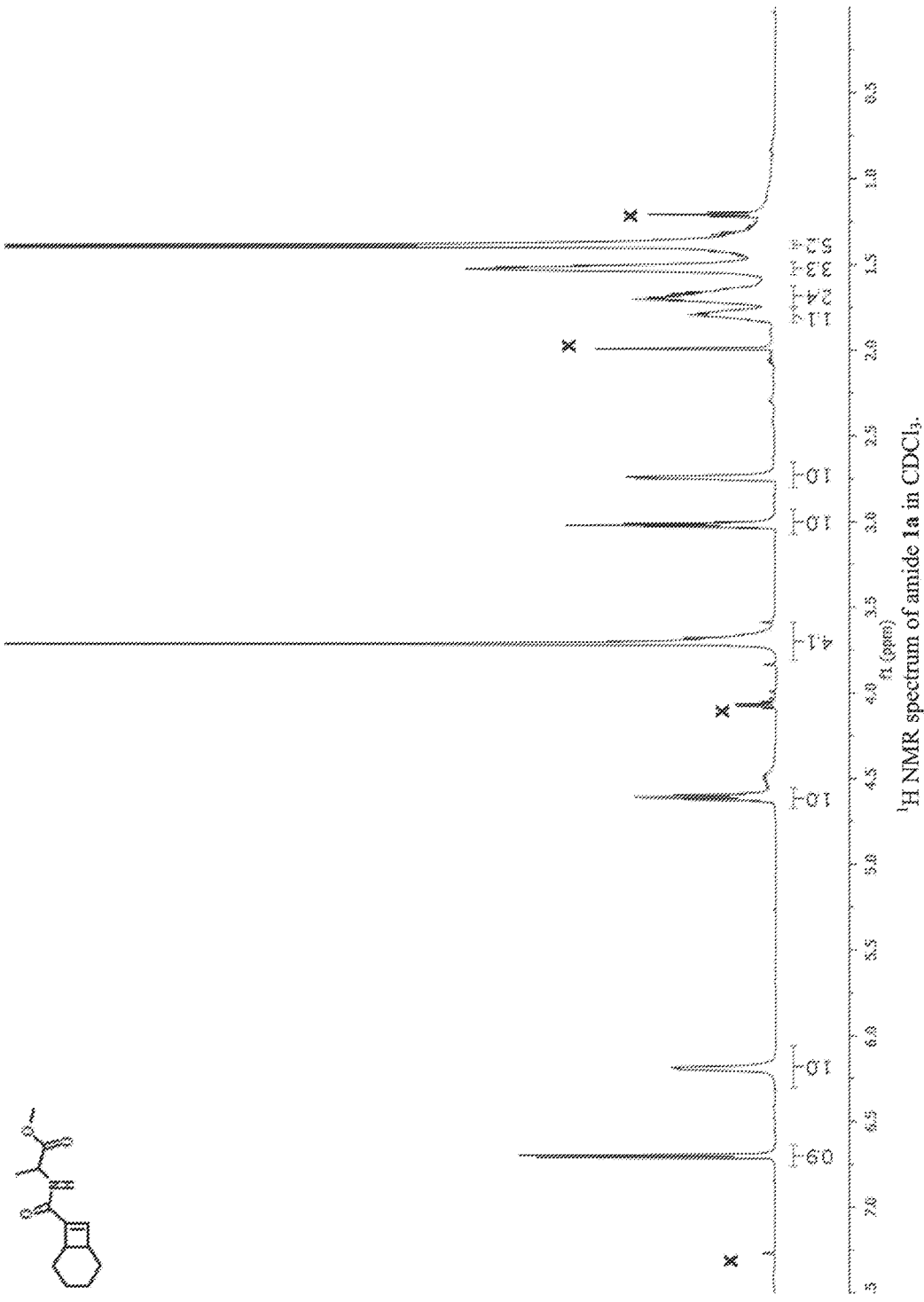
FIG. 8 shows the $^1$H NMR spectrum of amide 1a in CDCl$_3$.
Figure 9:
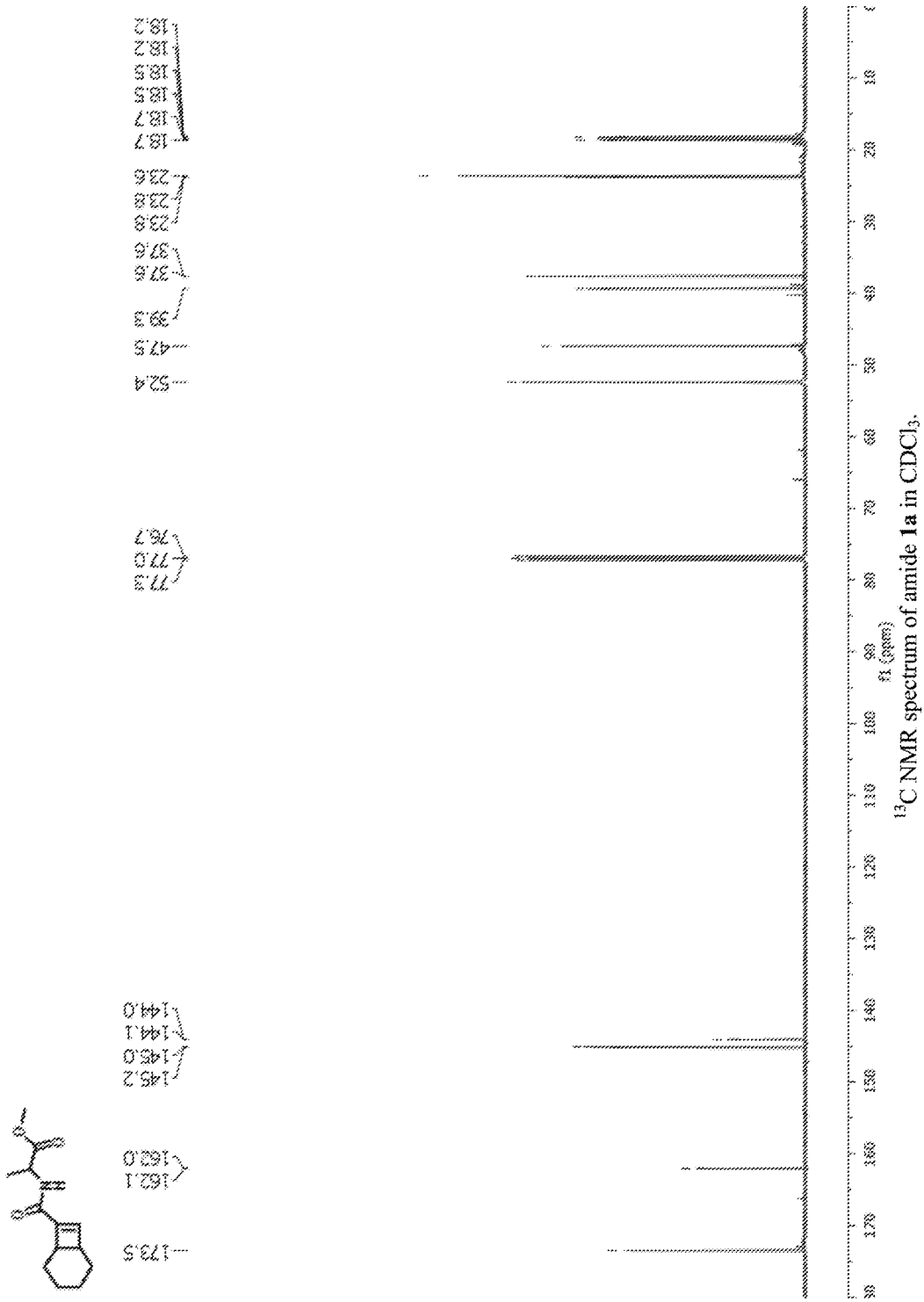
FIG. 9 shows the $^{13}$C NMR spectrum of amide 1a in CDCl$_3$.
Figure 10:
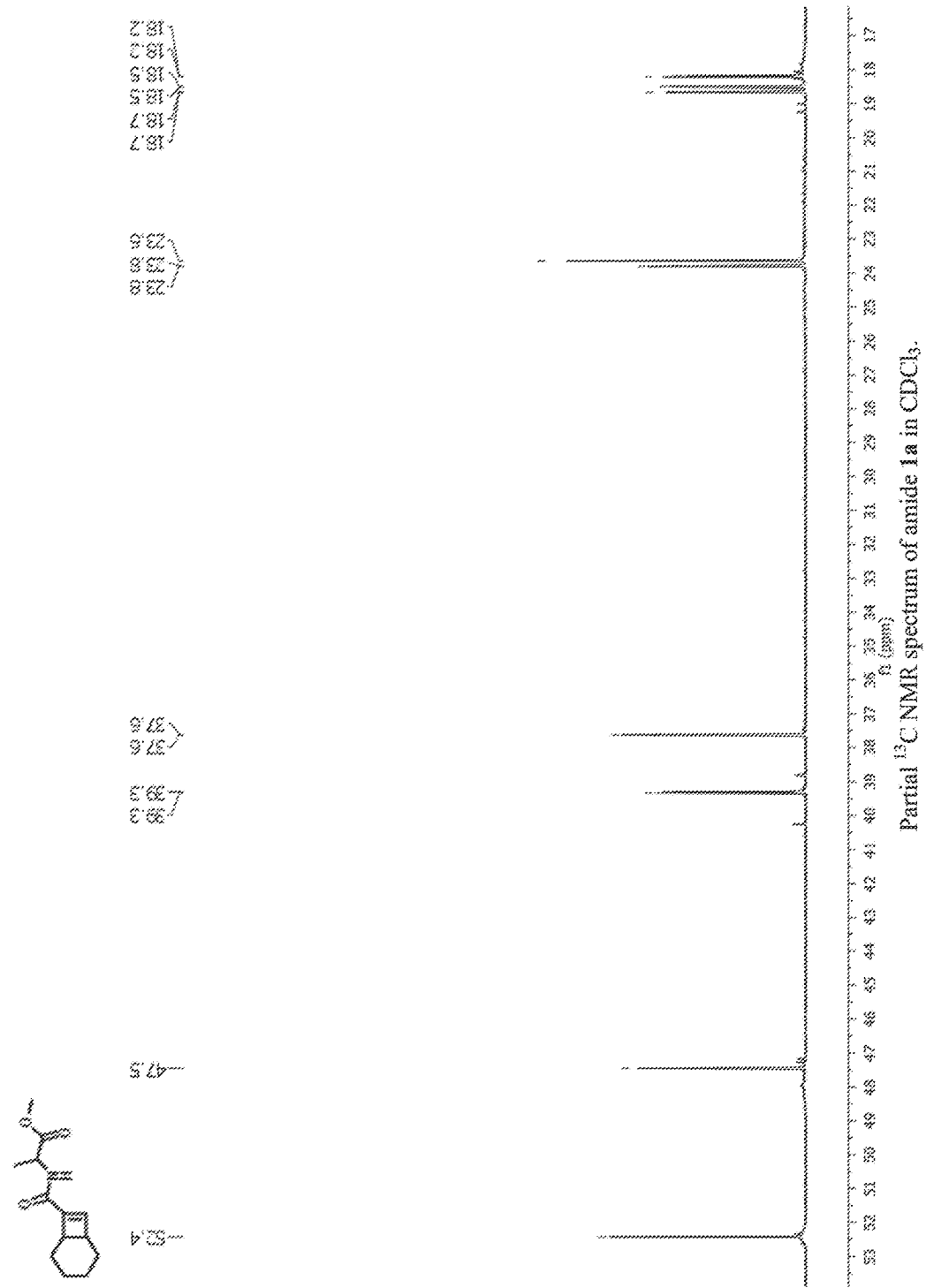
FIG. 10 shows the partial $^{13}$C NMR spectrum of amide 1a in CDCl$_3$.
Figure 11:
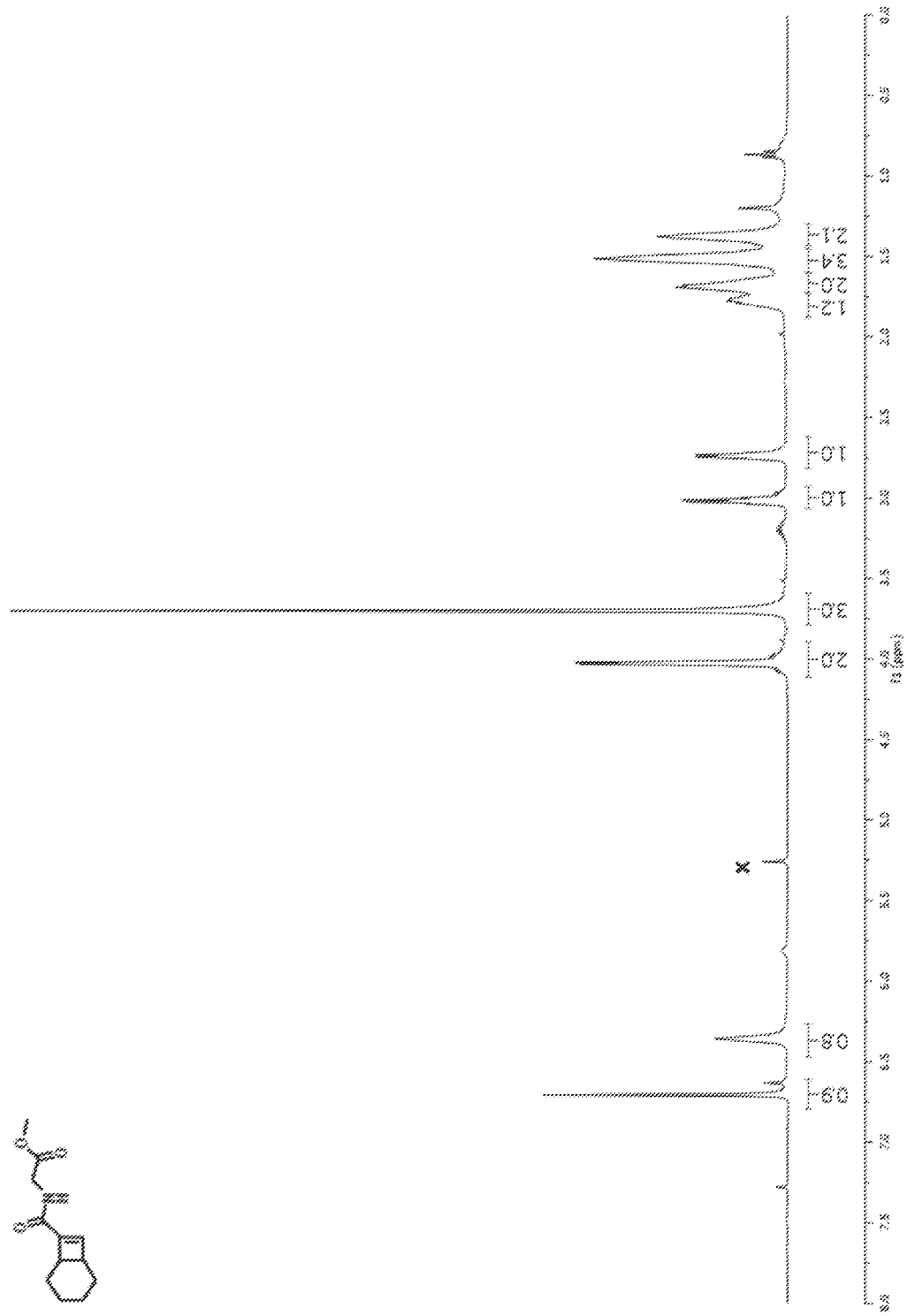
FIG. 11 shows the $^1$H NMR spectrum of amide 1b in CDCl$_3$.
Figure 12:
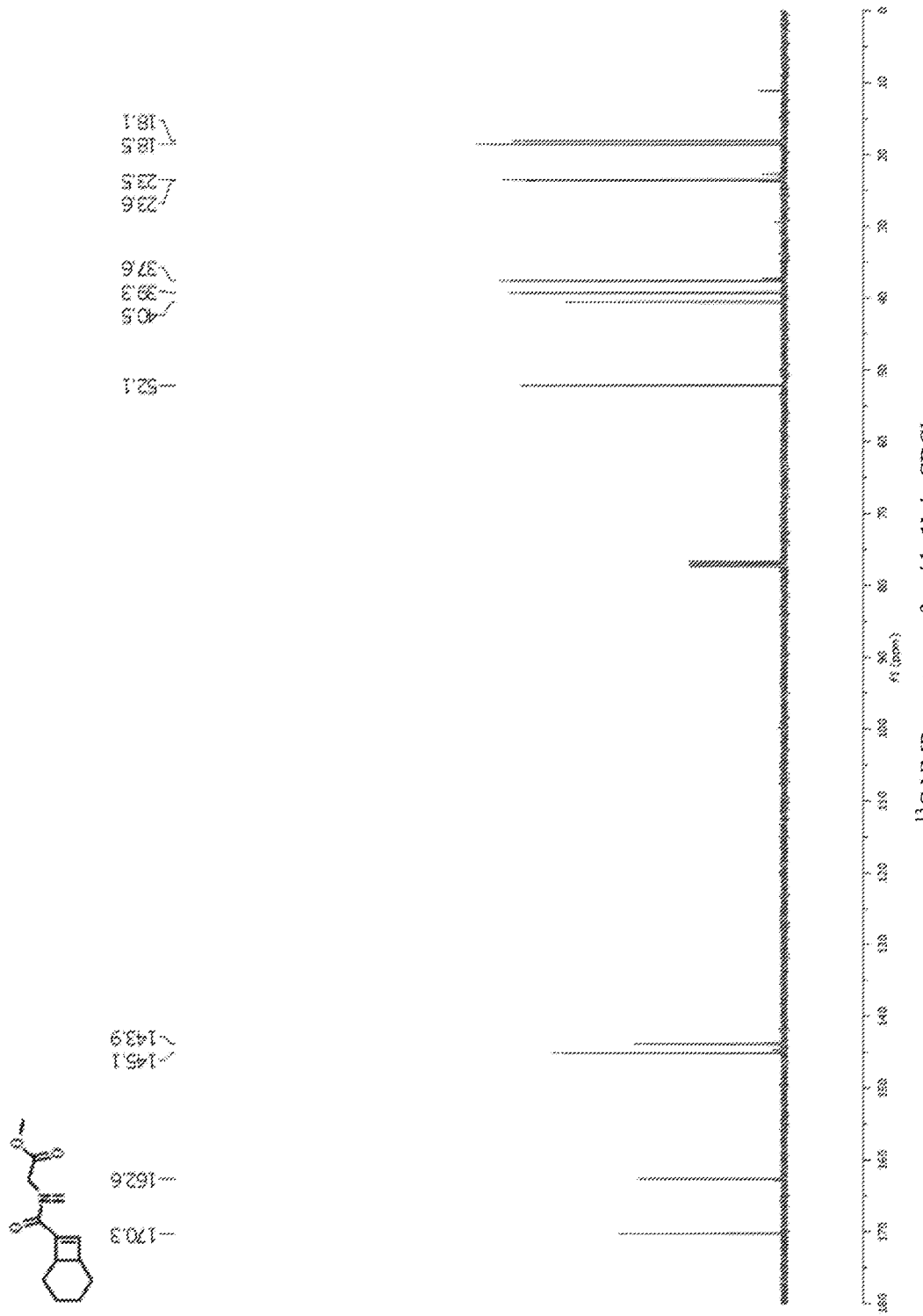
FIG. 12 shows the $^{13}$C NMR spectrum of amide 1b in CDCl$_3$.
Figure 13:
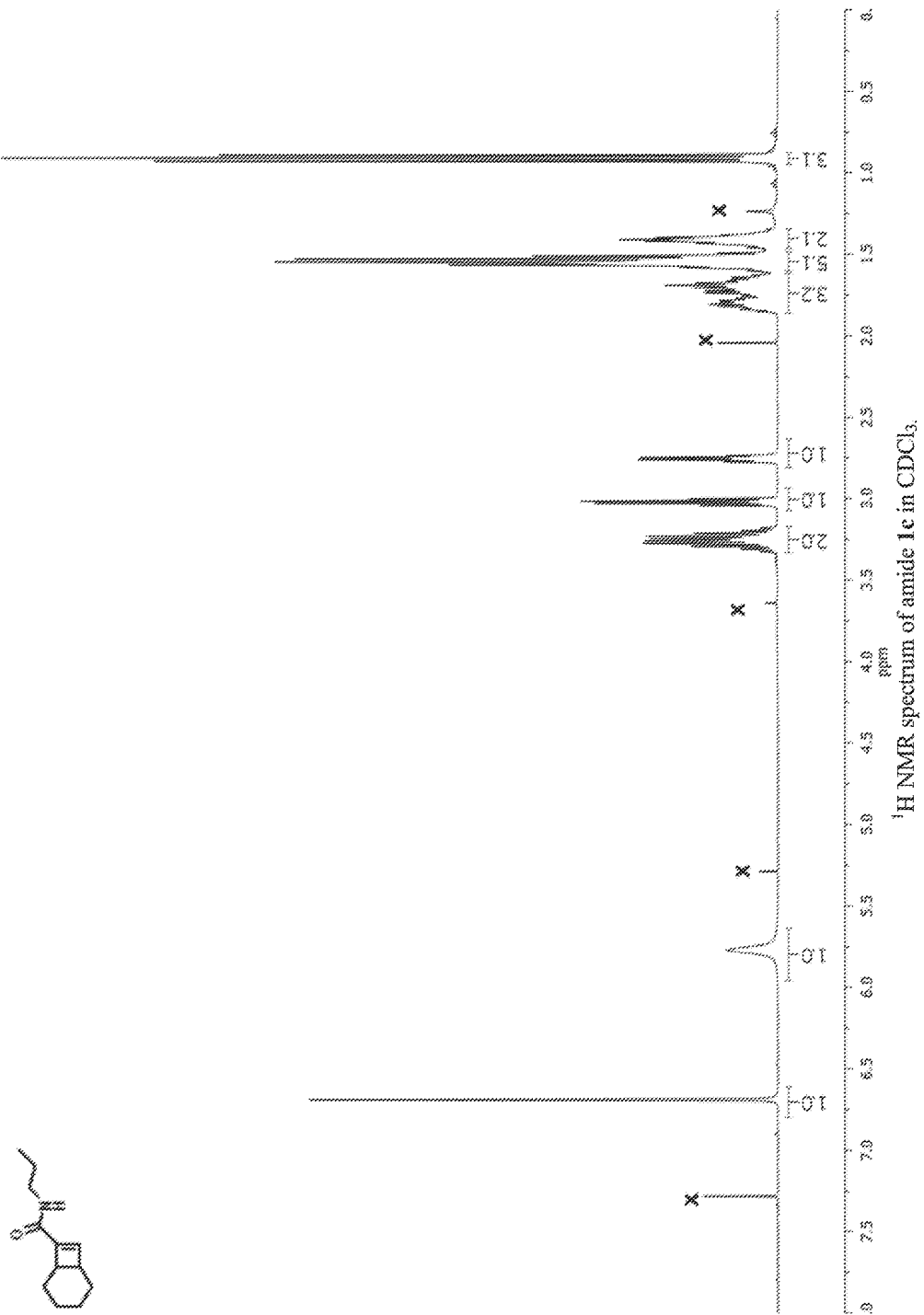
FIG. 13 shows the $^1$H NMR spectrum of amide 1c in CDCl$_3$.
Figure 14:
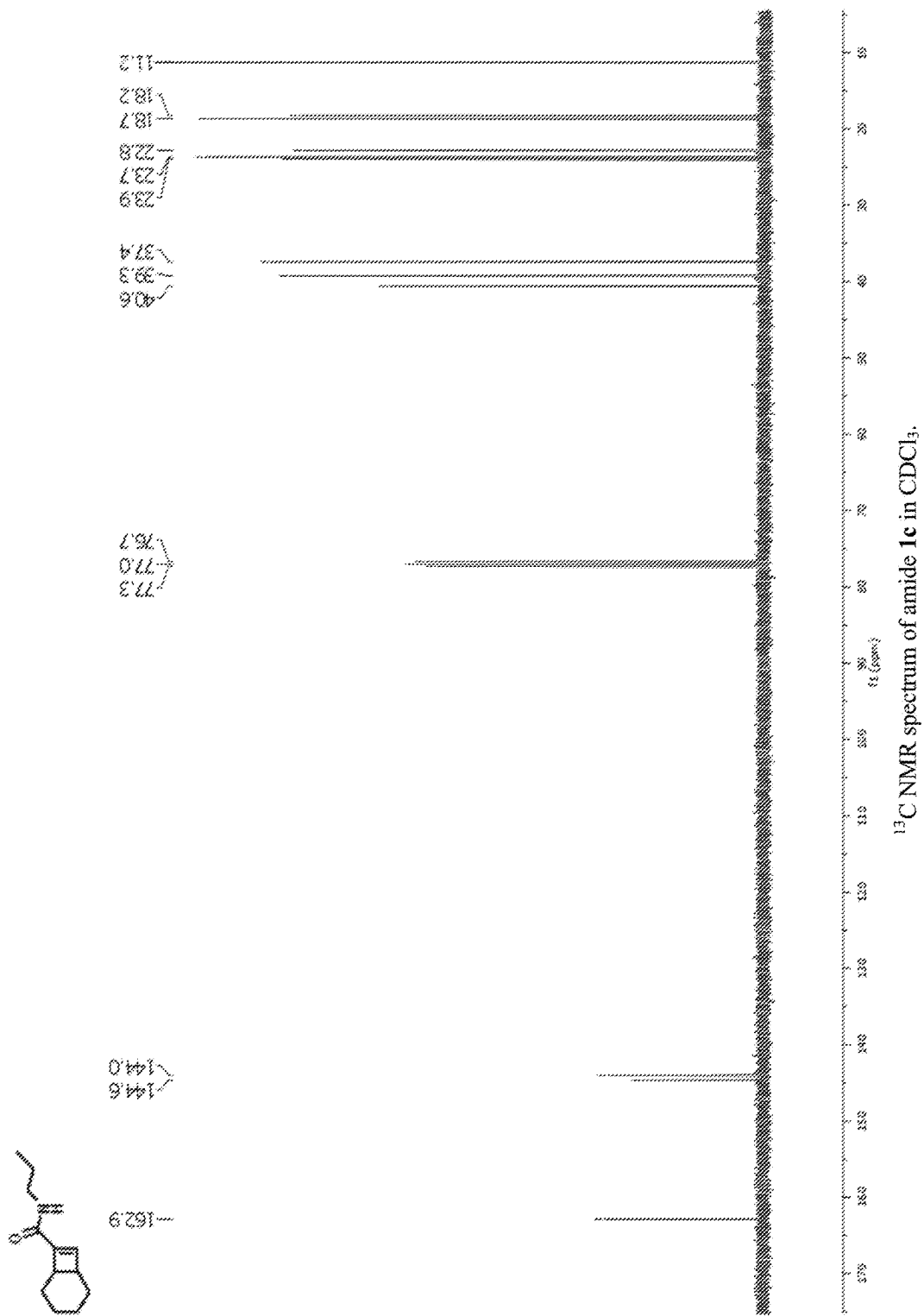
FIG. 14 shows the $^{13}$C NMR spectrum of amide 1c in CDCl$_3$.
Figure 15:
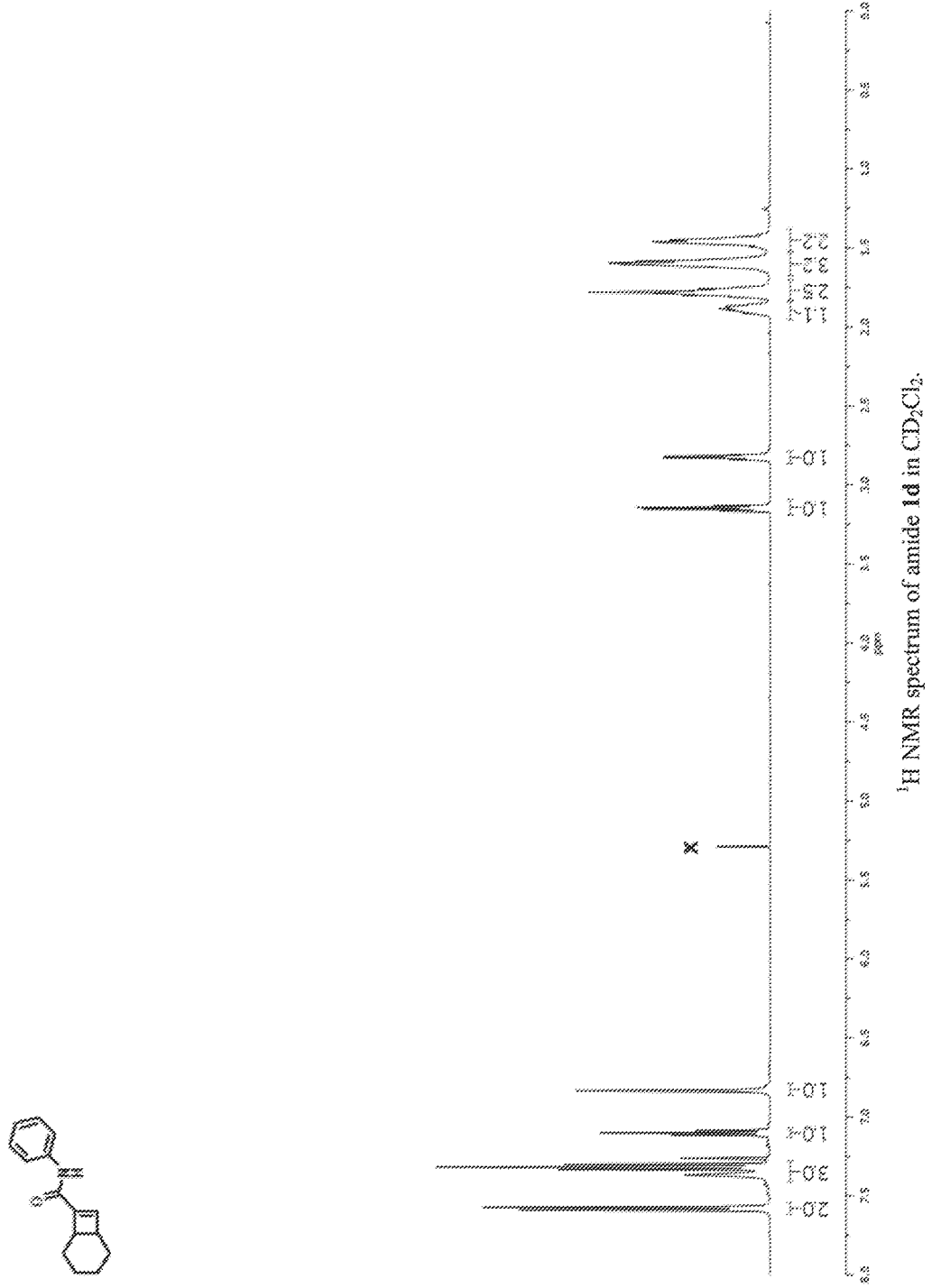
FIG. 15 shows the $^1$H NMR spectrum of amide 1d in CD$_2$Cl$_2$.
Figure 16:
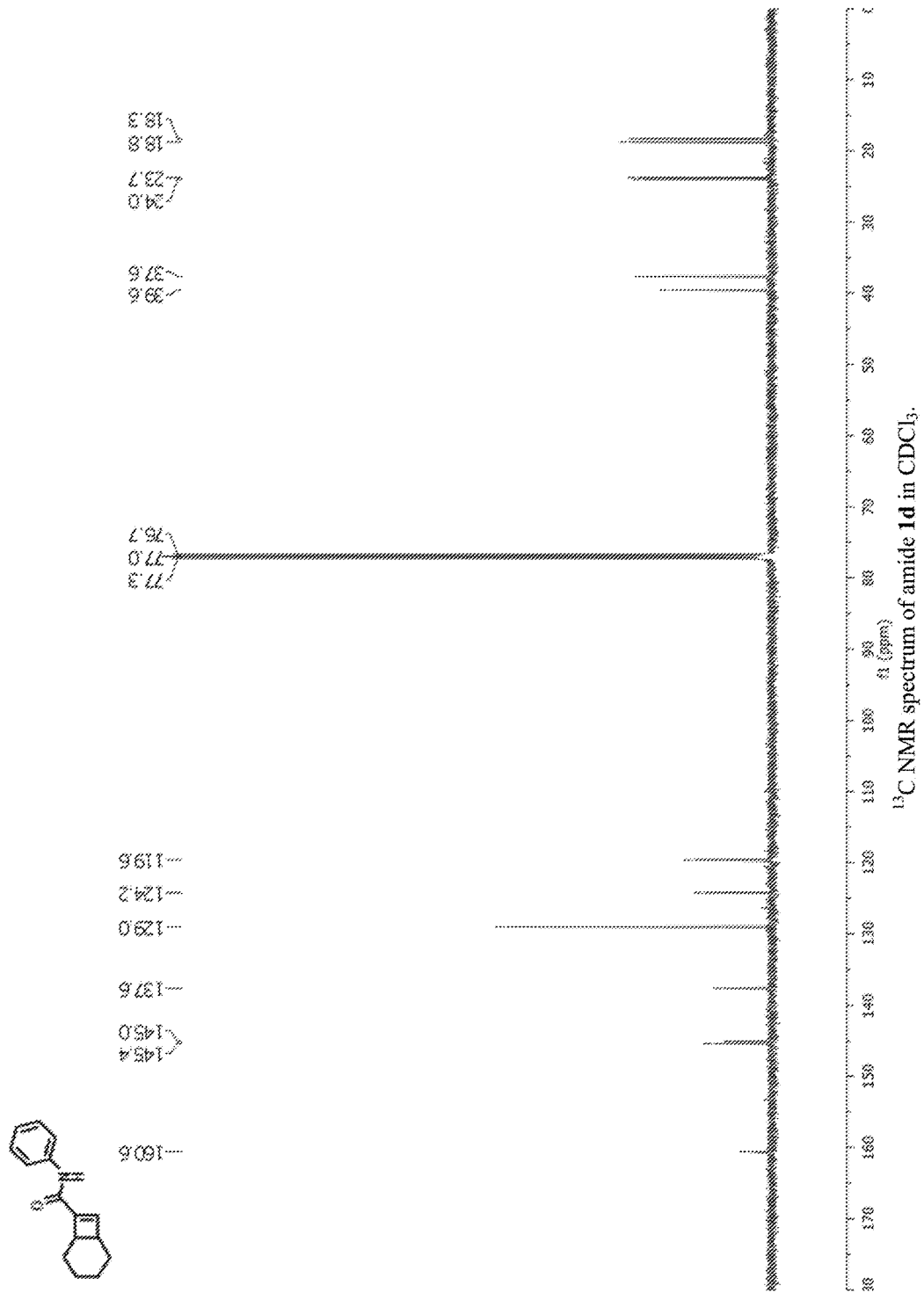
FIG. 16 shows the $^{13}$C NMR spectrum of amide 1d in CDCl$_3$.
Figure 17:
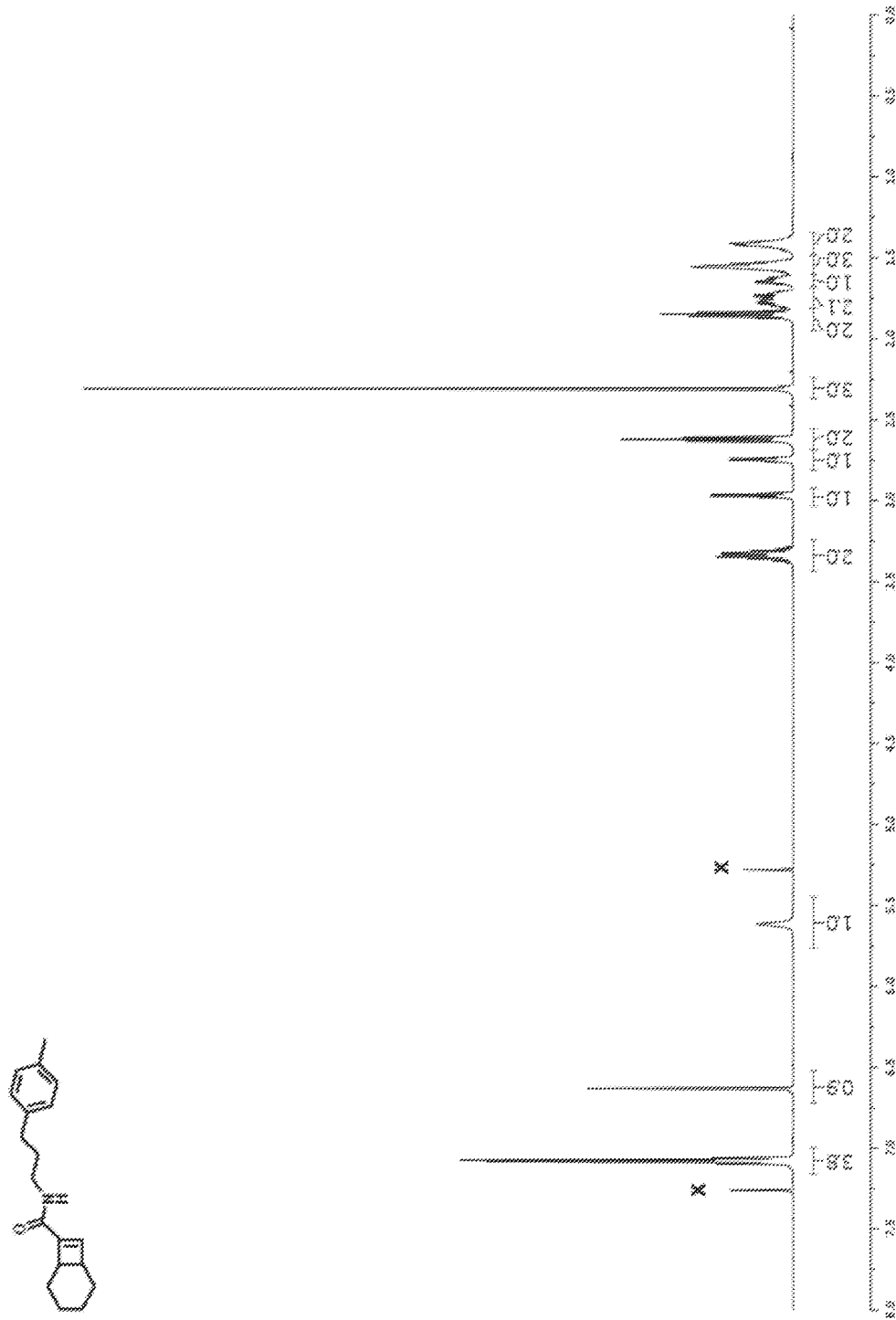
FIG. 17 shows $^1$H NMR spectrum of amide 1e in CDCl$_3$.
Figure 18:
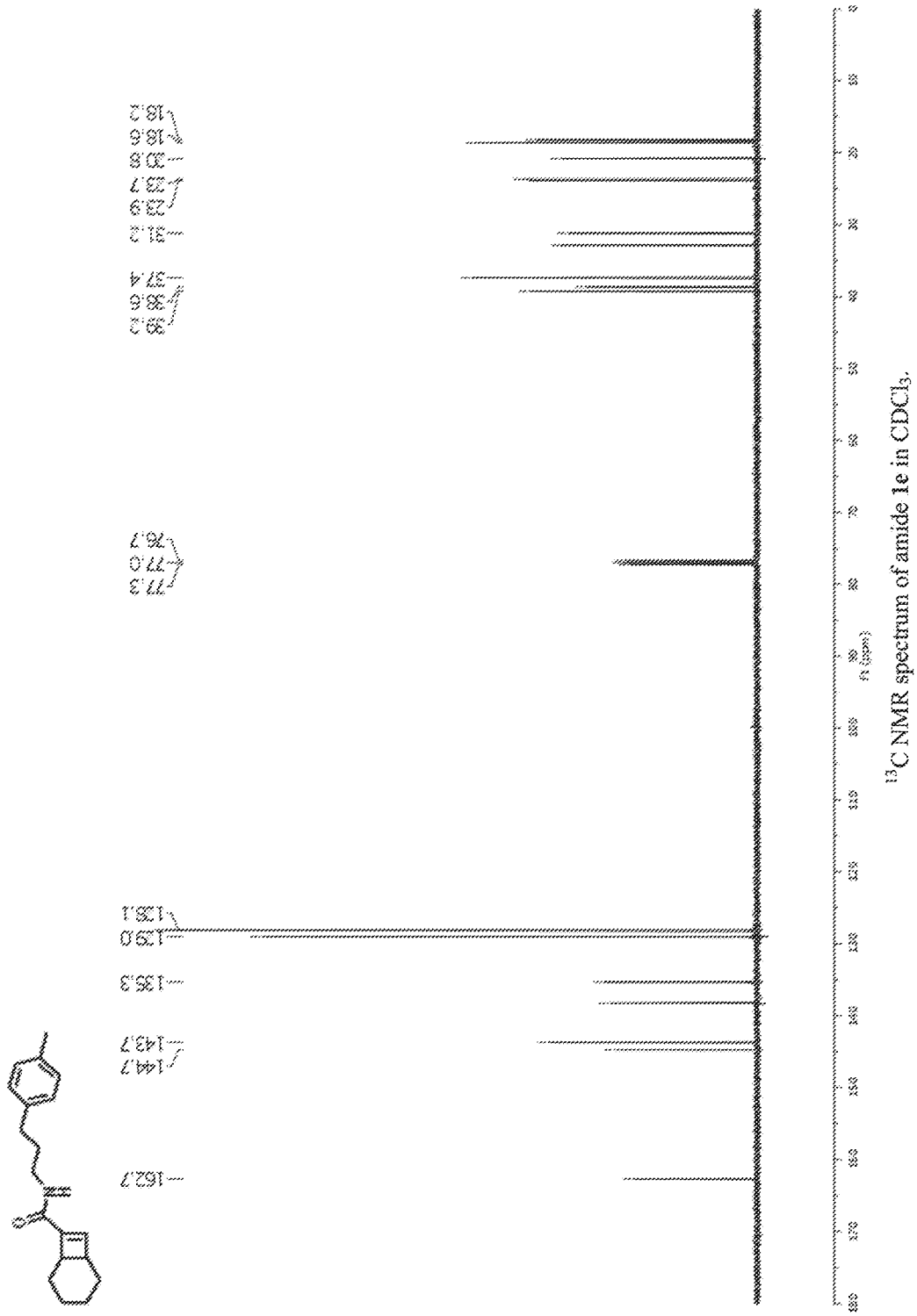
FIG. 18 shows the $^{13}$C NMR spectrum of amide 1e in CDCl$_3$.
Figure 19:
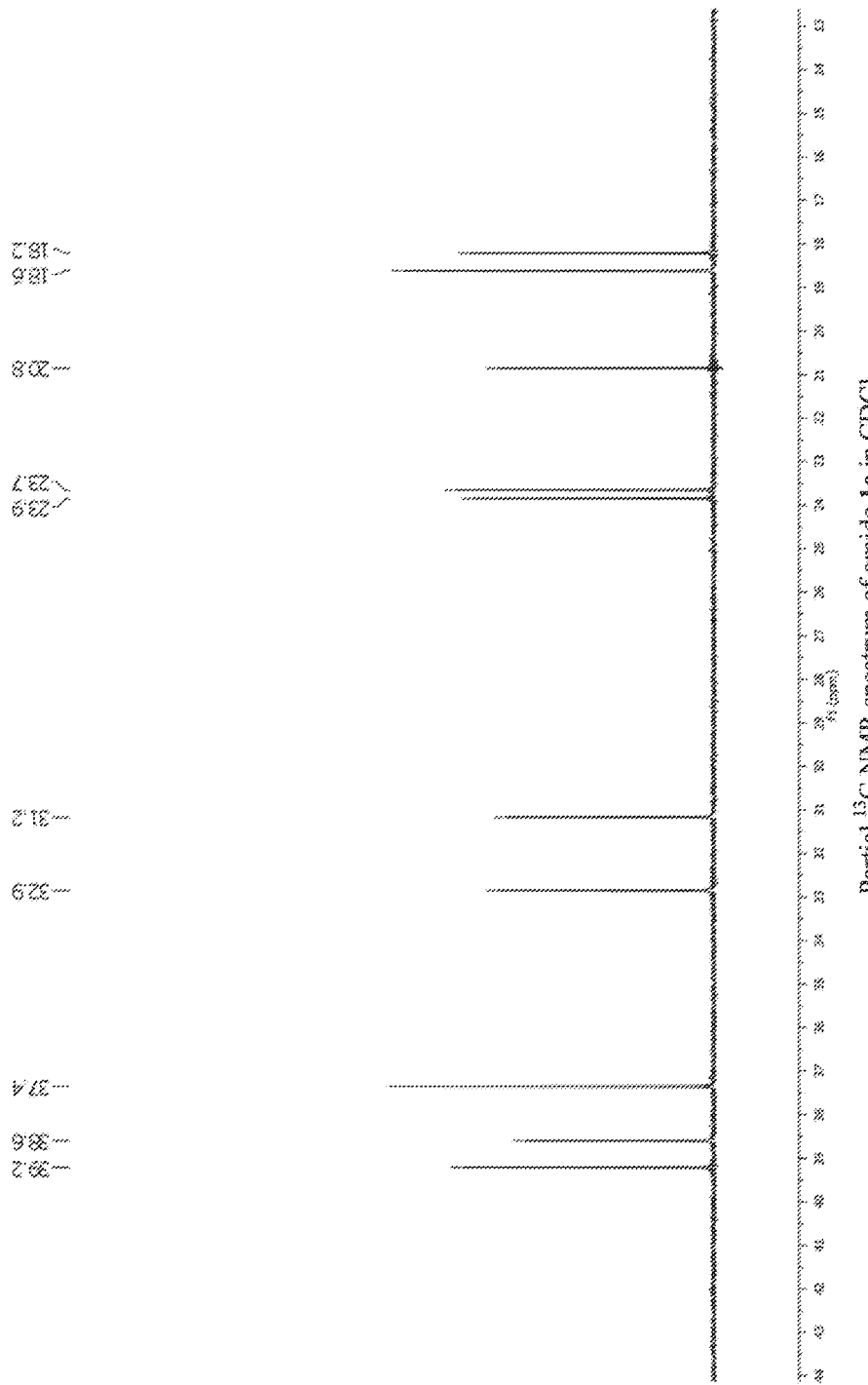
FIG. 19 shows the partial $^{13}$C NMR spectrum of amide 1e in CDCl$_3$.
Figure 20:
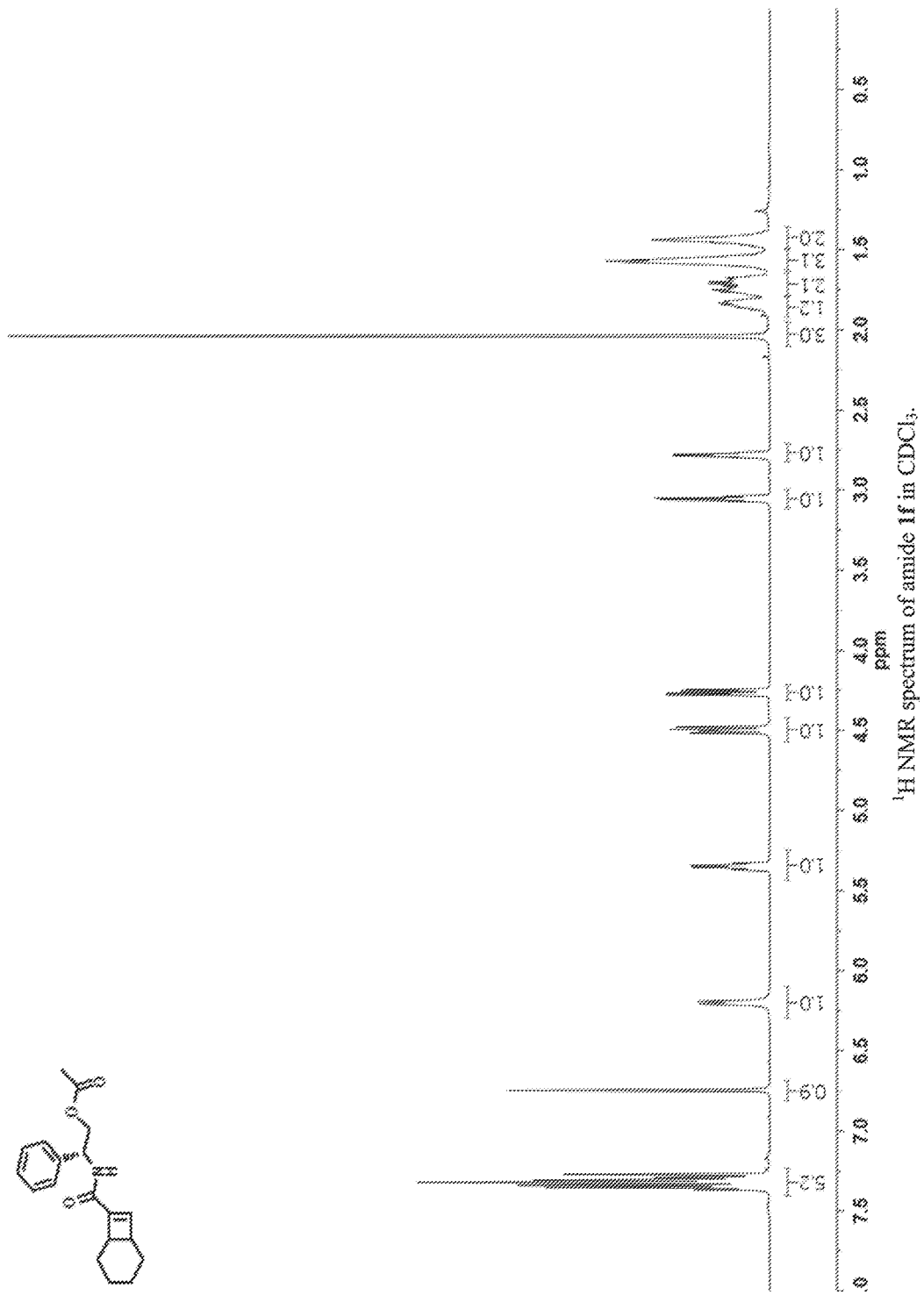
FIG. 20 shows the $^1$H NMR spectrum of amide 1f in CDCl$_3$.
Figure 21:
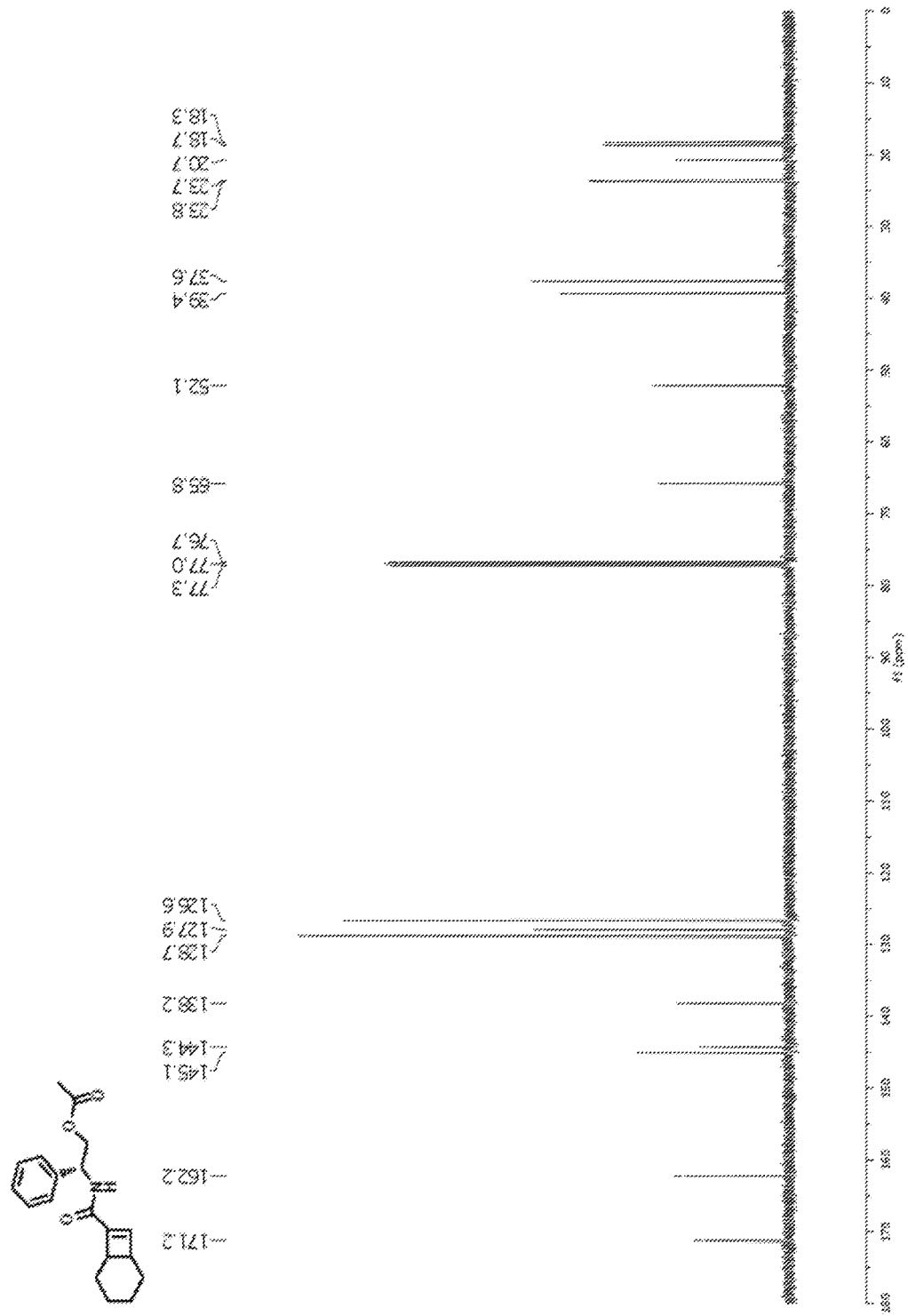
FIG. 21 shows the $^{13}$C NMR spectrum of amide 1f in CDCl$_3$.
Figure 22:
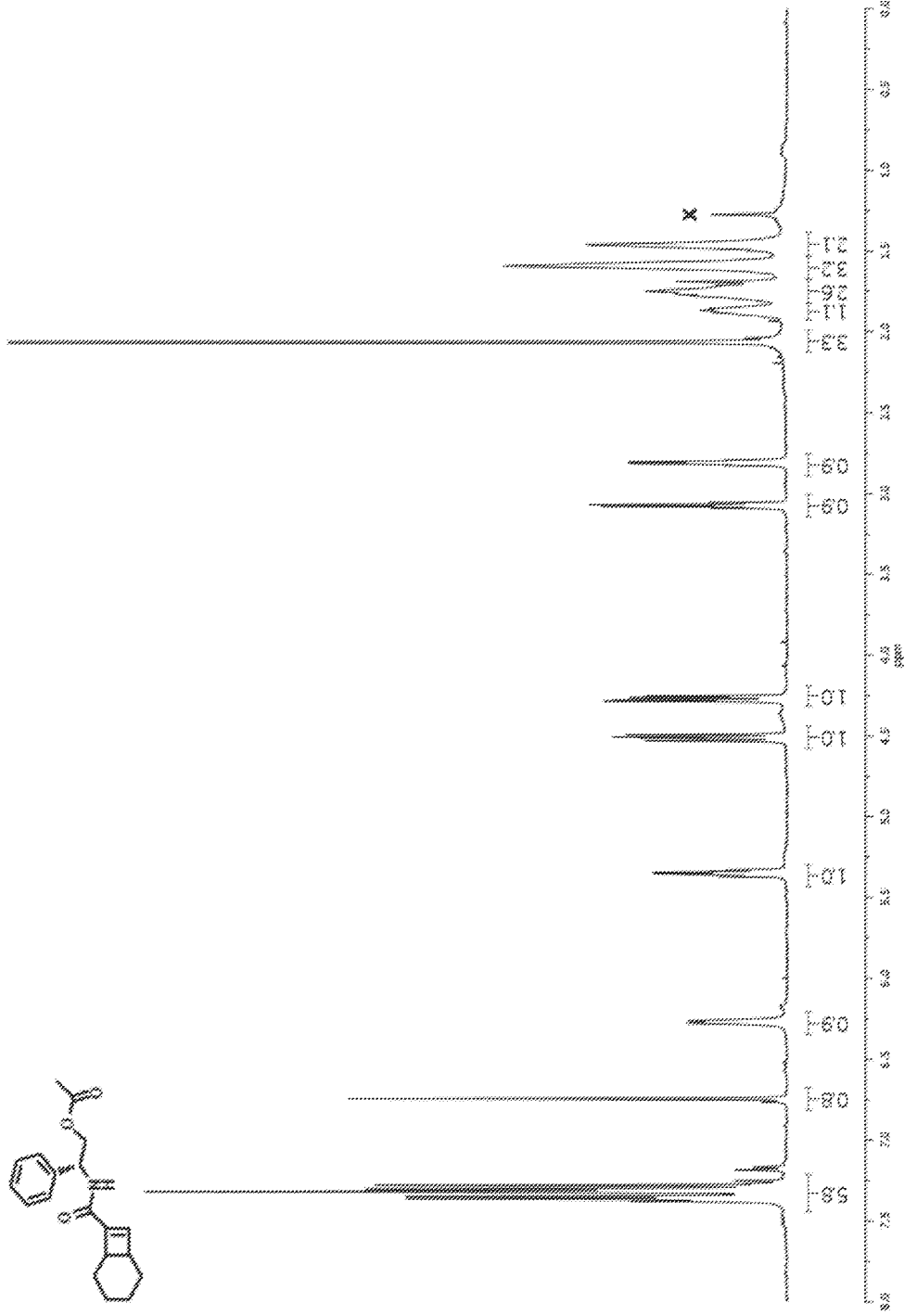
FIG. 22 shows the $^1$H NMR spectrum of amide 1f* in CDCl$_3$.
Figure 23:
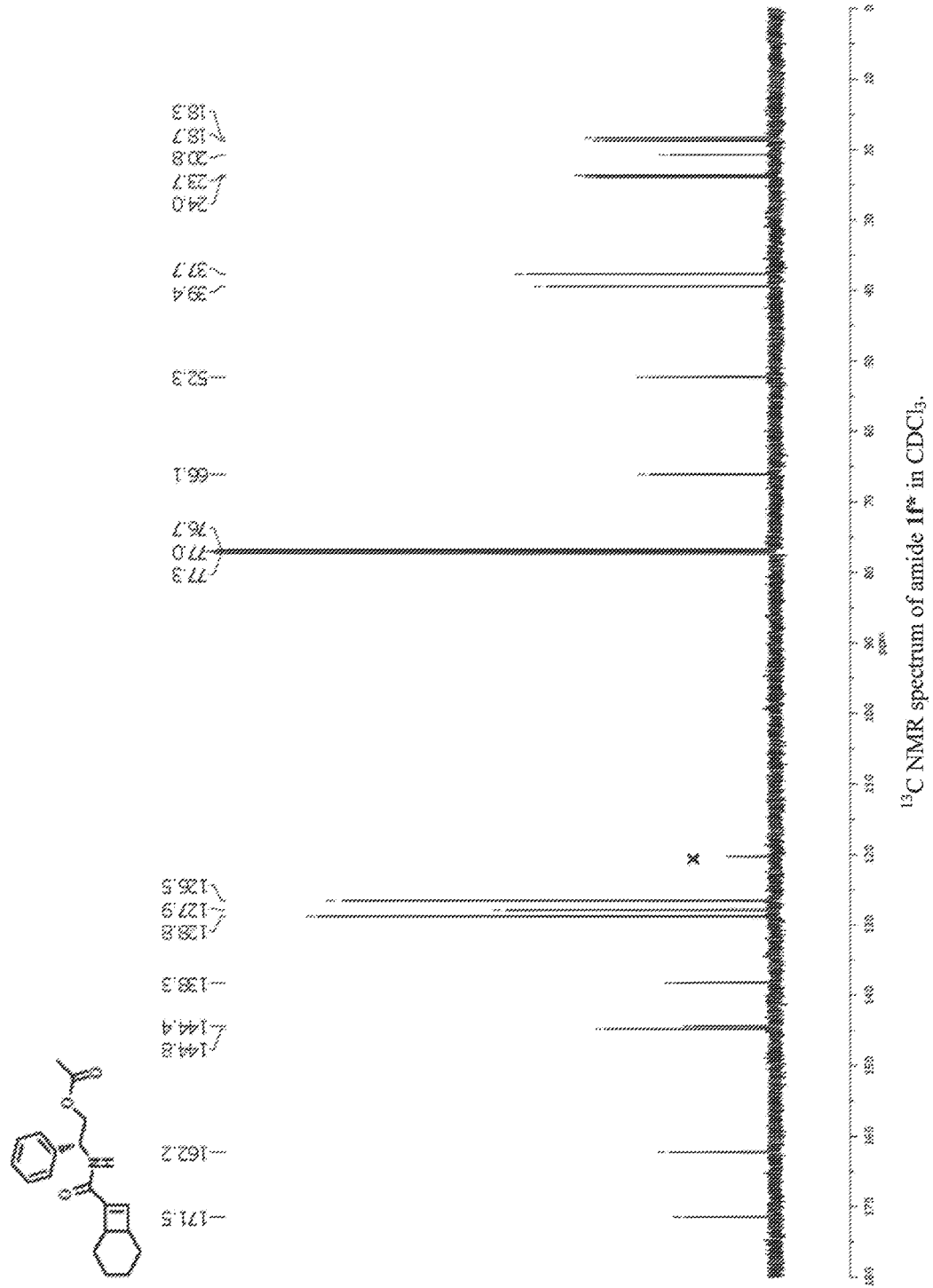
FIG. 23 shows the $^{13}$C NMR spectrum of amide 1f* in CDCl$_3$.
Figure 24:
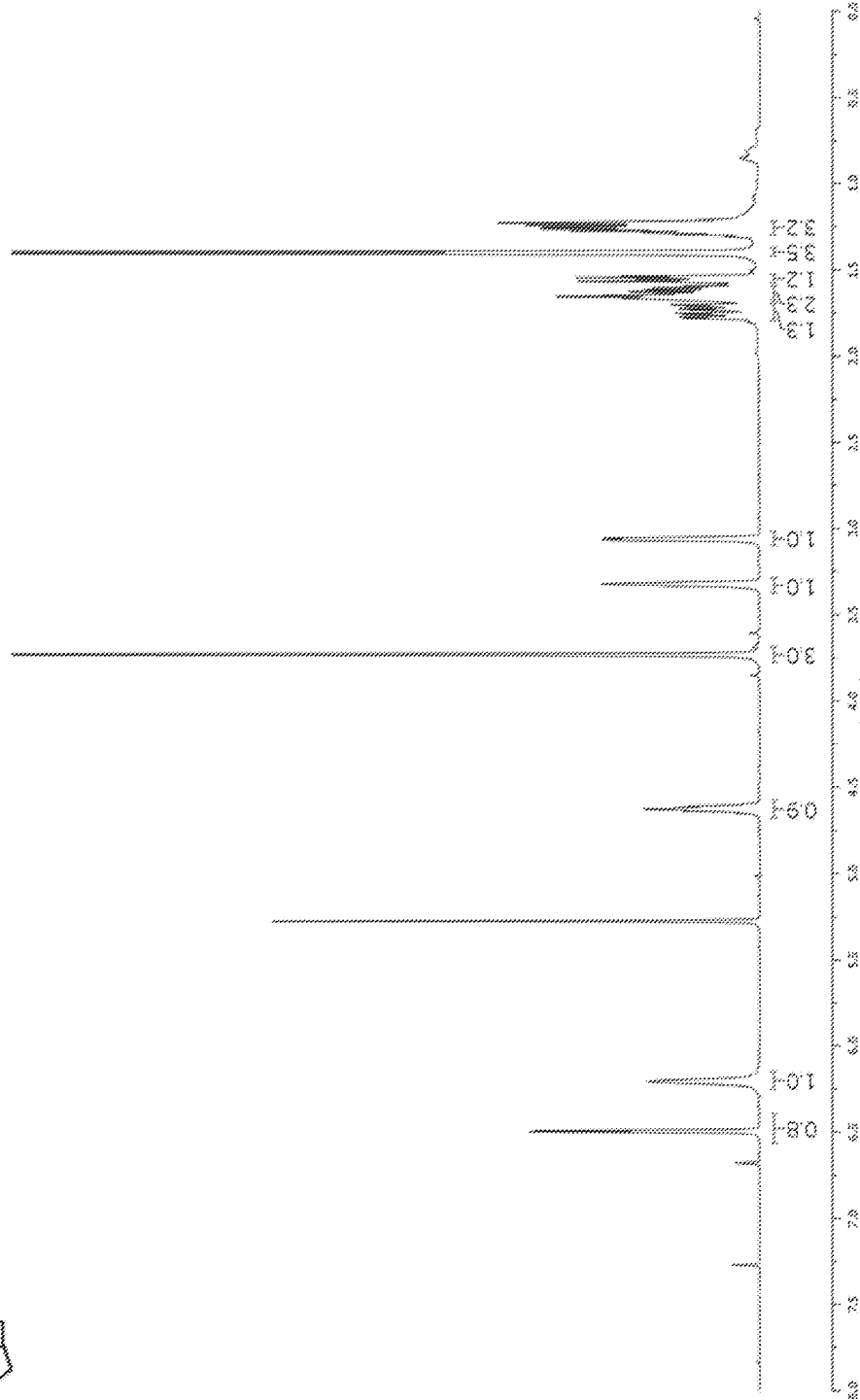
FIG. 24 shows the $^1$H NMR spectrum of amide 4 in CD$_2$Cl$_2$.
Figure 25:
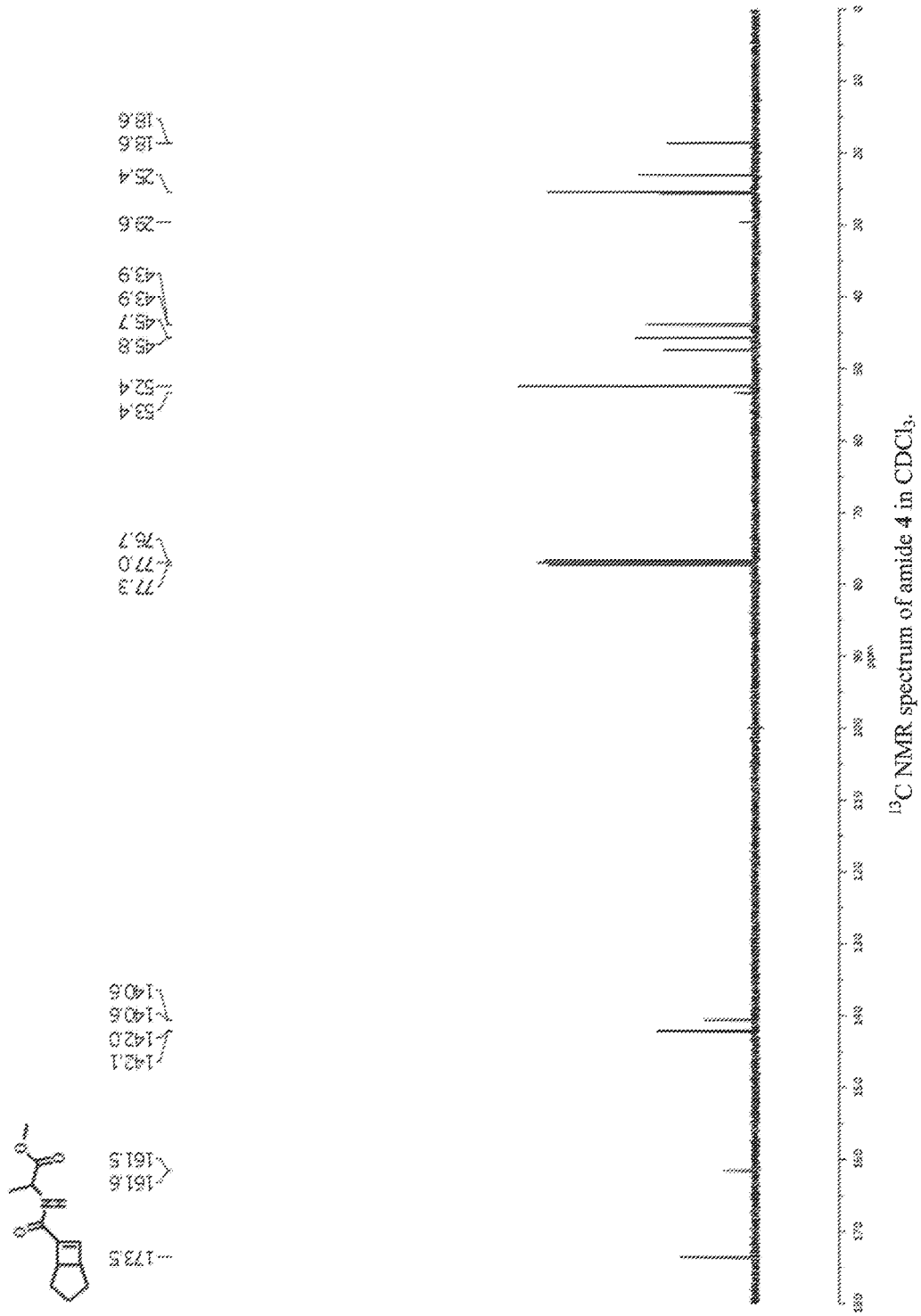
FIG. 25 shows the $^{13}$C NMR spectrum of amide 4 in CDCl$_3$.
Figure 26:
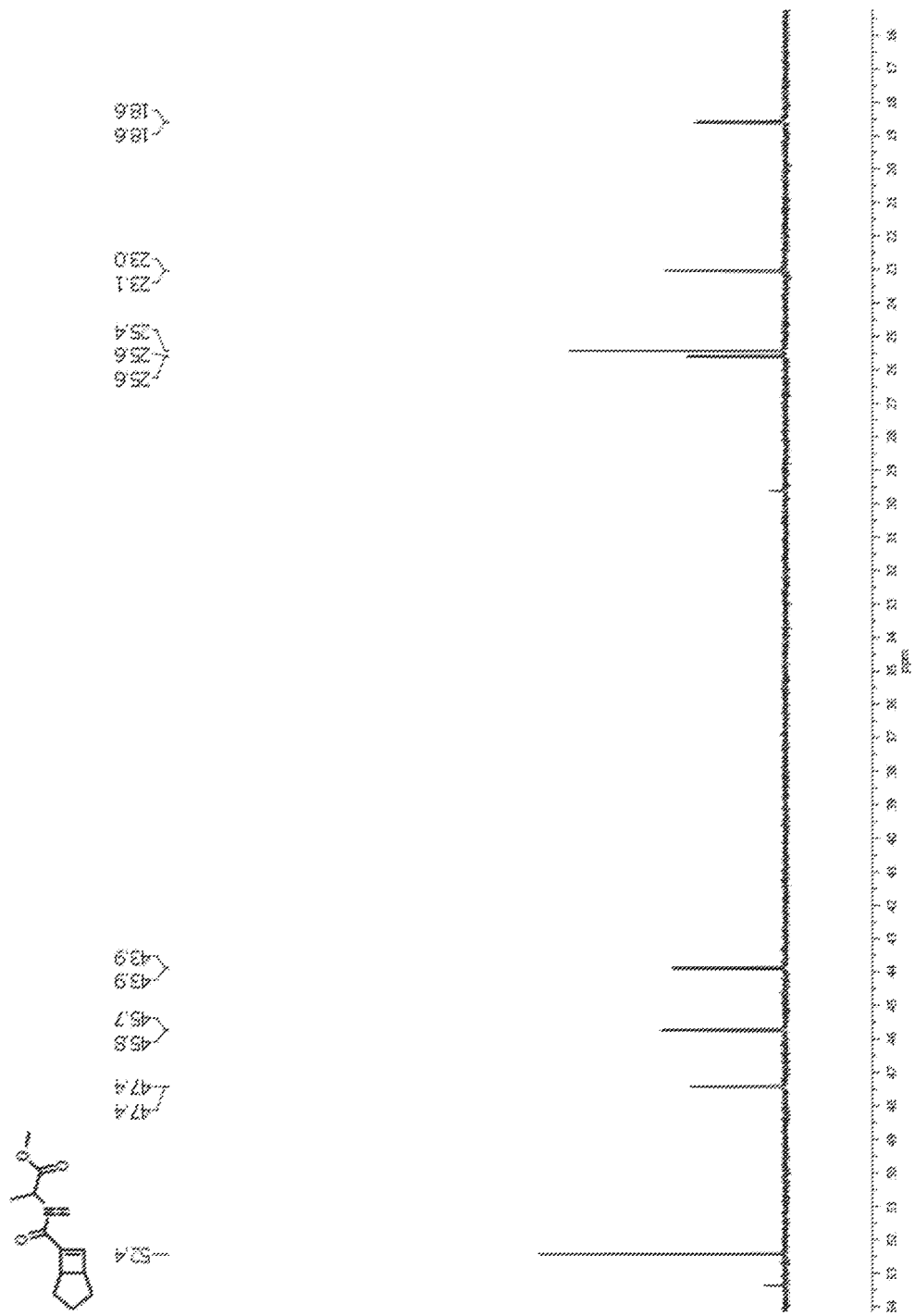
FIG. 26 shows the partial $^{13}$C NMR spectrum of amide 4 in CDCl$_3$.
Figure 29:
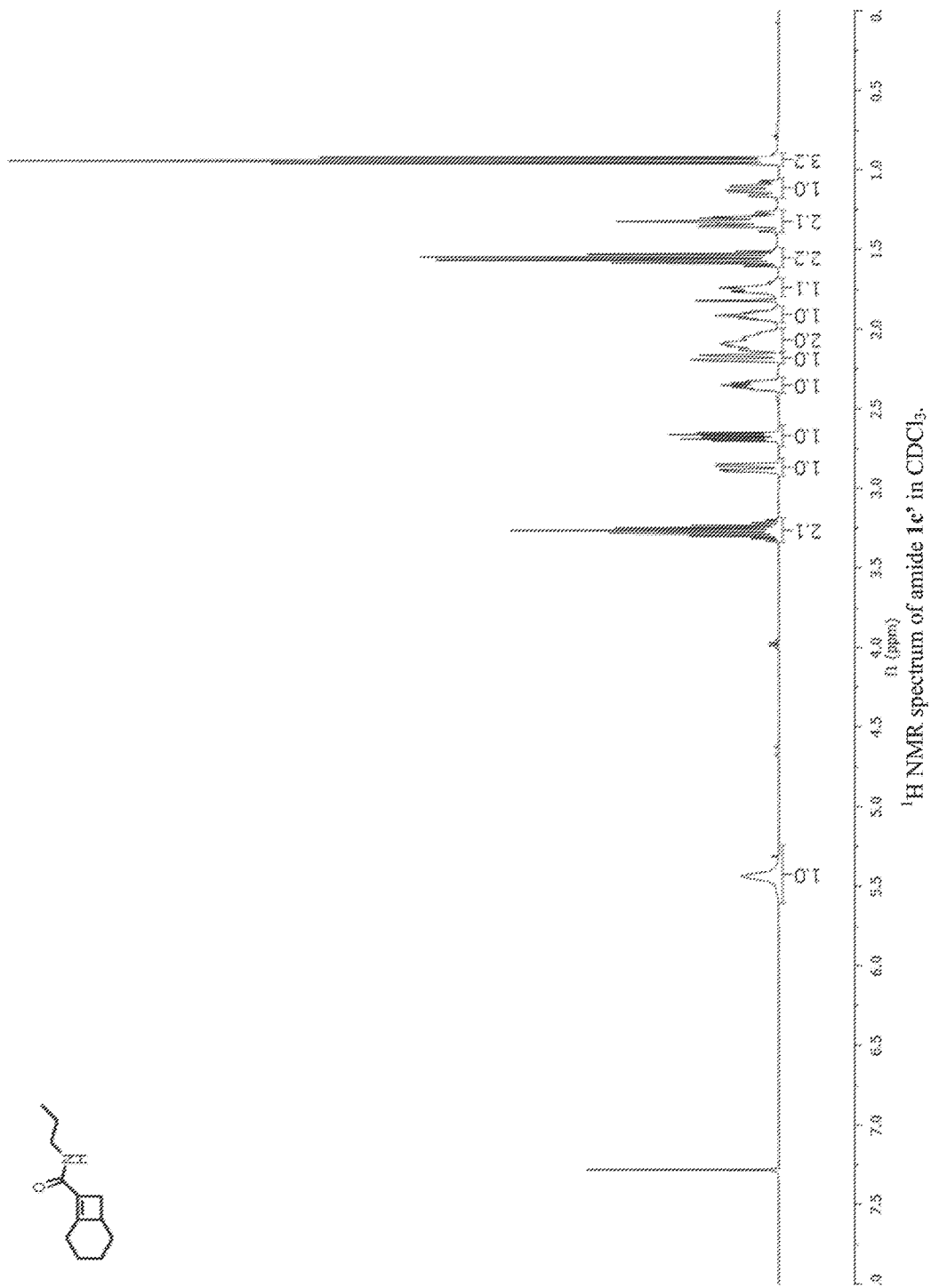
FIG. 29 shows the $^1$H NMR spectrum of amide 1c' in CDCl$_3$.
Figure 30:
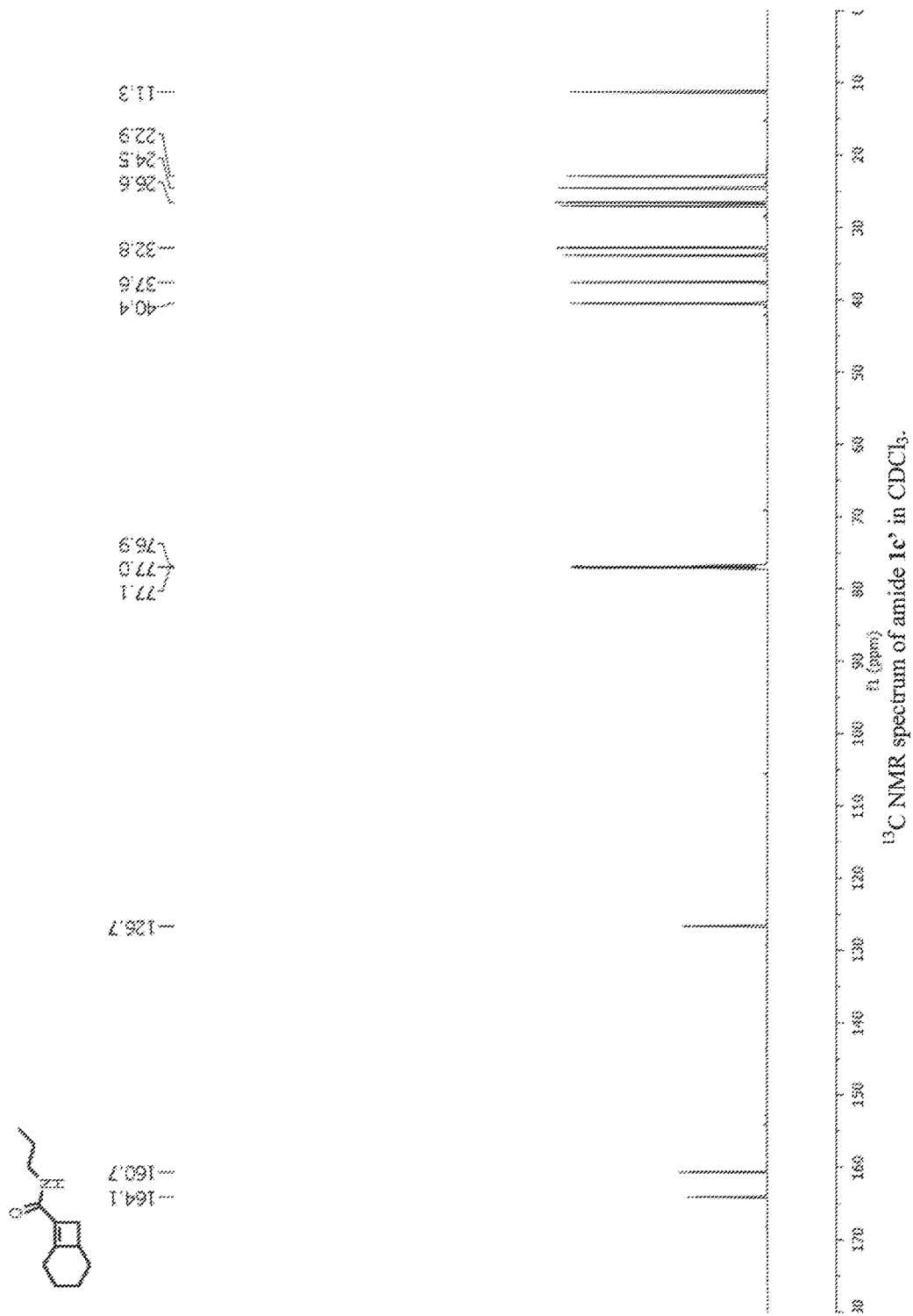
FIG. 30 shows the $^{13}$C NMR spectrum of amide 1c' in CDCl$_3$.
Figure 31:
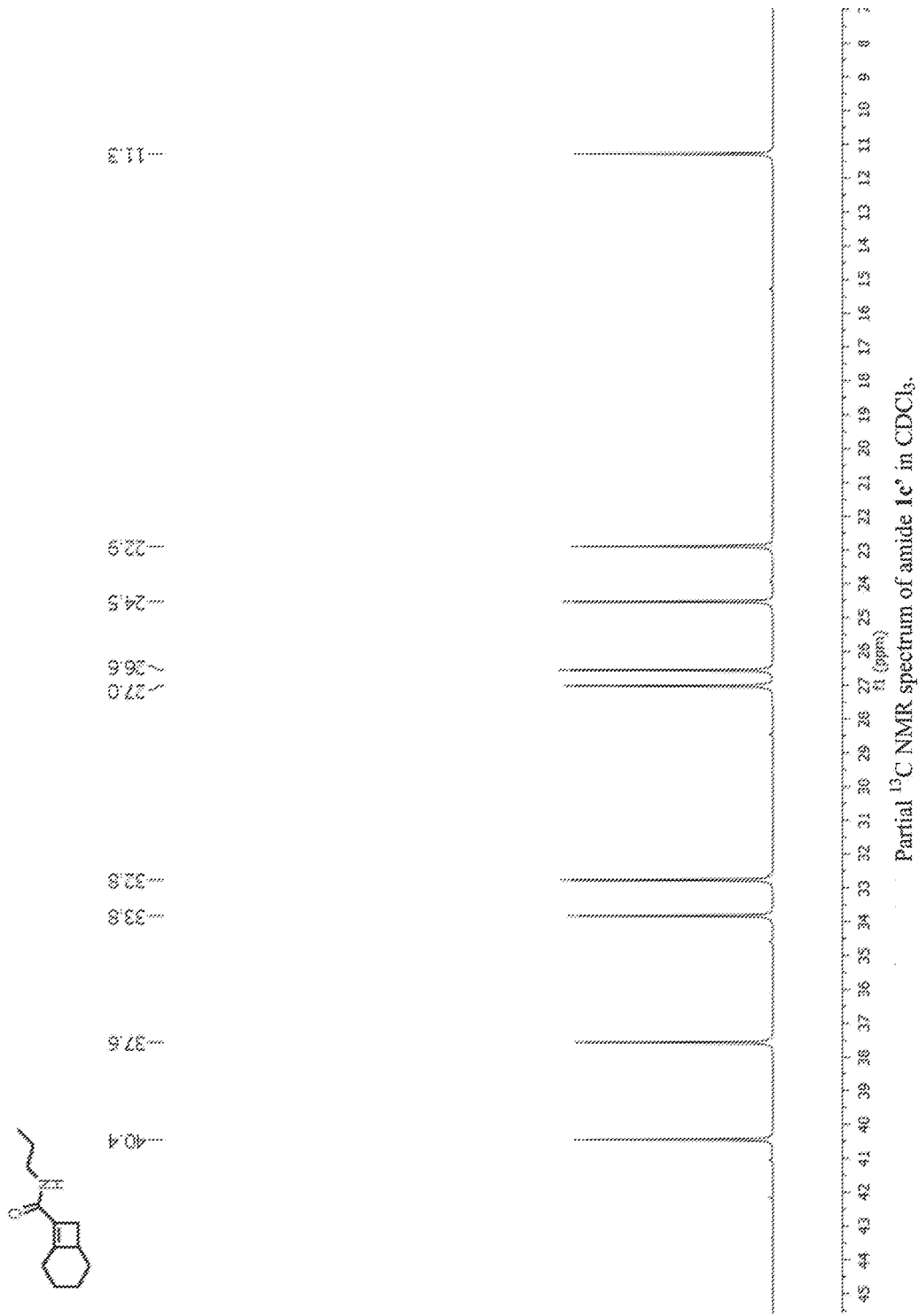
FIG. 31 shows the partial $^{13}$C NMR spectrum of amide 1c' in CDCl$_3$.
Figure 34:
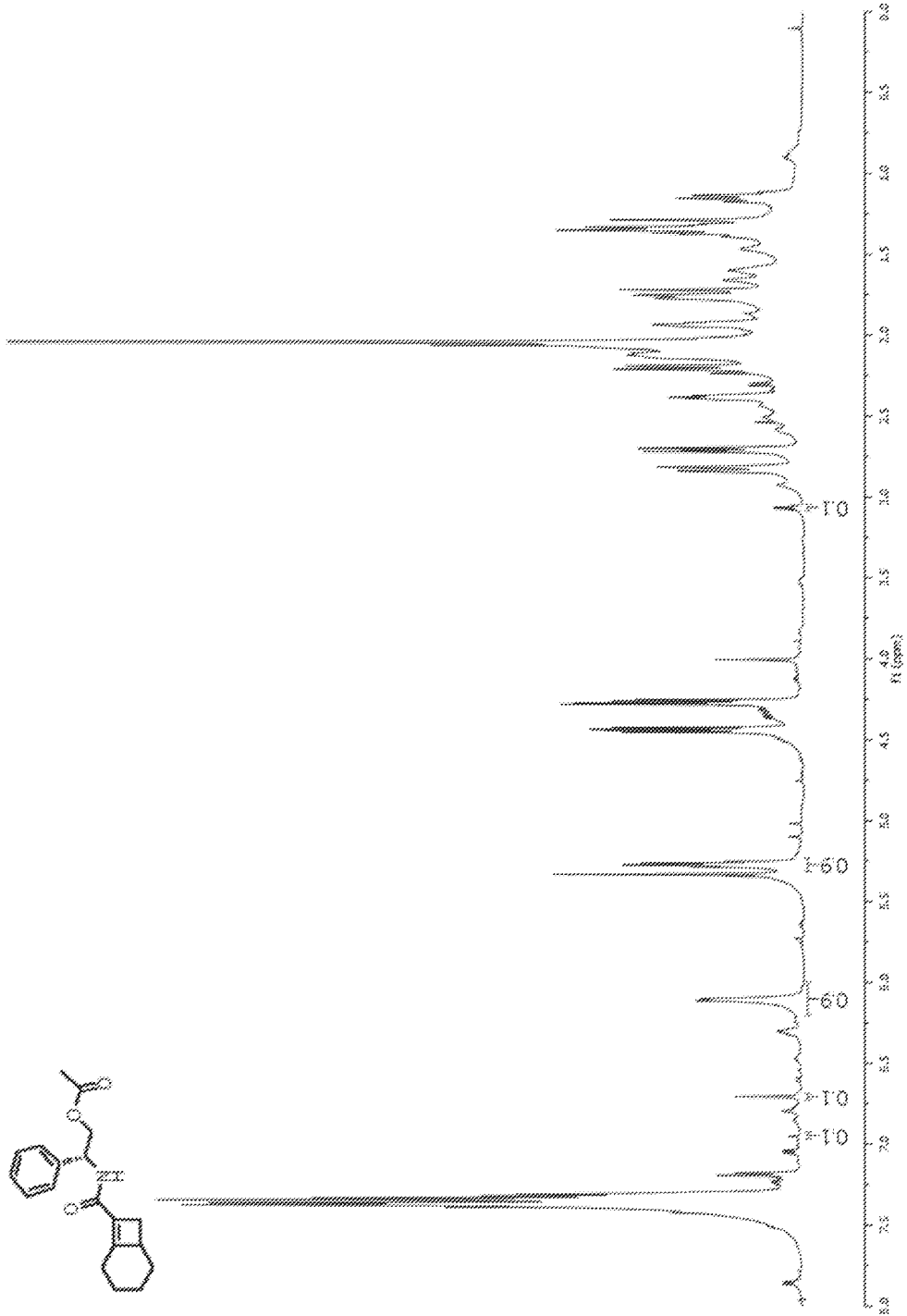
FIG. 34 shows the $^1$H NMR spectrum of amide 1f and alkylidene 2 in CD$_2$Cl$_2$ with 90% 1f isomerized to 1f.
Figure 35:
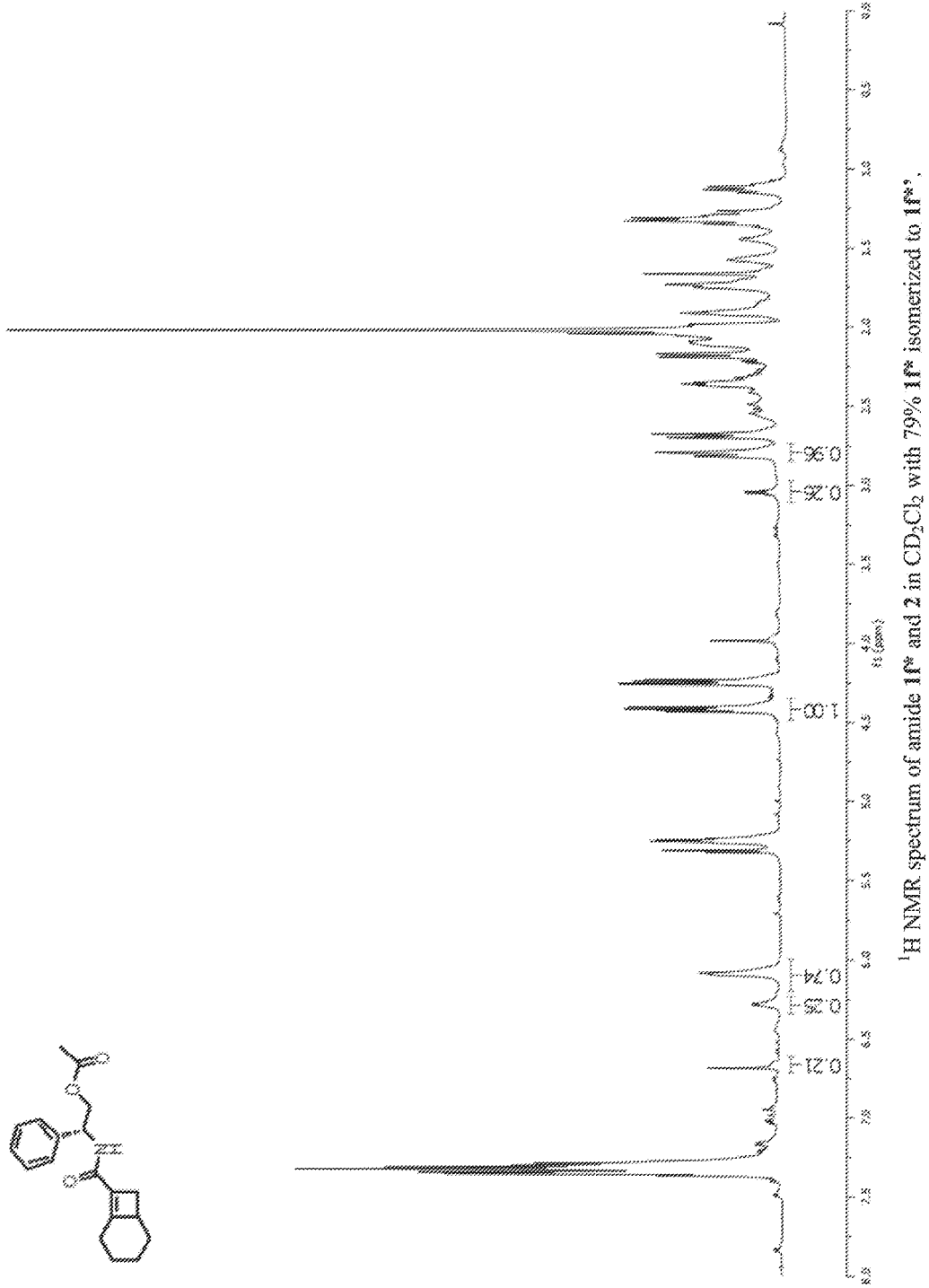
FIG. 35 shows the $^1$H NMR spectrum of amide 1f* and 2 in CD$_2$Cl$_2$ with 79% 1f* isomerized to 1f*'.
Figure 36:
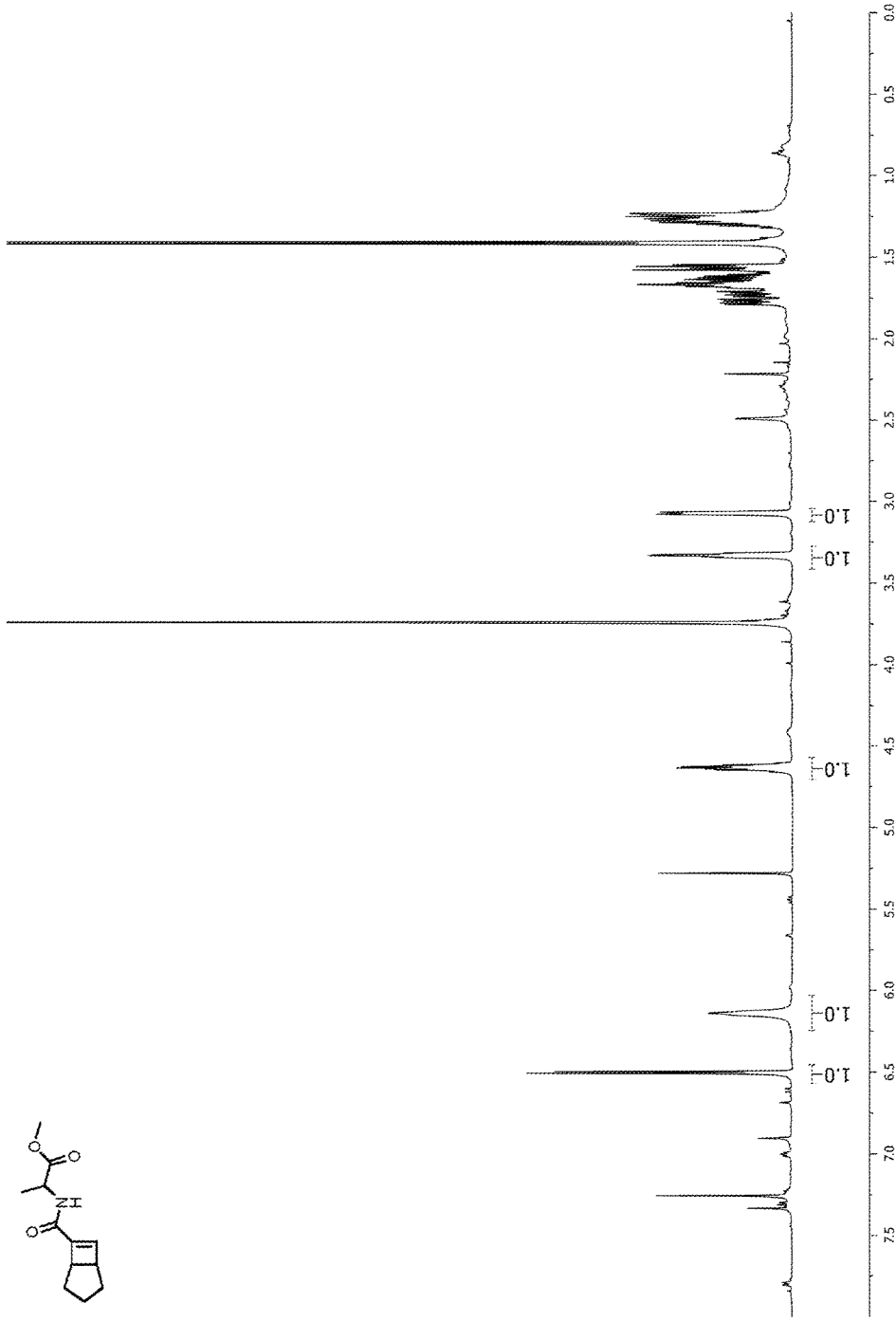
FIG. 36 shows the $^1$H NMR spectrum of amide 4 and alkylidene 2 in CD$_2$Cl$_2$. No isomerization is observed.
Figure 37:
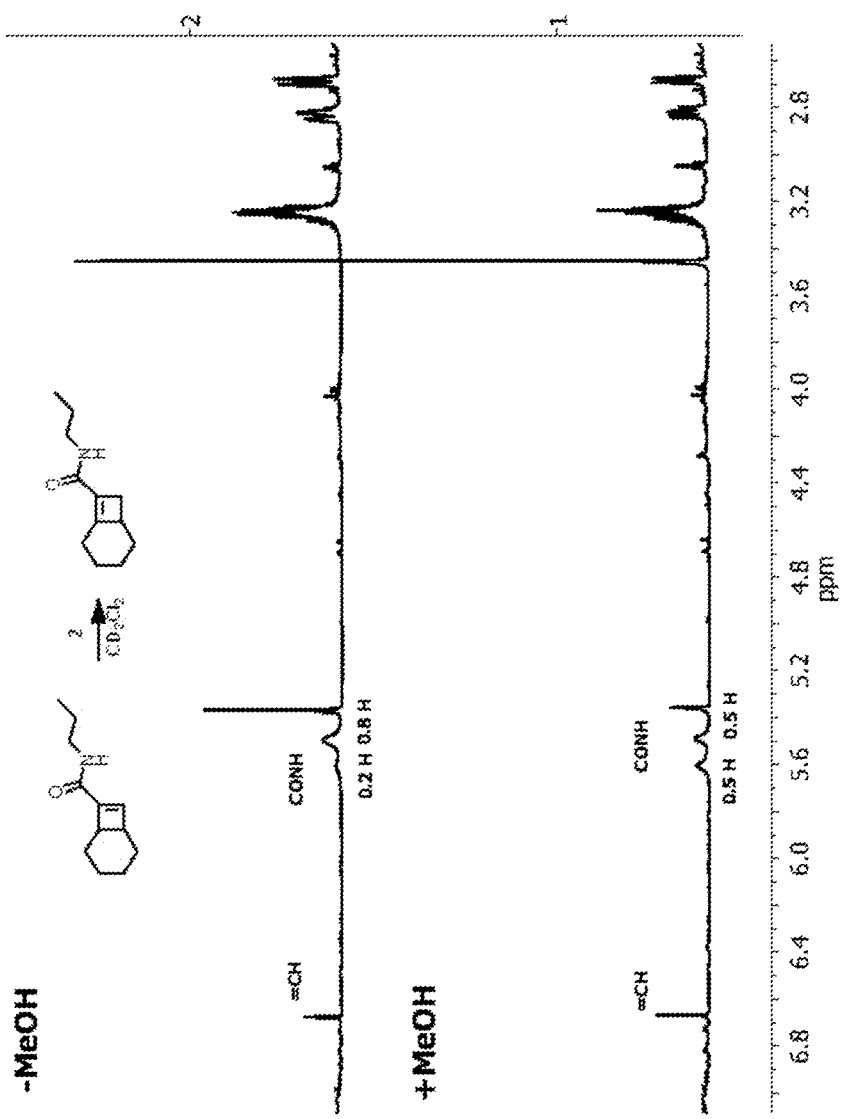
FIG. 37 shows the isomerization of 1c with and without 50 µL of MeOH in the presence of 2 in CD$_2$Cl$_2$. Spectra were obtained 1 hour after mixing monomer with catalyst.
Figure 38:
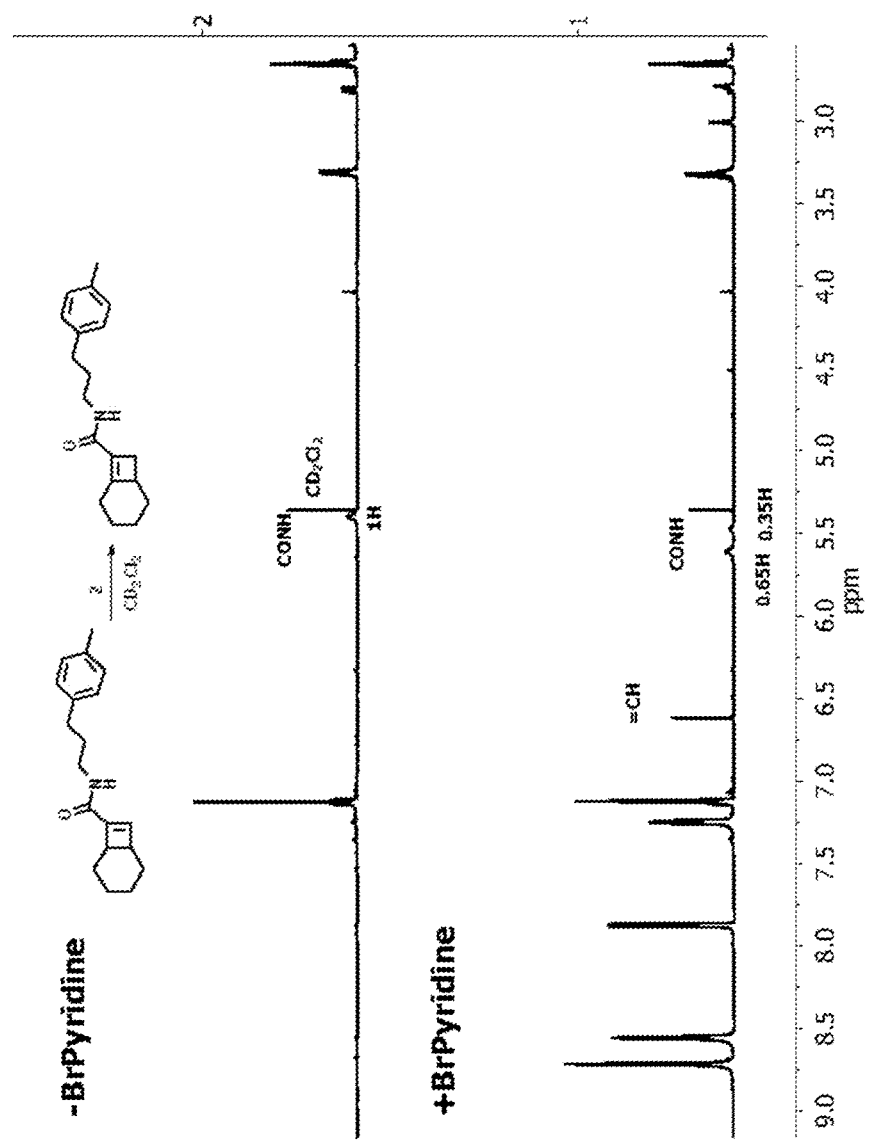
FIG. 38 shows the isomerization of 1e with and without 50 equiv of 3-bromopyridine in the presence of 2 in CD$_2$Cl$_2$. Spectra were obtained 16 hours after mixing monomer and catalyst.
Figure 39:
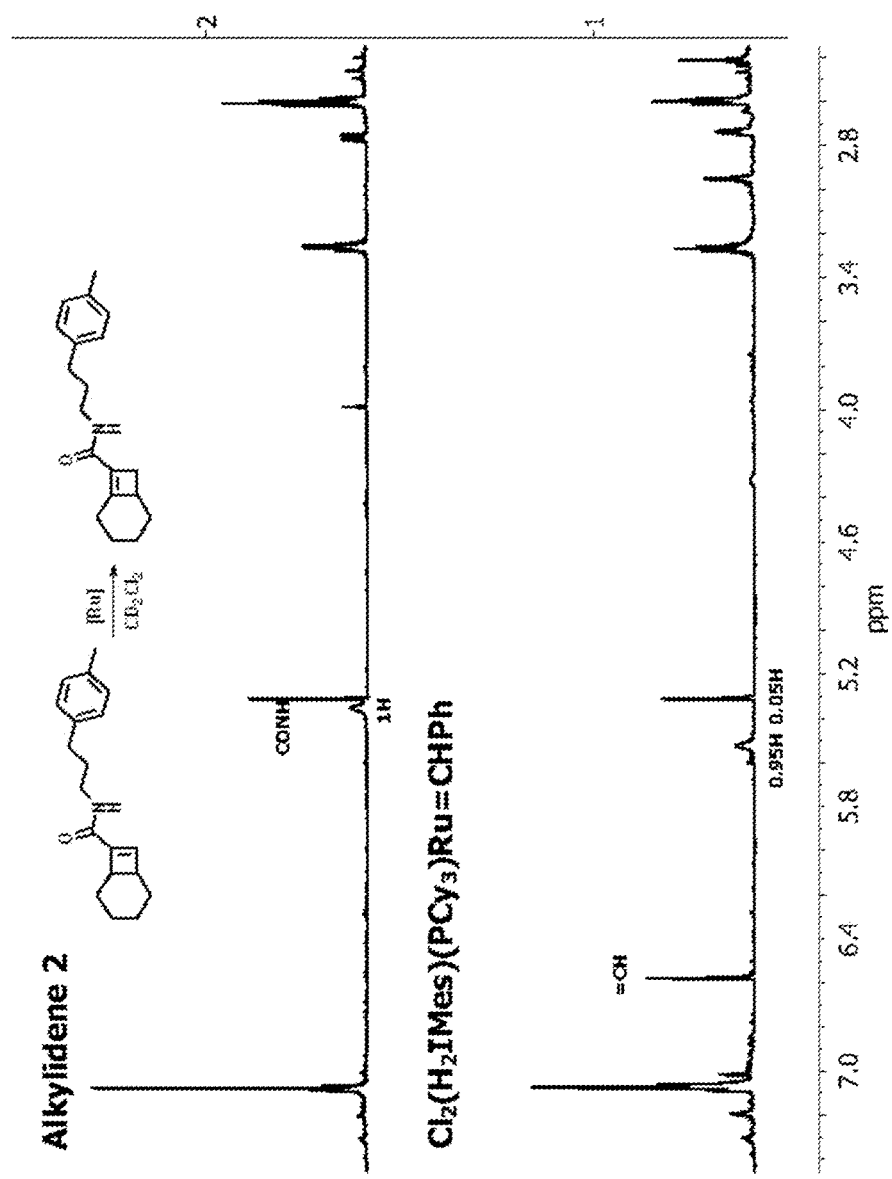
FIG. 39 shows the isomerization of 1e in the presence of Cl$_2$(H$_2$IMes)(PCy$_3$)Ru=CHPh (10 mol %) or alkylidene 2 (10 mol %) in CD$_2$Cl$_2$. Spectra were obtained 14 hours after mixing monomer and catalyst.
Figure 41:
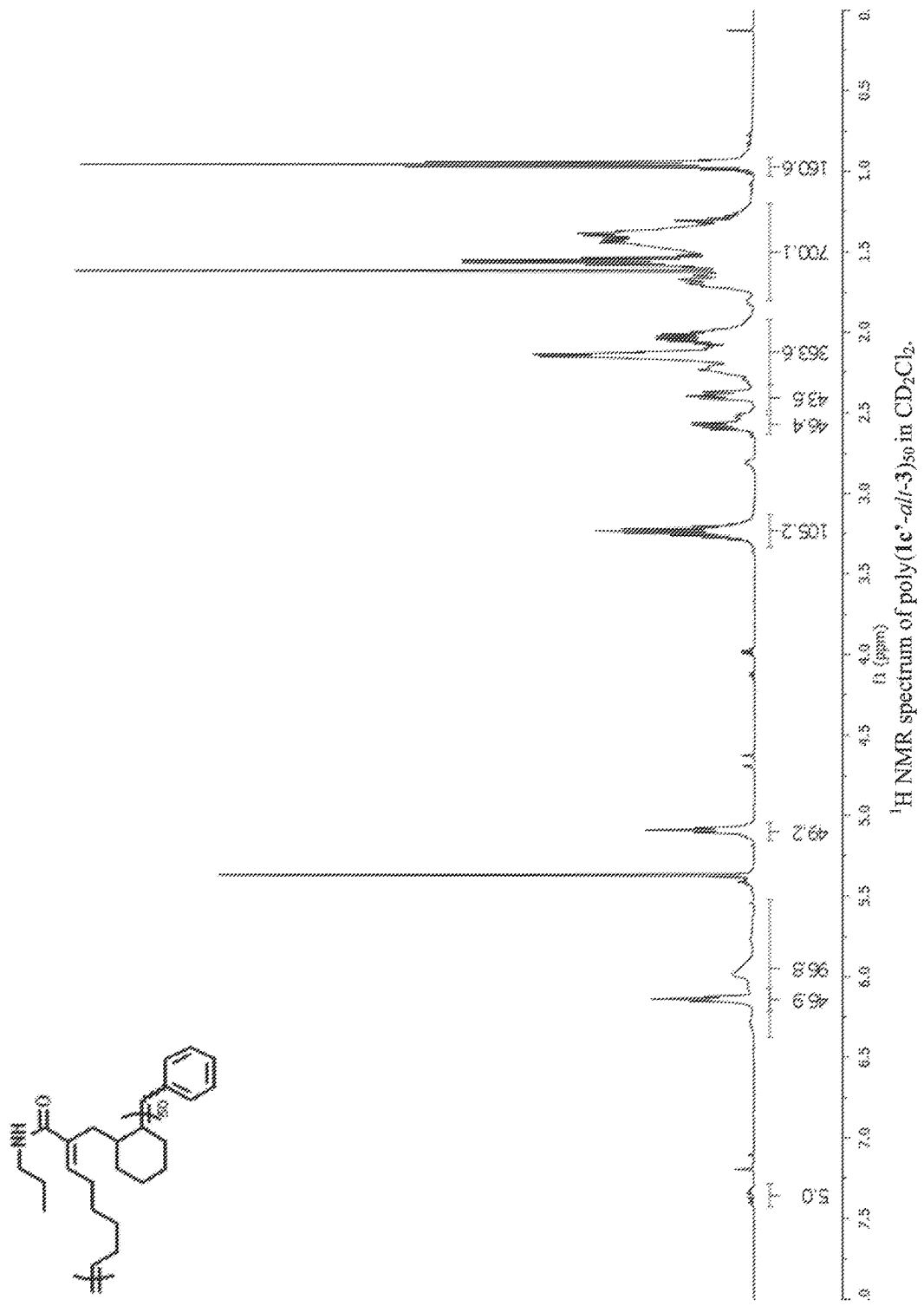
FIG. 41 shows the $^1$H NMR spectrum of poly(1c'-alt-3)$_{50}$ in CD$_2$Cl$_2$.
Figure 43:
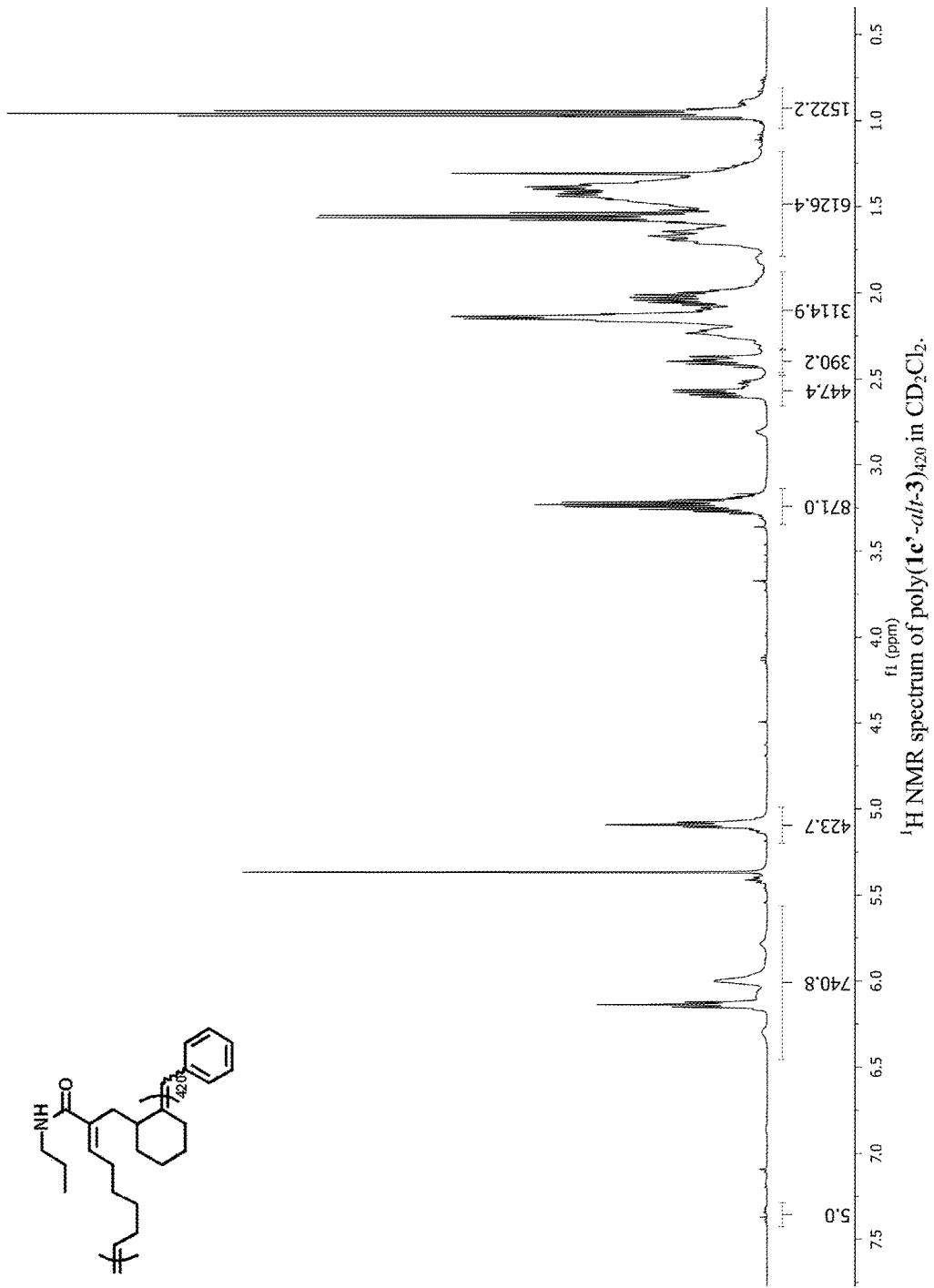
FIG. 43 shows the $^1$H NMR spectrum of poly(1c'-alt-3)$_{420}$ in CD$_2$Cl$_2$.
Figure 44:
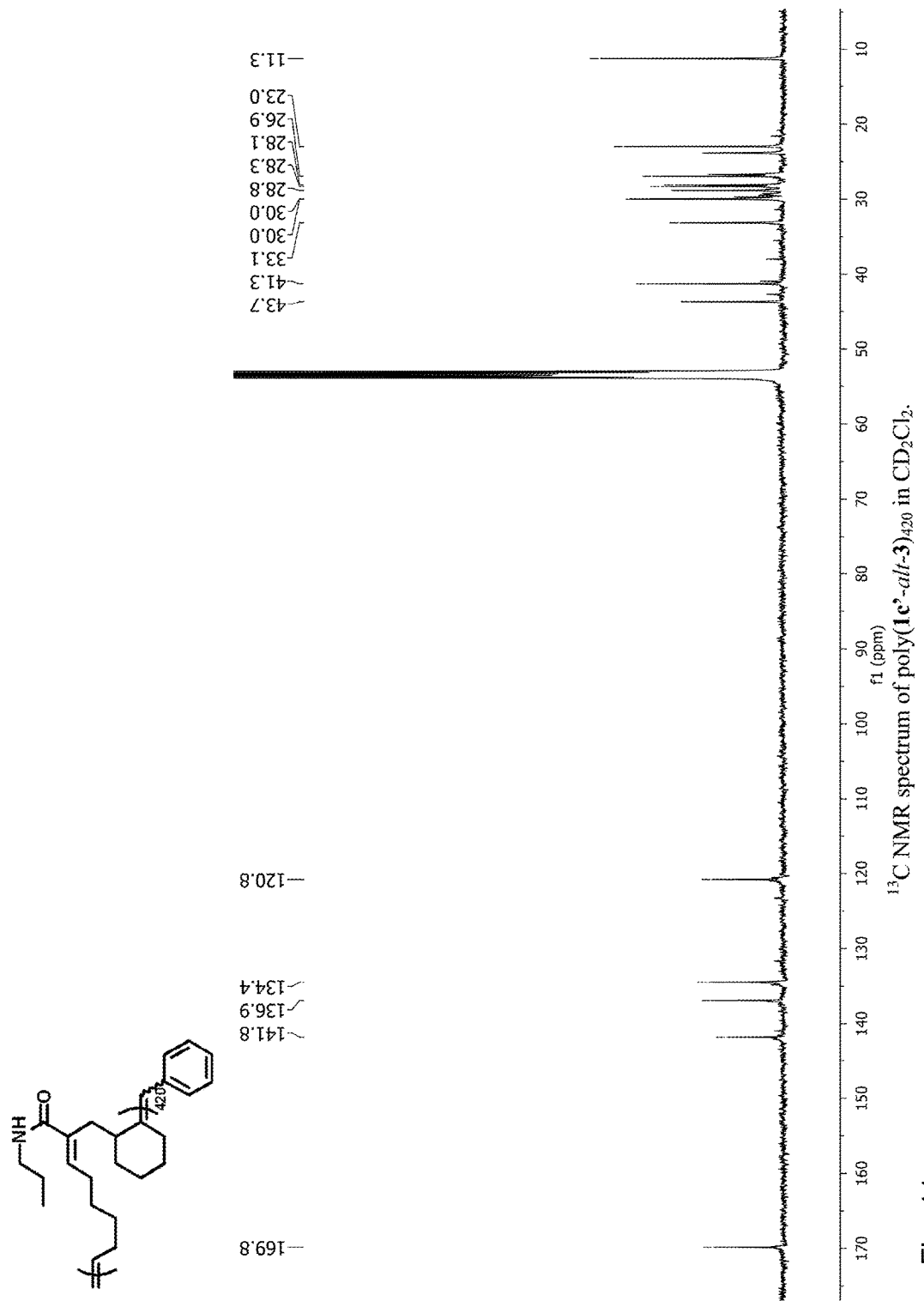
FIG. 44 shows the $^{13}$C NMR spectrum of poly(1c'-alt-3)$_{420}$ in CD$_2$Cl$_2$.
Figure 45:
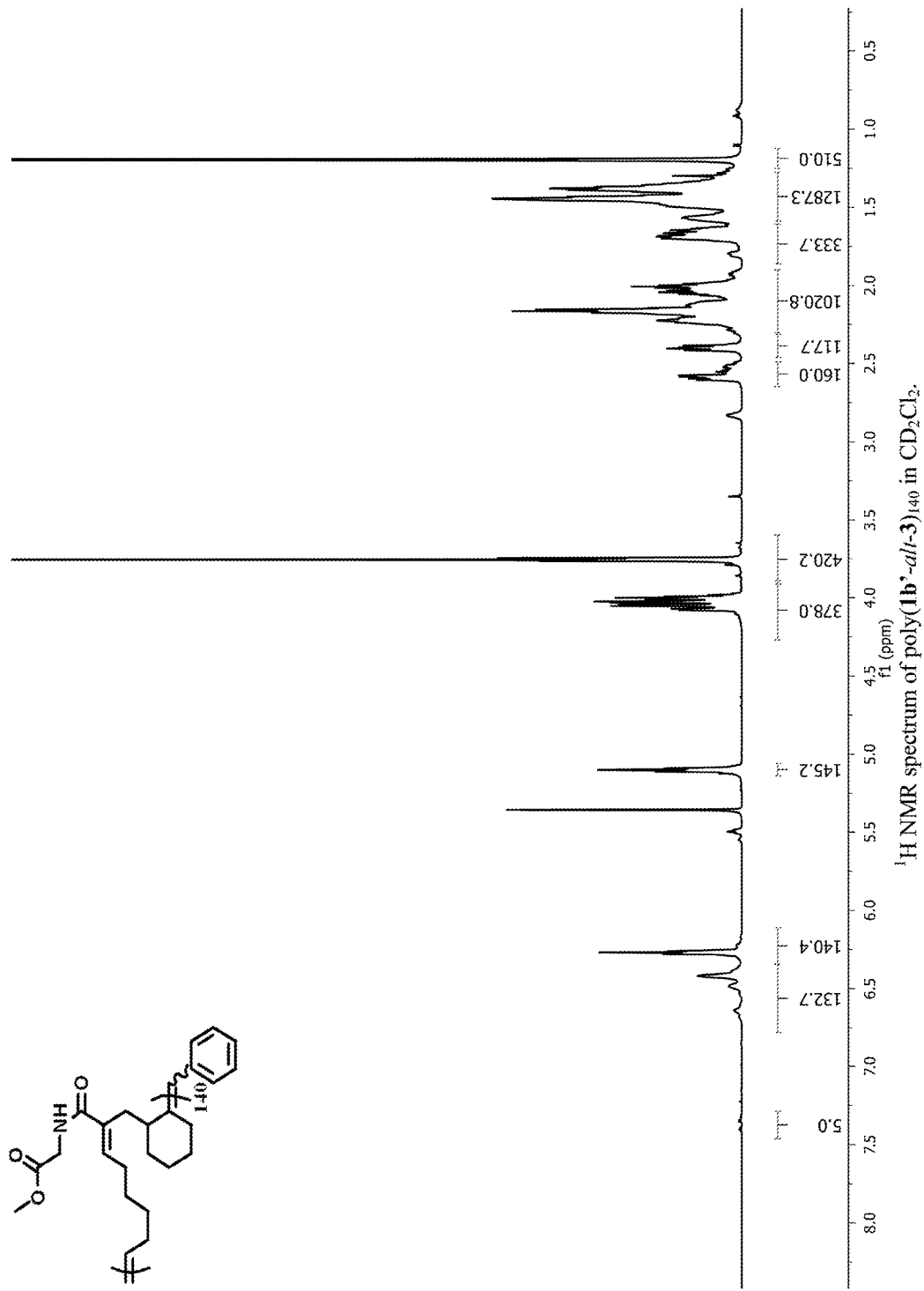
FIG. 45 shows the $^1$H NMR spectrum of poly(1b'-alt-3)$_{140}$ in CD$_2$Cl$_2$.
Figure 46:
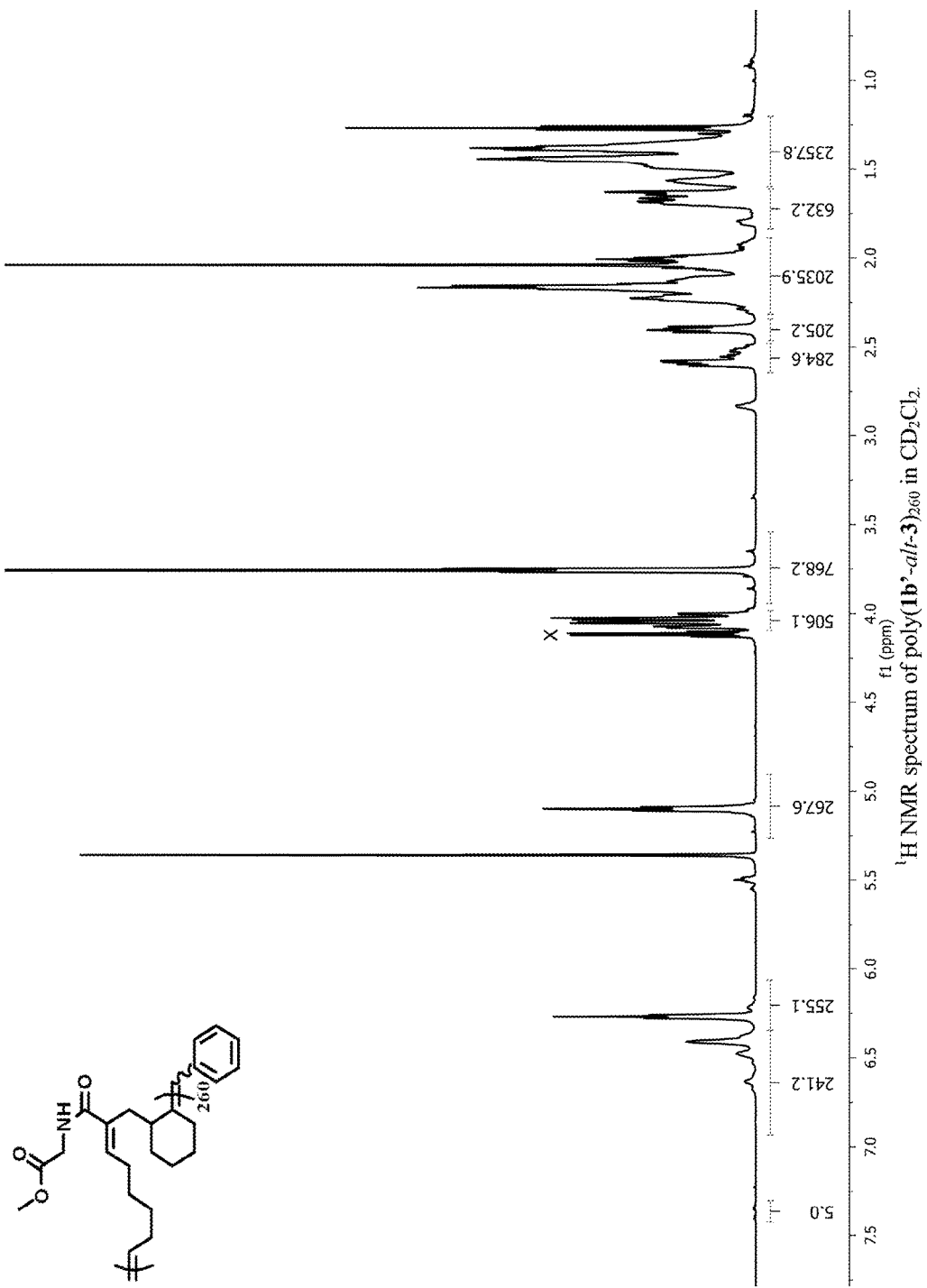
FIG. 46 shows the $^1$H NMR spectrum of poly(1b'-alt-3)$_{260}$ in CD$_2$Cl$_2$.
Figure 47:
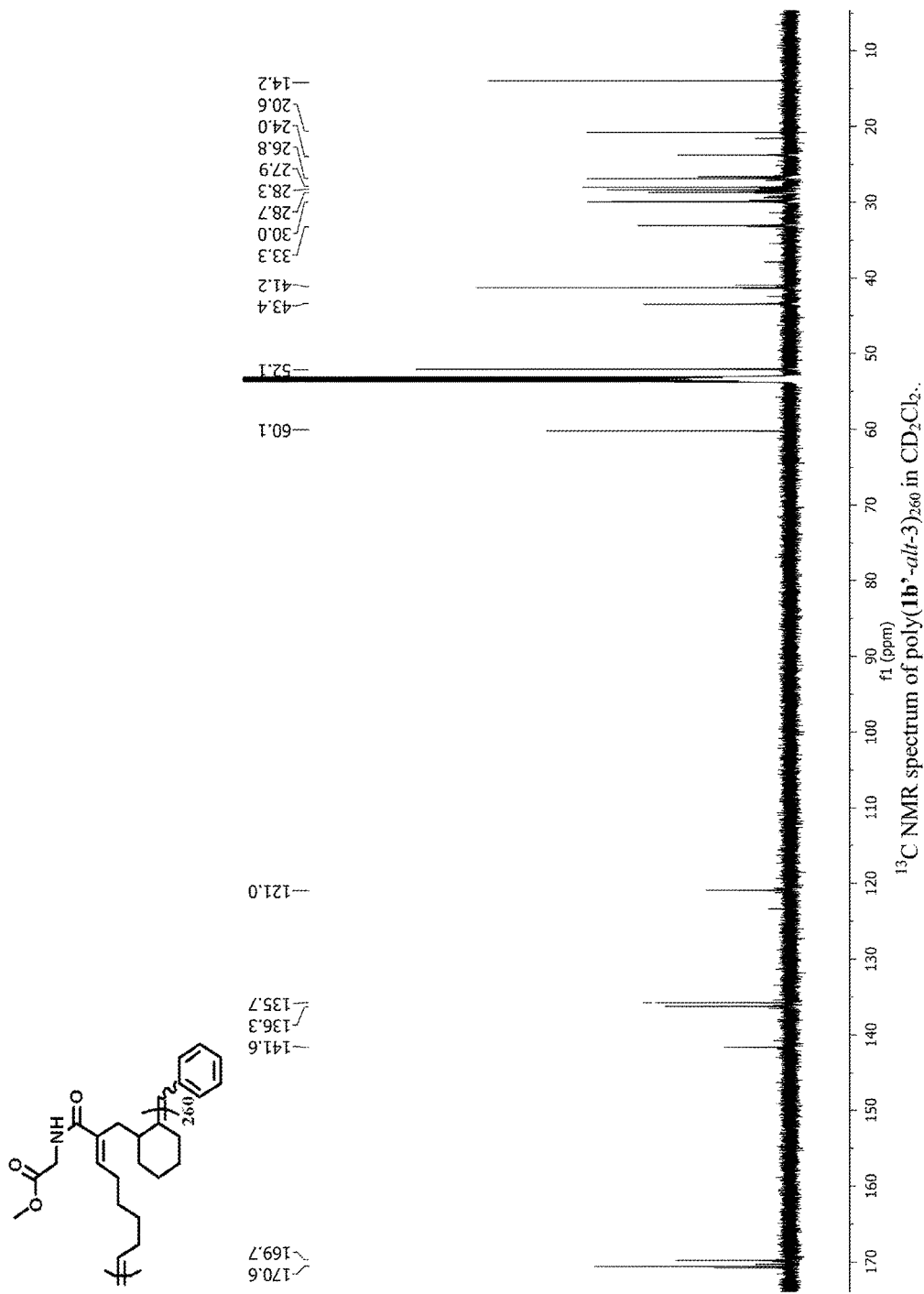
FIG. 47 shows the $^{13}$C NMR spectrum of poly(1b'-alt-3)$_{260}$ in CD$_2$Cl$_2$.
Figure 48:
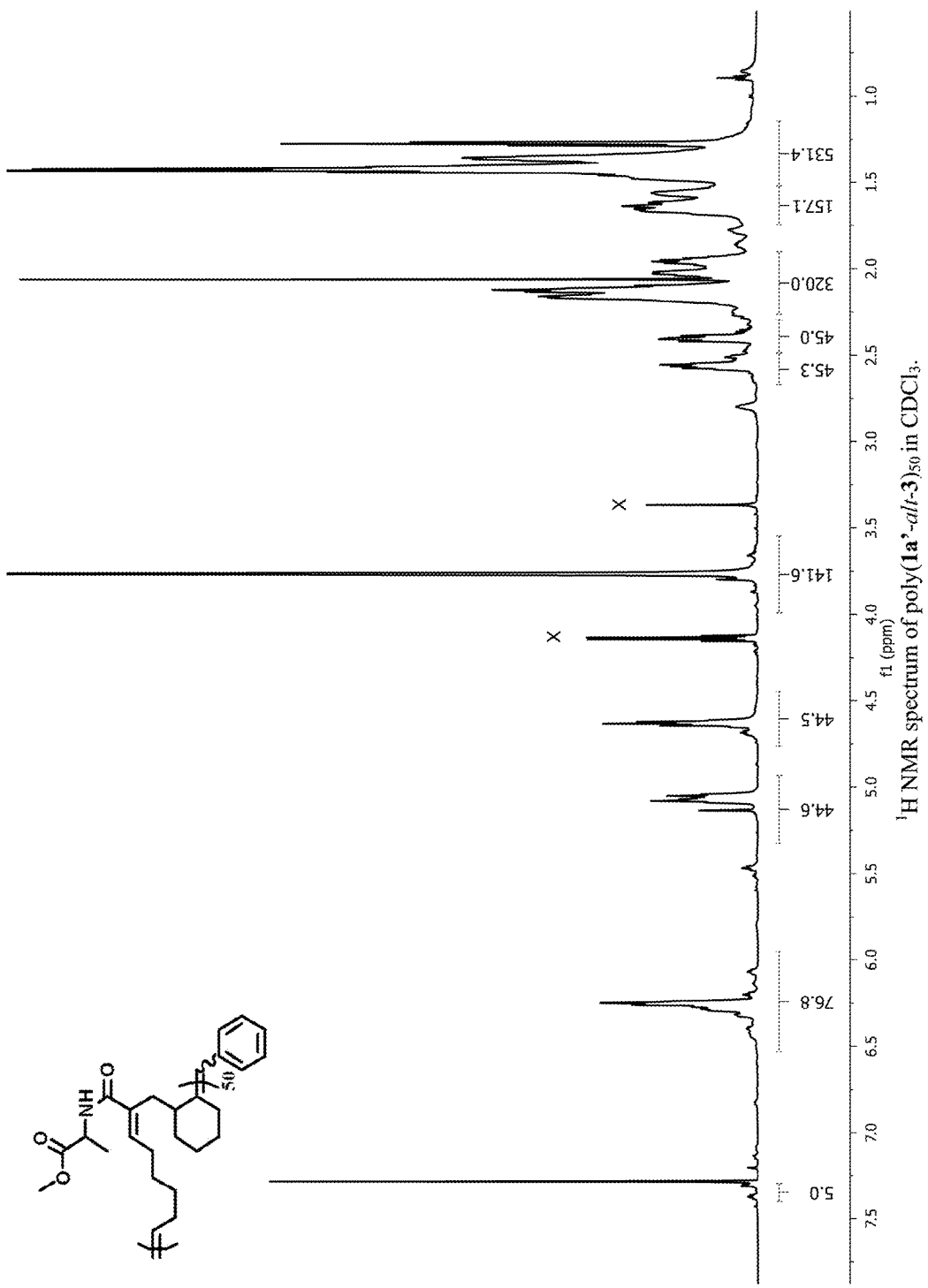
FIG. 48 shows the $^1$H NMR spectrum of poly(1a'-alt-3)$_{50}$ in CDCl$_3$.
Figure 49:
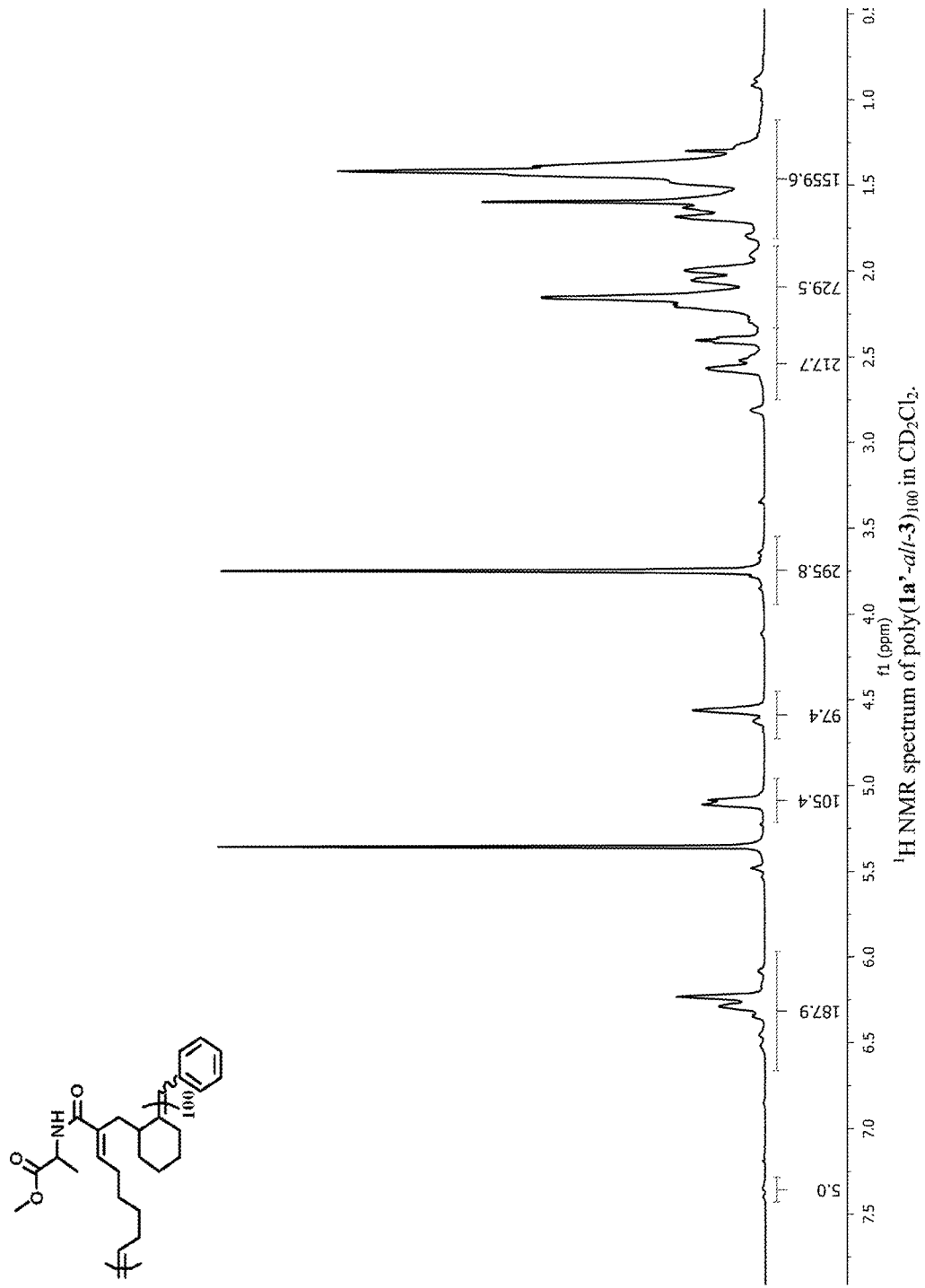
FIG. 49 shows the $^1$H NMR spectrum of poly(1a'-alt-3)$_{100}$ in CD$_2$Cl$_2$.
Figure 50:
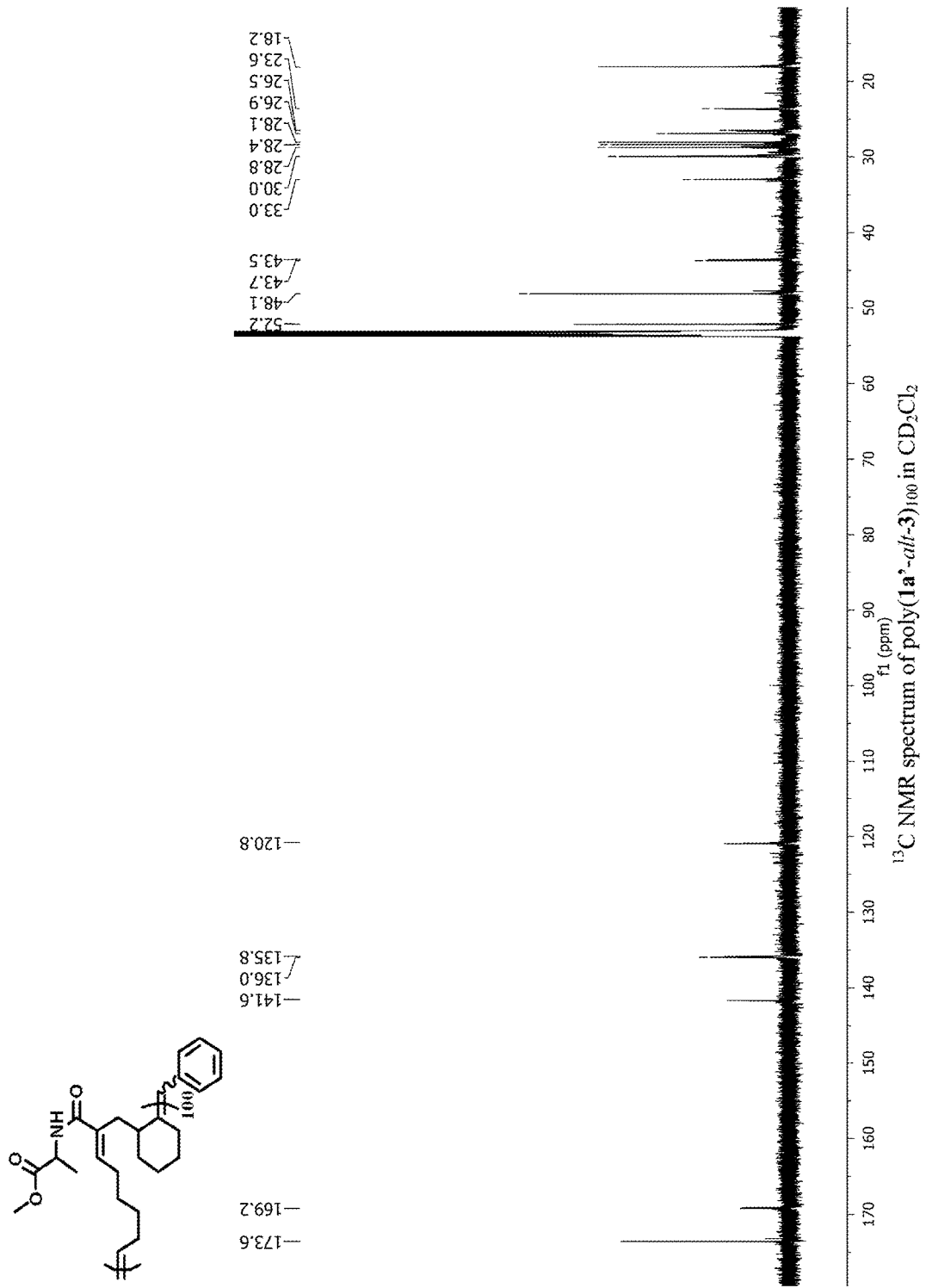
FIG. 50 shows the $^{13}$C NMR spectrum of poly(1a'-alt-3)$_{100}$ in CD$_2$Cl$_2$.
Figure 51:
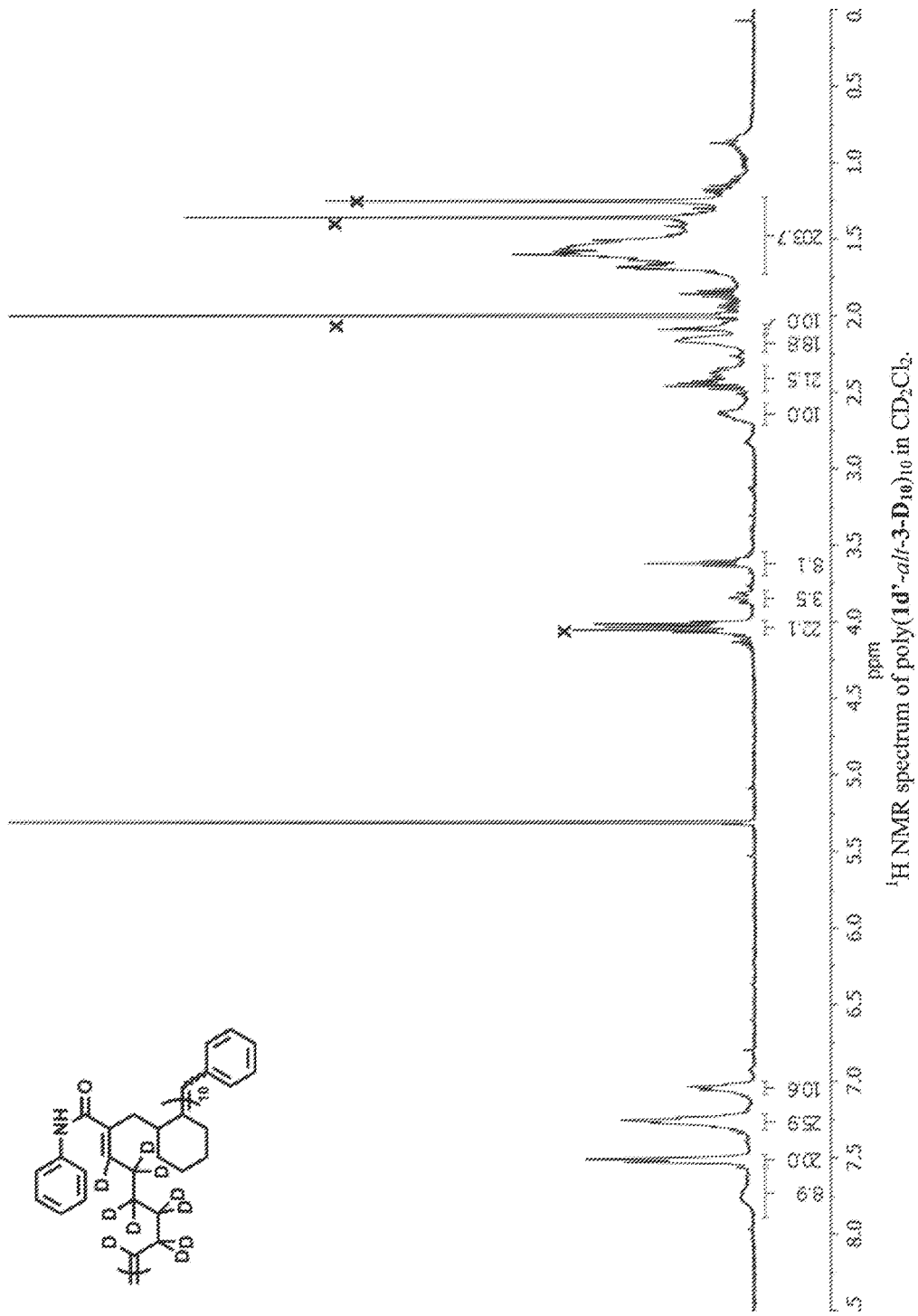
FIG. 51 shows the $^1$H NMR spectrum of poly(1d'-alt-3-D$_{10}$)$_{10}$ in CD$_2$Cl$_2$.
Figure 53:
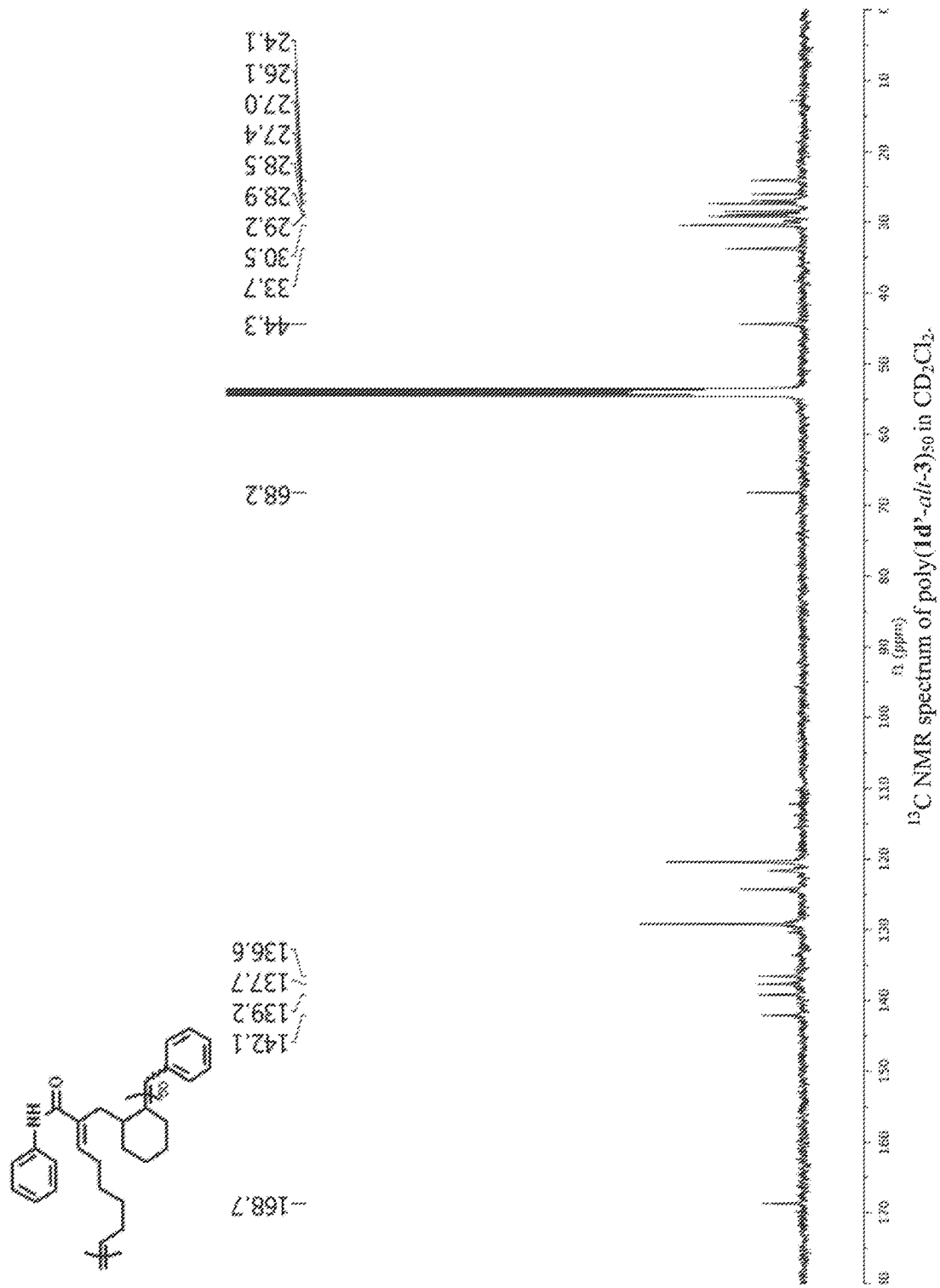
FIG. 53 shows the $^{13}$C NMR spectrum of poly(1d'-alt-3)$_{50}$ in CD$_2$Cl$_2$.
Figure 54:
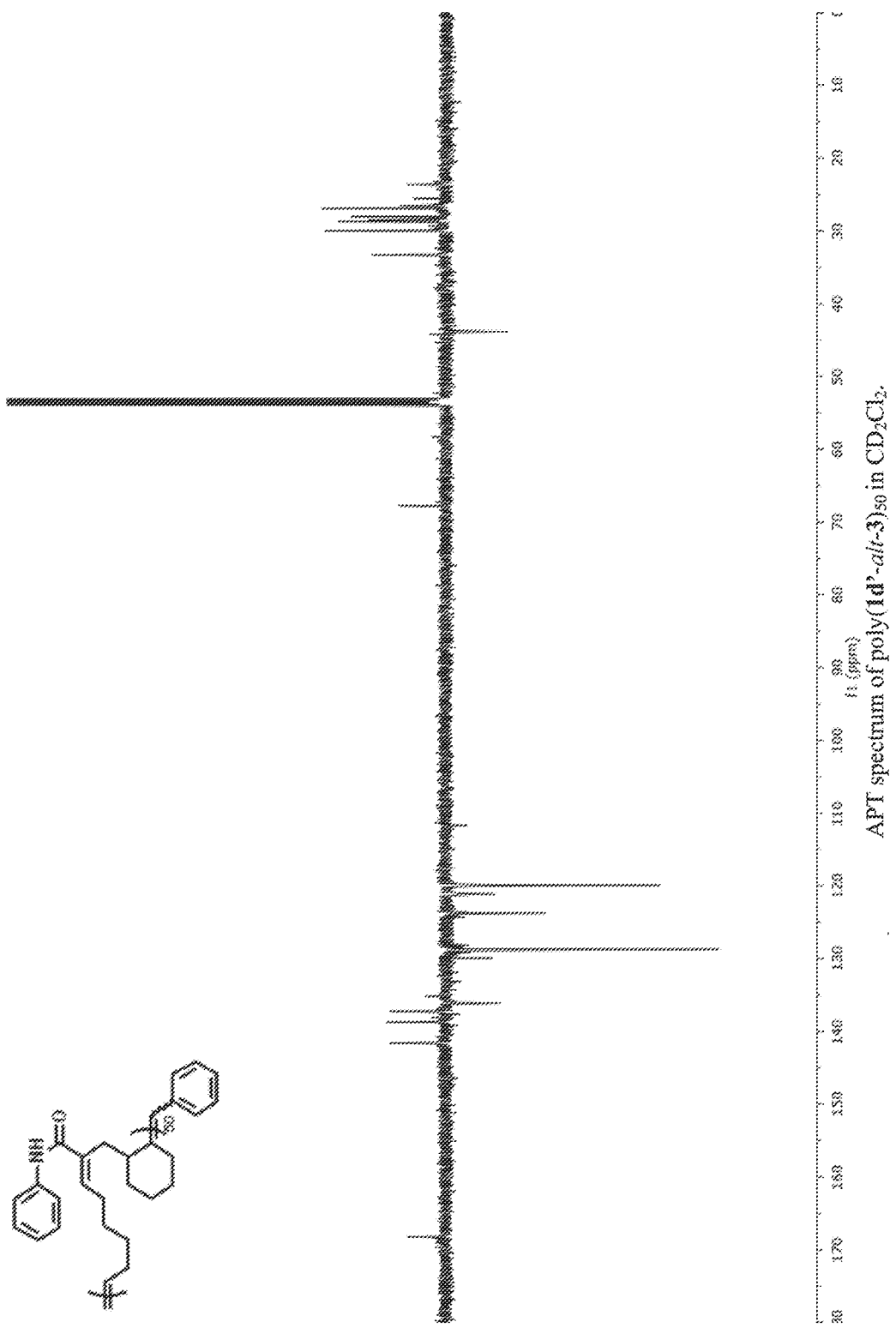
FIG. 54 shows the APT spectrum of poly(1d'-alt-3)$_{50}$ in CD$_2$Cl$_2$.
Figure 56:
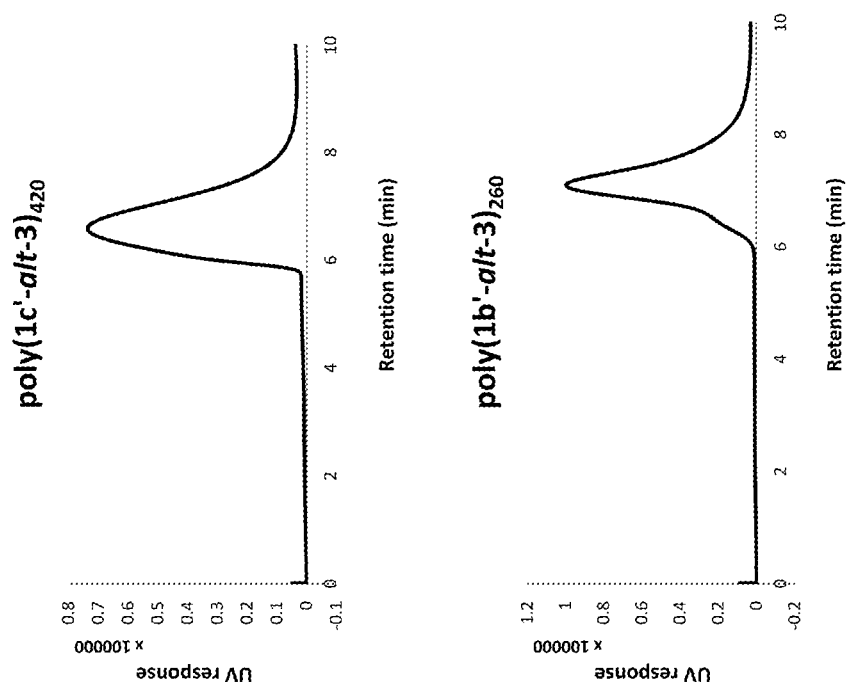
FIG. 56 shows the molar mass dispersity ($Ð_M$) traces of long linear isomerized amide AROMP polymers. Phenogel 5 µm 10E4A, LC column (300×7.8 mm, 500 KDa exclusion limit), Phenomenex, was used with a flow rate of 1.00 mL/min in THF at 30° C. Both polymers were prepared with isomerized and purified amides.

Integration of the poly(1'-alt-3)$_n$ alkene signals relative to side chain signals demonstrated that an equal incorporation of the two monomers had occurred. An AA or BB dyad would be formed upon backbiting. Additional alkene proton resonances in the 5 ppm region of the $^1$H NMR spectrum which would indicate formation of BB dyad were not observed. In the i-AROMP product, the AA dyad does not possess an alkene proton. Therefore, we inspected the $^{13}$C NMR spectra of poly(1d'-alt-3)$_{50}$ and poly(1c'-alt-3)$_{424}$ for the presence of AA dyad alkene resonances, specifically, a C3' resonance between 160-145 ppm, and found none (FIG. 6). Further evidence for the equal incorporation of monomers 1d' and 3 was obtained with experiments with cyclohexene-D$_{10}$. The $^1$H NMR spectra of the deuterium labeled copolymer poly(1d'-alt-3-D$_{10}$)$_{10}$ show a complete loss of the alkene resonances at 6.3 ppm and 5.1 ppm as expected for an alternating AB polymer (FIG. 7).

TABLE 2

Alternating copolymerization (AROMP) of bicyclic amides 1 or 1' and cyclohexenes 3 catalyzed by catalyst 2.[a]

| entry | A/B | [A]:[3]:[2] | [2] (M) | time (h) | % conv[b] | DP$_{[AB]}$[c] | M$_w^{GPC,d}$ (kDa) | M$_n^{GPC,d}$ (kDa) | D$_M$ | M$_n^{theor,e}$ (kDa) |
|---|---|---|---|---|---|---|---|---|---|---|
| 1 | 1c/3 | 10:20:1 | 0.01 | 1.5 | 100 | 10 | nd[f] | nd | nd | nd |
| 2 | 1c/3 | 50:100:1 | 0.002 | 2 | 100 | 50 | 17.0 | 9.4 | 1.8 | 14.5 |
| 3 | 1d/3 | 50:100:1 | 0.002 | 1 | 100 | [g] | 16.0 | 10.1 | 1.6 | 15.6 |
| 4[h] | 1a'/3 | 50:100:1 | 0.002 | 2 | 100 | 50 | 15.1 | 12.5 | 1.2 | 15.8 |
| 5[h] | 1a'/3 | 100:200:1 | 0.002 | 6 | 100 | 100 | 30.7 | 29.1 | 1.1 | 31.9 |
| 6[h] | 1b'/3 | 150:300:1 | 0.002 | 2.5 | 100 | 140 | 40.3 | 34.0 | 1.2 | 45.7 |
| 7[h] | 1b'/3 | 300:600:1 | 0.001 | 3.5 | 90 | 260 | 80.9 | 69.6 | 1.2 | 91.0 |
| 8[i] | 1c'/3 | 100:200:1 | 0.002 | 2 | 100 | 100 | 28.4 | 20.5 | 1.4 | 28.1 |
| 9[i] | 1c'/3 | 500:1000:1 | 0.0004 | 6 | 85 | 420 | 130.9 | 111.6 | 1.2 | 137.7 |

[a]All preparative polymerization experiments were performed three times. Representative molecular weight data are presented from a single polymerization.
[b]Conversion was determined by monitoring the disappearance of the amide resonance in 1 or 1'.
[c]Degree of polymerization (DP) was determined for the AB repeat by integration of polymer resonances relative to the styrene end group. We estimate the integration error to be within 5%.
[d]M$_w$-weight average molecular weight; M$_n$-number average molecular weight, determined by GPC.
[e]Theoretical M$_n$ calculated from the monomer:catalyst feed ratio.
[f]not determined.
[g]The DP could not be determined because of spectroscopic overlap and was estimated from the feed ratio of 1d and catalyst 2.
[h]isomerized amide was isolated and fresh 2 added before AROMP in CDCl$_3$.
[i]Isomerized amide was isolated and fresh 2 added before AROMP in CD$_2$Cl$_2$.

We explored the utility of alternating copolymerization by testing the maximal length of alternating copolymer that could be prepared. When cyclohexene 3 was added directly to a completed isomerization reaction of 1c' or 1d', poly(1c'-alt-3)50 or poly(1d'-alt-3)50 was obtained (Table 2). However, the dispersities exceeded those expected from the monomer:—catalyst ratio for a ruthenium-catalyzed polymerization, presumably because of loss of catalyst during isomerization. Therefore, in order to facilitate characterization of polymers longer than 100 AB dyads, to maximize their purity, and to minimize their dispersity, we isolated amides 1' before initiation of the AROMP reaction and added fresh catalyst.

In the case of amides 1a' and 1b', the AROMP reactions provided maximal lengths of 100 AB dyads and 260 AB dyads, respectively; with modest D$_M$=1.1-1.2. Higher monomer feed ratios did not provide longer copolymers. In contrast, when amide 1c' was mixed with catalyst 2 in a ratio of 500:1 with 1000 equivalents of cyclohexene 3, we reproducibly obtained alternating copolymer with more than 400 AB dyads (FIG. 5 7c) and a modest molecular weight distribution (D$_M$=1.2). Although the isomerization of 1d to 1d' was facile, the length of the copolymers obtained was limited to 50 AB dyads regardless of whether amide 1d' or 1d was used to initiate propagation. Finally, amides 1e' and 1f provided only short alternating copolymers that were not characterized further. Overall propagation efficiencies in order are 1c'>1b'>1a'>1d'>1e'>1f'. Thus, the maximal length of copolymer obtained depends on the degree of steric congestion α to the amide. Moreover, the presence of an aromatic ring in the amide substituent (1d' or 1e') significantly reduced propagation efficiency.

Given the unique polymer backbone generated in the i-AROMP reaction, the thermostability of poly(1c'-alt-3)$_n$ was evaluated by thermogravimetric analysis (TGA) and differential scanning calorimetry (DSC) in air. The T$_g$ of poly(1c'-alt-3)$_{97}$ is 86° C.±0.7° C. and it has a T$_{d10}$=130° C. (5 wt %). Decomposition of poly(1c'-alt-3)$_{424}$ occurred before the glass transition could be achieved. The high T$_g$ of poly(1c'-alt-3)$_{97}$ can be ascribed to its relatively rigid backbone, the large size of the amide substituents, and expected strength of the intermolecular interactions.

Conclusions.

Bicyclo[4.2.0]oct-7-ene-7-carboxamides of primary amines are quantitatively isomerized to bicyclo[4.2.0]oct-1(8)-ene-8-carboxamides in the presence of catalyst 2. Moreover, reaction of compound 1d to give 1d', which is complete within 15 minutes, is by far the fastest ruthenium-catalyzed olefin isomerization reported to date. This isomerization of an internal olefin in a bicyclic system provides a facile approach to synthesize tetra-substituted bicyclo[4.2.0]oct-1(8)-ene-8-carboxamides.

Remarkably, bicyclic tetra-substituted α, β-unsaturated amides are excellent AROMP substrates for the preparation of long, alternating copolymers. Isomerized unsaturated amides 1a', 1b', 1c' and 1d' undergo alternating ROMP with cyclohexene 1.5-4 times more rapidly than previously studied 1-cyclobutenecarboxylic acid esters or bicyclo[4.2.0]oct-7-ene-7-carboxylic esters. The isomerized amide AROMP reaction is compatible with a variety of amides that provide functional group handles. This facile sequence, isomerization followed by alternating ring-opening cross metathesis of A and ring-opening cross metathesis of B, provides an efficient entry to well-controlled architectures, enables the production of linear, soluble, and impressively long (greater than 100 and up to 400 AB units) alternating polymers with superior monomer economics, and unlocks the prospect of employing functionalized alternating and sequence-specific copolymers in multiple applications.

General Information

General Procedure for NMR Scale Isomerization Reactions. Under an N$_2$ atmosphere, a solution of the original amide and catalyst 2 was prepared in the indicated solvent (600 μL) in an NMR tube and NMR spectra were acquired at 35° C. At the end of the isomerization reaction (after complete consumption or no further isomerization of amide as judged by the change of the olefinic proton resonance), each reaction was terminated with ethyl vinyl ether (100 μL) and stirred for 30 min. The solvent was evaporated and the resulting residue was purified by silica chromatography to isolate the isomerized amide.

i-[4.2.0] Amide 1a'. Amide 1a (28 mg, 120 20 equiv) and catalyst 2 (5.3 mg, 6 μmol, 1 equiv) were mixed in CD$_2$Cl$_2$ in an NMR tube for 16 h; during this time, the integral for the olefinic proton decreased to 10% of its original value. The mixture was concentrated and the product was isolated by chromatography (100:1/CH$_2$Cl$_2$:MeOH) to yield 24 mg (80%) of 1a'. $^1$H NMR (500 MHz, CDCl$_3$): δ 5.99 (s, 1H, CONH), 4.68 (m, 1H, CH), 3.78 (s, 3H, OCH$_3$), 2.88 (dd, J=12.2, 6.7 Hz, 1H, CH$_2$), 2.73 (ddd, J=15.4, 7.6, 3.9 Hz, 1H, CH$_2$), 2.38 (m, 1H, CH), 2.24 (m, 1H, CH$_2$), 2.10 (m, 2H, CH$_2$), 1.94 (m, 1H, CH$_2$), 1.75 (m, 1H, CH$_2$), 1.45 (dt, J=18.6, 9.3 Hz, 3H, CH$_3$), 1.34 (m, 2H, CH$_2$), 1.16 (m, 1H, CH$_2$).

i-[4.2.0] Amide 1b'. Amide 1b (67 mg, 300 μmol, 50 equiv) and catalyst 2 (5.3 mg, 6 μmol, 1 equiv) were mixed in CD$_2$CL$_2$ in an NMR tube for 8 h. $^1$H NMR of the crude 1b' (500 MHz, CDCl$_3$): δ 5.98 (s, 0.9H, CONH), 4.11 (d, J=5.3 Hz, 2H, side chain CH$_2$), 3.78 (s, 3H, OCH$_3$), 2.87 (dd, J=13.4, 2.7 Hz, 1H, CH$_2$), 2.75 (dt, J=12.0, 3.8 Hz, 1H, CH$_2$), 2.37 (m, 1H, CH), 2.23 (m, 1H, CH$_2$), 2.10 (m, 2H, CH$_2$), 1.93 (m, 1H, CH$_2$), 1.75 (m, 1H, CH$_2$), 1.34 (m, 2H, CH$_2$), 1.12 (m, 1H, CH$_2$).

i-[4.2.0] Amide 1c'. Amide 1c (58 mg, 300 μmol, 50 equiv) and catalyst 2 (5.3 mg, 6 μmol, 1 equiv) were mixed in CD$_2$Cl$_2$ in an NMR tube for 1.5 h, when isomerization was complete. The mixture was concentrated and the product was isolated by chromatography (100:1/CH$_2$Cl$_2$:MeOH) to yield 49 mg (85%) of 1c'. $^1$H NMR (500 MHz, CDCl$_3$): δ 5.50 (s, 1H, CONH), 3.21 (m, 2H, side chain CH$_2$), 2.81 (dd, J=13.4, 2.7 Hz, 1 Hz, CH$_2$), 2.65 (dt, J=12.0, 3.8 Hz, 1H, CH$_2$), 2.31 (m, 1H, CH), 2.15 (m, 1H, CH$_2$), 2.04 (m, 2H, CH$_2$), 1.89 (m, 1H, CH$_2$), 1.69 (m, 2H, side chain CH$_2$), 1.51 (m, 2H, CH$_2$), 1.27 (m, 2H, CH$_2$), 0.91 (t, J=7.5 Hz, 3H, CH$_3$). $^{13}$C NMR (126 MHz, CD$_2$Cl$_2$): δ 164.1 (CONH), 161.7 (=C), 126.7 (=CCONH), 40.4 (side chain CH$_2$), 37.6 (CH), 33.9 (CH$_2$), 32.8 (CH$_2$), 27.1 (CH$_2$), 26.6 (CH$_2$), 24.5 (CH$_2$), 22.9 (side chain CH$_2$), 11.3 (CH$_3$). HRMS (ESI) calcd. for C$_{12}$H$_{19}$NO [M+H]$^+$194.1539, found 194.1535. λ$_{max}$ 224 nm was consistent with the λ$_{max}$ 223 nm previously reported for bicyclo[4,2,0]oct-1(8)-ene-8-carboxyamide. Fleming, Ian; Harley-Mason, John. *Journal of the Chemical Society* (1964), (June), 2165-74.

i-[4.2.0] Amide 1c' with MeOH. A 0.01 M fresh solution of catalyst 2 in 600 μL CD$_2$Cl$_2$ was divided into two NMR tubes, a 50 μL aliquot of MeOH (in large excess relative to catalyst 2) was added to one tube, and a 50 μL aliquot of CD$_2$Cl$_2$ was added to the second tube, both tubes were stirred for 2 h. Monomer 1c (10 equiv in 250 μL CD$_2$Cl$_2$) was added to each tube, and the kinetics of isomerization were monitored by $^1$H NMR spectroscopy.

i-[4.2.0] Amide 1d'. Amide 1d (23 mg, 120 μmol) and catalyst 2 (5.3 mg, 6 μmol) were mixed in CD$_2$Cl$_2$ in an NMR tube; after 20 min, isomerization was complete. The mixture was concentrated and the product was isolated by chromatography (100:1/CH$_2$Cl$_2$:MeOH) to yield 17.5 mg (78%) of 1d'. $^1$H NMR (500 MHz, CD$_2$Cl$_2$): δ 7.61 (d, J=7.8 Hz, 2H, Ph), 7.37 (t, J=7.6 Hz, 2H, Ph), 7.20 (s, 1H, CONH), 7.13 (t, J=7.4 Hz, 1H, Ph), 2.98 (dd, J=13.4, 2.7 Hz, 1Hz, CH$_2$), 2.84 (dt, J=12.0, 3.8 Hz, 1H, CH$_2$), 2.49 (m, 1H, CH$_2$), 2.35 (m, 1H, CH$_2$), 2.20 (m, 2H, CH$_2$), 2.00 (m, 1H, CH$_2$), 1.81 (m, 1H, CH$_2$), 1.44 (m, 2H, CH$_2$), 1.21 (m, 1H, CH$_2$).

i-[4.2.0] Amide 1e'. Amide 1e (68 mg, 300 μmol, 50 equiv) and catalyst 2 (5.3 mg, 6 μmol, 1 equiv) were mixed in CD$_2$Cl$_2$ in an NMR tube for 6 h when isomerization was complete. $^1$H NMR of the crude product 1e' (600 MHz, CD$_2$Cl$_2$): δ 7.20 7.02 (m, 4H, Ph), 5.64 (s, 1H, CONH), 3.3 (m, 2H, side chain CH$_2$), 2.85 (m, 1H, CH$_2$), 2.63 (m, 3H, ring CH$_2$ and side chain CH$_2$), 2.33 (m, 4H, ring CH and side chain CH$_2$), 2.13 (m, 2H, side chain CH$_2$), 2.03 (m, 1H, CH$_2$), 1.93 (m, 1H, CH$_2$), 1.84 (m, 2H, CH$_2$), 1.76 (m, 1H, CH$_2$), 1.32 (m, 2H, CH$_2$), 1.11 (m, 1H, CH$_2$).

i-[4.2.0] Amide 1e' Monitored with $^{13}$C NMR Spectroscopy. Amide 1e (19.2 mg, 67 μmol, 1 equiv) and catalyst 2 (60 mg, 67 μmol, 1 equiv) were mixed in CD$_2$Cl$_2$ in an NMR tube and the reaction was monitored with $^{13}$C NMR spectroscopy at 35° C.

i-[4.2.0] Amide 1e' with 3-bromopyridine. A 0.01 M solution of catalyst 2 in CD$_2$Cl$_2$ was divided into two NMR tubes, 3-bromopyridine (50 equiv) was added to one tube. Monomer 1e (10 equiv) was added to both aliquots ([2]$_{final}$=0.005 M), and the extent of isomerization was evaluated by $^1$H NMR spectroscopy over 14 h.

i-[4.2.0] Amide 1e' with Cl$_2$(H$_2$IMes)(PCy$_3$)Ru=CHPh. A 0.1 M solution of monomer 1e was divided into two NMR tubes. Catalyst Cl$_2$(H$_2$IMes)(PCy$_3$)Ru=CHPh in CD$_2$Cl$_2$ was added to one tube ([catalyst]$_{final}$=0.01 M, [1e']$_{final}$=0.05 M) and 2 in CD$_2$Cl$_2$ was added to the second tube ([2]$_{final}$=0.01 M), and the kinetics of isomerization were monitored by $^1$H NMR spectroscopy.

i-[4.2.0] Amide 1e' with 1,4-benzoquinone. A 0.01 M solution of catalyst 2 in CD$_2$Cl$_2$ was divided into two NMR tubes, 1,4-benzoquinone (5 equiv relative to 2) was added to one tube. Monomer 1e (10 equiv) was added to both tubes ([2]$_{final}$=0.005 M) and the extent of isomerization was evaluated by $^1$H NMR spectroscopy over 14 h.

i-[4.2.0] Amide 1f. Amide 1f or 1f* (16 mg, 60 µmol, 10 equiv) and catalyst 2 (5.3 mg, 6 µmol, 1 equiv) were mixed in CDCl$_3$ in an NMR tube for 24 h, at which point the integral for the olefinic proton had decreased to 30% or 10% of its original value, respectively. Partial $^1$H NMR spectroscopy of the crude 1f' (600 MHz, CD$_2$Cl$_2$): δ 6.69 (s, 0.1H, =CH), 6.31 (m, 0.1H, CONH), 6.09 (d, J=6.9 Hz, 0.9H, CONH). Partial $^1$H NMR of the crude 1f*' (600 MHz, CD$_2$Cl$_2$): δ 6.71 (s, 0.2H, =CH), 6.36 -6.26 (m, 0.3H, CONH), 6.11 (d, J=6.9 Hz, 0.7H, CONH). (Partial $^1$H NMR spectroscopic data are reported due to incomplete isomerization and significant upfield overlap of 1f/1f* with the new peaks from 1f'/1f*'.)

Attempted Isomerization of Amide 4. Amide 4 (27 mg, 120 µmol, 20 equiv) and catalyst 2 (5.3 mg, 6 µmol) were mixed in CD$_2$Cl$_2$ in an NMR tube for 18 h. Only a 2% of decrease in the intensity of the olefinic resonance of amide 4 was observed.

General Procedure for NMR Scale AROMP Reactions. All kinetic experiments were performed at least twice, and preparative polymerization experiments were performed three times. Under an N$_2$ atmosphere, a solution of amide 1 in CD$_2$Cl$_2$ (300 µL) was added to the NMR tube. Then 300 µL of catalyst 2 solution was added to the NMR tube. After complete mixing of the solution, NMR spectra were acquired at 35° C. Cyclohexene 3 was added after the amide was completely converted to its tetrasubstituted isomer as judged by the disappearance of the olefinic proton resonance around 6.7 ppm. This procedure was used for the preparation of polymers with up to 50 AB repeats. To ensure narrow dispersities, in the preparation of longer alternating polymers, the isomer 1' was isolated and mixed with fresh catalyst 2 in CD$_2$Cl$_2$. Cyclohexene 3 was added after catalyst 2 completely initiated as determined by the disappearance of the Ru alkylidene resonance at 19.1 ppm in the $^1$H NMR spectrum. When the propagation stopped or the isomerized amide disappeared as judged by a complete upfield shift of the amide N—H resonance from ~5.4 ppm to ~6 ppm, the reaction was quenched with ethyl vinyl ether and stirred for 30 min. The solvent was evaporated, and alternating copolymer was purified by step chromatography (100% CH$_2$Cl$_2$ to remove contaminants, then 20:1/CH$_2$Cl$_2$: MeOH to elute copolymer). The theoretical Mntheor was calculated from the monomer:catalyst feed ratio.

poly(1a'-alt-3)$_{50}$. Amide 1a' (14.2 mg, 60 µmol, 50 equiv), catalyst 2 (1.1 mg, 1.20 µmol, 1 equiv) and 3 (9.8 mg, 120 µmol, 100 equiv) were mixed in CDCl$_3$ in an NMR tube. After 2 h, amide 1a' was completely consumed. Flash column chromatography of the crude product yielded poly (1a'-alt-3)$_{50}$ (14.9 mg, 78% yield). $^1$H NMR (700 MHz, CDCl$_3$): δ 7.45-7.27 (m, 5H, Ph), 6.45-6.08 (m, 77H, =CH and CONH), 5.08 (m, 45H, =CH), 4.63 (m, 45H, CH), 3.77 (m, 142H, CH$_3$), 2.55 (m, 45H), 2.41 (m, 45H), 2.16-1.95 (m, 320H), 1.64-1.50 (m, 157H), 1.43-1.28 (m, 530H). M$_n^{theor}$=15 800. M$_n^{GPC}$=12 500. M$_w^{GPC}$=15 100. Đ$_M$=1.2.

poly(1a'-alt-3)$_{100}$. Amide 1a' (28.5 mg, 120 µmol, 100 equiv), catalyst 2 (1.1 mg, 1.20 µmol, 1 equiv) and 3 (19.6 mg, 240 µmol, 200 equiv) were mixed in CDCl$_3$ in an NMR tube. After 6 h, amide 1a' was completely consumed. Flash column chromatography of the crude product yielded poly (1a'-alt-3)$_{100}$ (26.8 mg, 70% yield). $^1$H NMR (700 MHz, CD$_2$Cl$_2$): δ 7.45-7.27 (m, 5H, Ph), 6.50-6.10 (m, 188H, =CH and CONH), 5.08 (m, 105H, =CH), 4.63 (m, 98H, CH), 3.77 (m, 296H, CH$_3$), 2.55 (m, 104H), 2.38 (m, 105H), 2.16-1.95 (m, 730H), 1.64-1.28 (m, 1560H). $^{13}$C NMR (126 MHz, CD$_2$Cl$_2$): δ 173.6, 169.2, 141.6, 136.0, 135.8, 120.8, 52.2, 48.1, 43.7, 43.5, 33.1, 30.0, 28.8, 28.4, 28.1, 26.9, 26.5, 23.6, 18.2. M$_n^{theor}$=31 900. M$_n^{GPC}$=29 100. M$_w^{GPC}$=30 700. Đ$_M$=1.1.

poly(1b'-alt-3)$_{140}$. Amide 1b' (40.2 mg, 180 µmol, 150 equiv), catalyst 2 (1.1 mg, 1.20 µmol, 1 equiv) and 3 (29.4 mg, 360 µmol, 300 equiv) were mixed in CDCl$_3$ in an NMR tube. After 2.5 h, amide 1b' was completely consumed. Flash column chromatography of the crude product yielded poly (1b'-alt-3)$_{140}$ (34.0 mg, 62% yield). $^1$H NMR (700 MHz, CD$_2$Cl$_2$): δ 7.45-7.27 (m, 5H, Ph), 6.64-6.42 (m, 133H, CONH), 6.27 (m, 141H, =CH), 5.10 (m, 146H, =CH), 4.02 (m, 370H, CH$_2$), 3.76 (m, 420H, CH$_3$), 2.58 (m, 160H), 2.41 (m, 118H), 2.23-2.01 (m, 1020H), 1.64-1.57 (m, 334H), 1.44-1.30 (m, 1288H). M$_n^{theor}$=45 700. M$_n^{GPC}$=34 000. M$_w^{GPC}$=40 300. Đ$_M$=1.2.

poly(1b'-alt-3)$_{260}$. Amide 1b' (40.2 mg, 180 µmol, 300 equiv), catalyst 2 (0.55 mg, 0.60 µmol, 1 equiv) and 3 (29.4 mg, 360 µmol, 600 equiv) were mixed in CDCl$_3$ in an NMR tube. After 3.5 h, 90% of amide 1b' was consumed. Flash column chromatography of the crude product yielded poly (1b'-alt-3)$_{260}$ (27.5 mg, 52% yield). $^1$H NMR (700 MHz, CD$_2$Cl$_2$): δ 7.45-7.27 (m, 5H, Ph), 6.63-6.41 (m, 242H, CONH), 6.27 (m, 256H, =CH), 5.10 (m, 267H, =CH), 4.02 (m, 510H, CH$_2$), 3.76 (m, 769H, CH$_3$), 2.58 (m, 284H), 2.41 (m, 206H), 2.23-2.01 (m, 2036H), 1.68-1.57 (m, 633H), 1.44-1.30 (m, 2358H). $^{13}$C NMR (126 MHz, CD$_2$Cl$_2$): δ 170.6, 169.7, 141.6, 136.3, 135.7, 121.0, 60.1, 52.1, 43.4, 41.2, 33.3, 30.0, 28.7, 28.3, 27.9, 26.8, 24.0, 20.6, 14.2. M$_n^{theor}$=91 000. M$_n^{GPC}$=69 600. M$_w^{GPC}$=80 900. Đ$_M$=1.2.

poly(1c'-alt-3)$_{10}$. Amide 1c (11.6 mg, 60 µmol, 10 equiv) and catalyst 2 (5.3 mg, 6 µmol, 1 equiv) were mixed. Upon completion of isomerization, 3 (9.8 mg, 120 µmol, 20 equiv) was added and after 1.5 h, amide 1c' was completely consumed. Flash column chromatography of the crude product yielded poly(1c'-alt-3)$_{10}$ (12 mg, 72% yield). $^1$H NMR (500 MHz, CD$_2$Cl$_2$): δ 7.45-7.21 (m, 5H, Ph), 6.40-5.57 (m, 20H, =CH and CONH), 5.09 (m, 10H, =CH), 3.31-3.16 (m, 26H, CH$_2$), 2.68-1.09 (m, 342H), 0.95 (t, J=7.4 Hz, 38H, CH$_3$).

poly(1c'-alt-3)$_{50}$. Amide 1c (11.6 mg, 60 µmol, 50 equiv) and catalyst 2 (1.1 mg, 1.20 µmol, 1 equiv) were mixed in CD$_2$Cl$_2$ in an NMR tube. Upon completion of isomerization, 3 (9.8 mg, 120 µmol, 100 equiv) was added and after 2 h, amide 1c' was completely consumed. Flash column chromatography of the crude product yielded poly(1c'-alt-3)$_{50}$ (14 mg, 74% yield). $^1$H NMR (500 MHz, CD$_2$Cl$_2$): δ 7.45-7.27 (m, 5H, Ph), 6.40-5.57 (m, 97H, =CH and CONH), 5.09 (m, 49H), 3.24 (m, 105H, CH$_2$), 2.58 (m, 46H), 2.39 (m, 44H), 2.29-1.90 (m, 363H), 1.80-1.17 (m, 700H), 1.04-0.87 (m, 160H, CH$_3$). M$_n^{theor}$=14 500. M$_n^{GPC}$=9 400. M$_w^{GPC}$=17 000. Đ$_M$=1.8.

poly(1c'-alt-3)$_{100}$. Amide 1c' (23.2 mg, 120 µmol, 100 equiv), catalyst 2 (1.1 mg, 1.20 µmol, 1 equiv) and 3 (19.6 mg, 240 µmol, 200 equiv) were mixed in CD$_2$Cl$_2$ in an NMR tube. After 2 h, amide 1c' was completely consumed. Flash column chromatography of the crude product yielded poly (1c'-alt-3)$_{100}$ (24 mg, 85% yield). $^1$H NMR (500 MHz, CD$_2$Cl$_2$): δ 7.45-7.27 (m, 5H, Ph), 6.40-5.57 (m, 186H, =CH and CONH), 5.09 (m, 98H, =CH), 3.24 (m, 199H, CH$_2$), 2.58 (m, 98H), 2.39 (m, 84H), 2.29-1.90 (m, 697H), 1.75-1.17 (m, 1259H), 1.04-0.87 (m, 311H). M$_n^{theor}$=28 100. M$_n^{GPC}$=20 500. M$_w^{GPC}$=28 400. Đ$_M$=1.4.

poly(1c'-alt-3)$_{420}$. Amide 1c' (23.2 mg, 120 µmol, 500 equiv), catalyst 2 (0.22 mg, 0.24 µmol, 1 equiv) and 3 (19.6 mg, 240 µmol, 1000 equiv) were mixed in CD$_2$Cl$_2$ in an NMR tube. After 6 h, amide 1c' was completely consumed. Flash column chromatography of the crude product yielded poly(1c'-alt-3)$_{420}$ (13 mg, 46% yield). $^1$H NMR (500 MHz, CD$_2$Cl$_2$): δ 7.36 (m, 5H, Ph), 6.44-5.65 (m, 741H, =CH and CONH), 5.22-4.99 (m, 424H, =CH), 3.33-3.13 (m, 871H, CH$_2$), 2.55 (m, 447H), 2.48-2.33 (m, 390H), 2.33-1.87 (m, 3115H), 1.80-1.15 (m, 6126H), 1.06-0.82 (m, 1522H). $^{13}$C NMR (126 MHz, CD$_2$Cl$_2$): δ 169.8, 141.8, 136.9, 134.4, 120.8, 43.7, 41.3, 33.1, 30.0, 30.0, 28.8, 28.3, 28.1, 26.9, 23.0, 11.3. M$_n^{theor}$=137 700. M$_n^{GPC}$=111 600. M$_w^{GPC}$=130 900. Đ$_M$=1.2.

poly(1d'-alt-3-D$_{10}$)$_{10}$. Amide 1d (13.7 mg, 60 µmol, 10 equiv) and catalyst 2 (5.3 mg, 6.0 µmol, 1 equiv) were mixed in CD$_2$Cl$_2$ in an NMR tube. Monomer 3-D$_{10}$ (9.8 mg, 120 µmol, 20 equiv) was added upon completion of isomerization. And after 1 h, amide 1d' was completely consumed. Flash column chromatography of the crude product yielded poly(1d'-alt-3-D$_{10}$)$_{10}$ (13 mg, 68% yield). $^1$H NMR (500 MHz, CD$_2$Cl$_2$): δ 7.89 (s, 10H, CONH), 7.59 (m, 20H, Ph), 7.38-7.26 (m, 20H, Ph), 7.10 (m, 10H, Ph), 3.67 (m, 10H), 2.63 (m, 10H), 2.4 (m, 20H), 2.15 (m, 20H), 2.08 (m, 10H), 1.67-1.23 (m, 203H).

poly(1d'-alt-3)$_{50}$. Amide 1d (13.7 mg, 60 µmol, 50 equiv) and catalyst 2 (1.1 mg, 1.20 µmol, 1 equiv) were mixed in CD$_2$Cl$_2$ in an NMR tube. Monomer 3 (9.8 mg, 120 µmol 100 equiv) was added upon completion of isomerization. And after 1 h, amide 1d' was completely consumed. Flash column chromatography of the crude product yielded poly(1d'-alt-3)$_{50}$ (14 mg, 76% yield). $^1$H NMR (500 MHz, CD$_2$Cl$_2$): δ 7.89 (s, 43H, CONH), 7.59 (m, 118H, Ph), 7.38-7.26 (m, 143H, Ph), 7.10 (m, 65H, Ph), 6.30 (m, 46H, =CH), 5.11 (m, 50H, =CH), 3.67 (m, 39H), 2.77 1.23 (m, 1359H). $^{13}$C NMR (126 MHz, CD$_2$Cl$_2$): δ 168.7, 142.1, 139.2, 137.7, 136.6, 68.2, 44.3, 33.7, 30.5, 29.2, 28.9, 28.5, 27.4, 27.0, 26.1, 24.1.M$_n^{theor}$=15 600. M$_n^{GPC}$=10 100. M$_w^{GPC}$=16 000. Đ$_M$=1.6.

General Procedures for the Synthesis of Bicyclo[n.2.0] Acids.

The methyl bicyclic cyclobutenecarboxylate, [n.2.0] ester was obtained according to the literature Snider B B, Rodini D J, Cionn R S E, & Sealfon S *J. Am. Chem. Soc.* 1979, 101:5283-5493; Tan L, Parker K A, & Sampson N S *Macromolecules* 2014, 47:6572-6579. Then [n.2.0] ester in THF was cooled in an ice bath, 2N KOH was added, and the solution was stirred for 30 min. The ice bath was removed and the reaction mixture was allowed to warm to 25° C. and stirred for another 4 h. THF was evaporated and the aqueous solution was acidified with 2N HCl to pH 2. The solution was extracted with CH$_2$Cl$_2$ (3×20 mL) and the combined CH$_2$Cl$_2$ solution was dried over anhydrous MgSO$_4$. The solvent was removed after filtration and the product was used without further purification.

[4.2.0] Acid 5. The methyl bicyclo[4.2.0]oct-7-ene-7-carboxylate (2.00 g, 12.0 mmol) in THF (5 mL) was hydrolyzed in the presence of 2N KOH (20 mL), and the product bicyclo[4.2.0]oct-7-ene-7-carboxylic acid 5 (1.74 g, 95%) was used without further purification.

[3.2.0] Acid 6. The methyl bicyclo[3.2.0]hepta-6-ene-6-carboxylate (500 mg, 3.29 mmol) was hydrolyzed by the procedure described above to yield acid 6 (350 mg, 80%). It was converted to the desired amide without further purification.

General Procedure for the Synthesis of Bicyclo[n.2.0]Alkene Amides.

Bicyclo[n.2.0]alkene carboxylic acid (n=3 or 4), ethyl, dimethylaminopropyl carbodiimide hydrochloride (EDC.HCl), and the desired amine were dissolved in dry CH$_2$Cl$_2$ in a 50-mL flask. The solution was cooled in an ice bath and DIPEA was added. The mixture was stirred for 8 h at 25° C. until the acid was consumed. The reaction mixture was washed sequentially with 5% NaHCO$_3$ (3×), 1N HCl (3×) and brine (2×) and dried over anhydrous MgSO$_4$. The solvent was filtered and removed by evaporation. The crude product was subjected to silica flash chromatography.

[4.2.0] Amide 1a. Acid 5 (100 mg, 0.66 mmol), L-Ala-OMe.HCl (104 mg, 0.72 mmol), EDC.HCl (139 mg, 0.72 mmol) and DIPEA (370 µL, 2.1 mmol) were allowed to react in 20 mL CH$_2$Cl$_2$ and subjected to work up as described. Chromatography (97:3/CH$_2$Cl$_2$:MeOH) yielded amide 1a as a mixture of diastereomers (146 mg, 80%). $^1$H NMR (600 MHz, CDCl$_3$): δ 6.70 (d, J=6.7 Hz, 1H, =CH), 6.19 (d, J=5.6 Hz, 1H, CONH), 4.61 (qd, J=7.2, 2.6 Hz, 1H, side chain CH), 3.71 (s, 3H, OCH$_3$), 3.05 (m, 1H, CH), 2.74 (m, 1H, CH), 1.79 (m, 1H, CH$_2$), 1.69 (m, 2H, CH$_2$), 1.52 (m, 3H, CH$_2$), 1.39 (m, 5H, CH$_2$ and CH$_3$). $^{13}$C NMR (126 MHz, CDCl$_3$): δ 173.5 (COOR), 162.1 (CONH), 145.2 (=CH), 144.1 (=CH), 52.4 (OCH$_3$), 47.5 (side chain CH), 39.3 (CH), 37.6 (CH), 23.8 (CH$_2$), 23.6 (CH$_2$), 18.7 (CH$_2$), 18.5 (CH$_2$), 18.2 (CH$_3$). Apparent peak doublets that arise from the presence of two diastereomers were reported as a single chemical shift. HRMS (ESI) calcd. for C$_{13}$H$_{19}$NO$_3$ [M+H]$^+$238.1438, found 238.1429.

[4.2.0] Amide 1b. Acid 5 (100 mg, 0.66 mmol), Gly-OMe.HCl (87 mg, 0.69 mmol), EDC.HCl (139 mg, 0.72 mmol) and DIPEA (570 µL, 3.3 mmol) were allowed to react in 20 mL CH$_2$Cl$_2$ and subjected to work up as described. Chromatography (97:3/CH$_2$Cl$_2$:MeOH) yielded amide 1b, (146 mg, 80%). $^1$H NMR (400 MHz, CDCl$_3$): δ 6.71 (s, 1H, =CH), 6.36 (s, 1H, CONH), 4.03 (m, 2H, side chain CH$_2$), 3.70 (s, 3H, OCH$_3$), 3.02 (dd, J=10.4, 5.3 Hz, 1H, CH), 2.74 (dd, J=9.7, 4.8 Hz, 1H, CH), 1.77 (m, 1H, CH$_2$), 1.67 (m, 2H, CH$_2$), 1.52 (m, 3H, CH$_2$), 1.37 (m, 2H, CH$_2$). $^{13}$C NMR (101 MHz, CDCl$_3$): δ 170.3 (COOR), 162.6 (CONH), 145.1 (=CH), 143.9 (=CH), 52.1 (OCH$_3$), 40.5 (side chain CH$_2$), 39.3 (CH), 37.6 (CH), 23.6 (CH$_2$), 23.5 (CH$_2$), 18.5 (CH$_2$), 18.1 (CH$_2$). HRMS (ESI) calcd. for C$_{12}$H$_{17}$NO$_3$ [M+H]$^+$ 224.1281, found 224.1273.

[4.2.0] Amide 1c. Acid 5 (300 mg, 2.0 mmol), propyl amine (130 mg, 2.2 mmol), EDC.HCl (421 mg, 2.2 mmol) and DIPEA (767 µL, 4.4 mmol) were allowed to react in 60 mL CH$_2$Cl$_2$ and subjected to work up as described. Chromatography (97:3/CH$_2$Cl$_2$:MeOH) yielded amide 1c, (307 mg, 80%). $^1$H NMR (400 MHz, CDCl$_3$): δ 6.69 (d, J=0.9 Hz, 1H, =CH), 5.77 (s, 1H, CONH), 3.25 (qd, J=13.3, 6.3 Hz, 2H, CH$_2$), 3.02 (dd, J=10.4, 5.6 Hz, 1H, CH), 2.76 (q, J=4.9 Hz, 1H, CH), 1.82 (m, 1H, CH$_2$), 1.70 (m, 2H, CH$_2$), 1.54 (m, 5H, side chain CH$_2$ and ring CH$_2$), 1.42 (m, 2H, CH$_2$), 0.91 (t, J=7.4 Hz, 3H, CH$_3$). $^{13}$C NMR (101 MHz, CDCl$_3$): δ 162.9 (CONH), 144.6 (=CH), 144.0 (=CH), 40.6 (side chain CH$_2$), 39.3 (CH), 37.4 (CH), 23.9 (CH$_2$), 23.7 (CH$_2$), 22.8 (side chain CH$_2$), 18.7 (CH$_2$), 18.2 (CH$_2$), 11.2(CH$_3$). HRMS (ESI) calcd. for C$_{12}$H$_{19}$NO [M+H]$^+$194.1539, found 194.1532.

[4.2.0] Amide 1d. Acid 5 (300 mg, 2.0 mmol), aniline (204 mg, 2.2 mmol), EDC.HCl (421 mg, 2.2 mmol) and DIPEA (767 µL, 4.4 mmol) were allowed to react in 60 mL $CH_2Cl_2$ and subjected to work up as described. Chromatography (98:2/$CH_2Cl_2$:MeOH) yielded amide 1d, (170 mg, 40%) free of the major impurity N-phenyl-8-(phenylamino)-bicyclo[4.2.0]octane-7-carboxamide. $^1$H NMR (500 MHz, $CDCl_3$): δ 7.58 (d, J=7.8 Hz, 2H, Ph), 7.36 (s, 1H, CONH), 7.31 (t, J=7.9 Hz, 2H, Ph), 7.10 (t, J=7.4 Hz, 1H, Ph), 6.83 (s, 1H, =CH), 3.15 (dd, J=10.5, 5.5 Hz, 1H, CH), 2.82 (q, J=5.1 Hz, 1H, CH), 1.89 (m, 1H), 1.78 (m, 2H), 1.60 (m, 3H), 1.46 (m, 2H). $^{13}$C NMR (126 MHz, $CDCl_3$): δ 160.6 (CONH), 145.4 (=CH), 145.0 (=CH), 137.6 (Ph), 129.0 (Ph), 129.0 (Ph), 124.2 (Ph), 124.2 (Ph), 119.6 (Ph), 39.6 (CH), 37.6 (CH), 24.0 ($CH_2$), 23.7 ($CH_2$), 18.8 ($CH_2$), 18.3 ($CH_2$). HRMS (ESI) calcd. for $C_{15}H_{17}NO$ [M+H]$^+$ 228.1383, found 228.1382.

[4.2.0] Amide 1e. Acid 5 (97 mg, 0.64 mmol), 3-p-tolyl-propan-1-amine (100 mg, 0.67 mmol), EDC.HCl (129 mg, 0.67 mmol) and DIPEA (226 μmol, 1.3 mmol) were allowed to react in 20 mL $CH_2Cl_2$ and subjected to work up as described. Chromatography (97:3/$CH_2Cl_2$:MeOH) yielded amide 1e, (147 mg, 85%). $^1$H NMR (600 MHz, $CDCl_3$): δ 7.17 6.97 (m, 4H, Ph), 6.65 (s, 1H, =CH), 5.66 (m, 1H, CONH), 3.35 (m, 2H, side chain $CH_2$), 2.97 (dd, J=10.5, 5.6 Hz, 1H, CH), 2.75 (q, J=5.1 Hz, 1H, CH), 2.62 (t, J=7.6 Hz, 2H, side chain $CH_2$), 2.30 (s, 3H, $CH_3$), 1.84 (m, 2H, side chain $CH_2$), 1.78 (m, 2H, $CH_2$), 1.65 (m, 1H, $CH_2$), 1.55 (m, 3H, $CH_2$), 1.42 (m, 2H, $CH_2$). $^{13}$C NMR (101 MHz, $CDCl_3$): δ 162.7 (CONH), 144.7 (=CH), 143.7 (=CH), 138.3 (Ph), 135.3 (Ph), 129.0 (Ph), 129.0 (Ph), 128.1 (Ph), 128.1 (Ph), 39.2 (side chain $CH_2$), 38.6 (CH), 37.4 (CH), 32.9 (side chain $CH_2$), 31.2 (side chain $CH_2$), 23.9 ($CH_2$), 23.7 ($CH_2$), 20.8 (side chain $CH_3$), 18.6 ($CH_2$), 18.2 ($CH_2$). HRMS (ESI) calcd. for $C_{19}H_{25}NO$ [M+H]$^+$284.2009, found 284.2005.

[4.2.0] Amide 1f. Acid 5 (200 mg, 2.0 mmol), (S)-2-phenylglycinol (400 mg, 2.2 mmol), EDC.HCl (281 mg, 2.2 mmol) and DIPEA (767 4.4 mmol) were allowed to react in 40 mL $CH_2Cl_2$ and subjected to work up as described. The crude product was developed on silica TLC plates with 20:1/$CH_2Cl_2$:MeOH and two partially separated spots were observed with R$_f$ values=0.32 and 0.25. Chromatography (97:3/$CH_2Cl_2$:MeOH) yielded two diastereomers: A (60 mg, 11%) and A* (50 mg, 9%). Each diastereomer (50 mg, 0.18 mmol) was mixed with acetic anhydride (20.7 mg, 0.203 mmol) and TEA (20.5 mg, 0.203 mmol) in anhydrous $CH_2Cl_2$, and the mixture was stirred for 16 h. After concentrating in vacuo, the reaction mixture was subjected to flash chromatography (97:3/$CH_2Cl_2$:MeOH) to yield amide if (41 mg, 62%) from the higher R$_f$ alcohol A. $^1$H NMR (500 MHz, $CDCl_3$): δ 7.42-7.23 (m, 5H, Ph), 6.75 (s, 1H, =CH), 6.20 (d, J=7.8 Hz, 1H, CONH), 5.35 (td, J=7.8, 5.0 Hz, 1H, CH), 4.50 (dd, J=11.5, 7.7 Hz, 1H, $CH_2O$), 4.26 (dd, J=11.5, 4.6 Hz, 1H, $OCH_2$), 3.06 (q, J=5.5 Hz, 1H, CH), 2.78 (q, J=4.9 Hz, 1H, CH), 2.04 (s, 3H, $CH_3$), 1.83 (m, 1H, $CH_2$), 1.76-1.68 (m, 2H, $CH_2$), 1.58 (m, 3H, $CH_2$), 1.44 (m, 2H, $CH_2$). $^{13}$C NMR (126 MHz, $CDCl_3$): δ 171.2 (COOR), 162.2 (CONH), 145.1 (=CH), 144.3 (=CH), 138.2 (Ph), 128.7 (Ph), 128.7 (Ph), 127.9 (Ph), 126.6 (Ph), 126.6 (Ph), 65.8 ($OCH_2$), 52.1 (side chain CH), 39.4 (CH), 37.6 (CH), 23.8 ($CH_2$), 23.7 ($CH_2$), 20.7 ($CH_3$), 18.7 ($CH_2$), 18.3 ($CH_2$). HRMS (ESI) calcd. for $C_{20}H_{25}NO_3$ [M+H]$^+$ 314.1751, found 314.1749. Amide 1f* (45 mg, 66%) was obtained from the lower R$_f$ alcohol A*. $^1$E NMR (500 MHz, $CDCl_3$): δ 7.42-7.23 (m, 5H, Ph), 6.76 (s, 1H, =CH), 6.27 (d, J=7.2 Hz, 1H, CONH), 5.35 (td, J=7.8, 4.6 Hz, 1H, CH), 4.54 (dd, J=11.5, 7.7 Hz, 1H, $CH_2O$), 4.27 (dd, J=11.5, 4.5 Hz, 1H, $OCH_2$), 3.07 (dd, J=10.5, 5.6 Hz, 1H, CH), 2.81 (dd, J=9.9, 4.9 Hz, 1H, CH), 2.03 (s, 3H, $CH_3$), 1.87 (m, 1H, $CH_2$), 1.75 (m, 2H, $CH_2$), 1.59 (m, 3H, $CH_2$), 1.46 (m, 2H, $CH_2$). $^{13}$C NMR (126 MHz, $CDCl_3$): δ 171.5 (COOR), 162.2 (CONH), 144.8 (=CH), 144.4 (=CH), 138.3 (Ph), 128.8 (Ph), 128.8 (Ph), 127.9 (Ph), 126.5 (Ph), 126.5 (Ph), 66.1 ($OCH_2$), 52.3 (side chain CH), 39.4 (CH), 37.7 (CH), 24.0 ($CH_2$), 23.7 ($CH_2$), 20.8 ($CH_3$), 18.7 ($CH_2$), 18.3 ($CH_2$). HRMS (ESI) calcd. for $C_{20}H_{25}NO_3$ [M+H]$^+$ 314.1751, found 314.1742.

[3.2.0] Amide 4. Acid 6 (138 mg, 1 mmol), L-Ala-OMe.HCl (157 mg, 1.1 mmol), EDC.HCl (210 mg, 1.1 mmol) and DIPEA (570 μL, 3.3 mmol) were allowed to react in 25 mL $CH_2Cl_2$ and subjected to work up as described. Chromatography (97:3/$CH_2Cl_2$:MeOH) yielded amide 4 as a mixture of diastereomers (157 mg, 75%). $^1$H NMR (600 MHz, $CDCl_3$): δ 6.49 (d, J=5.0 Hz, 1H, =CH), 6.21 (s, 1H, CONH), 4.64 (m, 1H, CH), 3.75 (s, 3H, $OCH_3$), 3.32 (s, 1H, CH), 3.02 (d, J=7.2 Hz, 1H, CH), 1.78-1.70 (m, 1H), 1.68-1.60 (m, 2H, $CH_2$), 1.57-1.54 (m, 1H, $CH_2$), 1.40 (d, J=7.1 Hz, 3H, $CH_3$), 1.30-1.23 (m, 2H, $CH_2$). $^{13}$C NMR (101 MHz, $CDCl_3$): δ 173.5 (COOR), 161.6 (CONH), 142.1 (=CH), 140.6 (=CH), 52.4 ($OCH_3$), 47.4 (side chain CH), 45.8 (CH), 43.9 (CH), 25.6 ($CH_2$), 25.4 ($CH_3$), 23.0 ($CH_2$), 23.1 ($CH_2$), 18.6 ($CH_2$), 18.6 ($CH_2$). Apparent peak doublets that arise from the presence of two diastereomers were reported as a single chemical shift. HRMS (ESI) calcd. for $C_{12}H_{17}NO_3$ [M+H]$^+$224.1281, found 224.1278.

1e Isomerization Monitored by $^{13}$C NMR Spectroscopy. Amide 1e (19.2 mg, 67 μmol, 1 equiv) and catalyst 2 (60 mg, 67 μmol, 1 equiv) were mixed in $CD_2Cl_2$ in an NMR tube and the reaction was monitored with $^{13}$C NMR spectroscopy at 35° C. (FIG. 4).

We claim:
1. A process for producing an alternating AB copolymer comprising the repeating unit I,

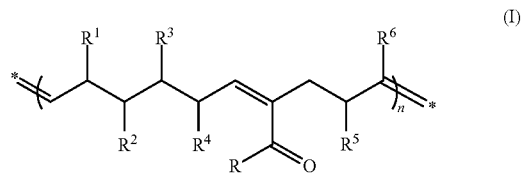

(I)

comprising:
(1) optionally isomerizing a cyclobutene of structure III in the presence of an olefin metathesis catalyst to form a cyclobutene III':

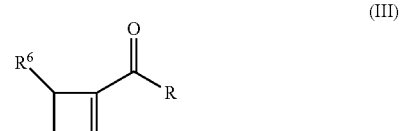

(III)

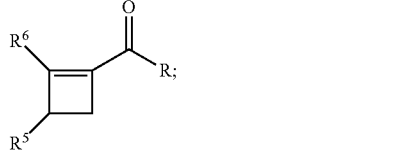

(III')

(2) polymerization of the cyclobutene III' with a cyclohexene II:

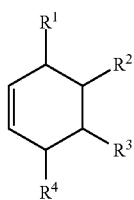
(II)

in the presence of an olefin metathesis catalyst;
wherein R is selected from the group consisting of H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, or arylamino and may be substituted with up to three substituents selected from halo, CN, $NO_2$, oxo, amino, alkyl, cycloalkyl, alkenyl, alkynyl, aralkyl, aryl, or a heterocyclic group;

n is between 2 and 500;

each substituent $R^1$ through $R^4$ is independently selected from the group consisting of H, aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, and halogen, and adjacent substitutions of $R^1$-$R^4$ may be taken together to form a 5- to 7-membered ring which may be substituted with up to three substituents selected from halo, CN, $NO_2$, oxo, amino, alkyl, cycloalkyl, alkenyl, alkynyl, aralkyl, aryl, or a heterocyclic group;

and wherein $R^5$ and $R^6$ are taken together to form a 5- or 6-membered ring, which may contain up to two heteroatoms in the ring selected from O or N, and which may be unsubstituted or substituted with up to four substituents selected from halo, CN, $NO_2$, oxo, amino, alkyl, cycloalkyl, alkenyl, alkynyl, aralkyl, aryl, or a heterocyclic group.

2. The process according to claim 1, wherein the alternating AB copolymer comprises the repeating unit Ia (Ia)

wherein X is O or NH; and
$R^a$ is selected from the group consisting of H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, or arylamino and may be substituted with up to three substituents selected from halo, CN, $NO_2$, oxo, amino, alkyl, cycloalkyl, alkenyl, alkynyl, aralkyl, aryl, or a heterocyclic group.

3. The process according to claim 1, wherein $R^5$ and $R^6$ are taken together to form a cyclohexyl ring, which may be substituted.

4. The process according to claim 1, wherein the alternating AB copolymer comprises the repeating unit Ib

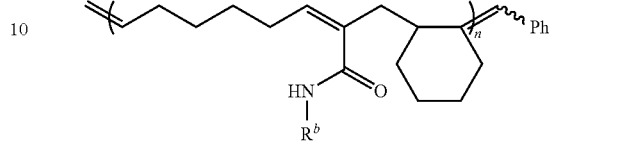
(Ib)

wherein
$R^b$ is selected from the group consisting of H, $C_1$-$C_{20}$ alkyl, $C_2$-$C_{20}$ alkenyl, $C_3$-$C_8$ cycloalkyl, heterocyclyl, aryl, aralkyl, $C_1$-$C_{20}$ alkoxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, or arylamino and may be substituted with up to three substituents selected from halo, CN, $NO_2$, oxo, amino, alkyl, cycloalkyl, alkenyl, alkynyl, aralkyl, aryl, or a heterocyclic group.

5. The process according to claim 1, wherein the cyclohexene has the structure IIa:

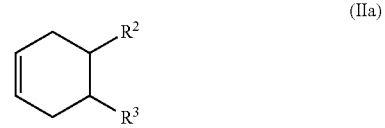
(IIa)

wherein each substituent $R^2$ and $R^3$ is independently selected from H, $C_1$-$C_{20}$ alkyl, $C_2$-$C_{20}$ alkenyl, $C_3$-$C_8$ cycloalkyl, heterocyclyl, aryl, $C_1$-$C_{20}$ alkoxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino or halogen, and may be substituted with up to three substituents selected from halo, CN, $NO_2$, oxo, amino, alkyl, cycloalkyl, alkenyl, alkynyl, aralkyl, aryl, and a heterocyclic group, and alternatively $R^2$ and $R^3$ are taken together to form a 5- to 7-membered ring which may be substituted with up to three substituents selected from halo, CN, $NO_2$, oxo, amino, alkyl, cycloalkyl, alkenyl, alkynyl, aralkyl, aryl, or a heterocyclic group.

6. The process according to claim 5, wherein the cyclohexene has the structure:

7. The process according to claim 1, wherein the cyclobutene has the structure IIIa or IIIa', in which the cyclobutene of structure IIIa is isomerized to a cyclobutene of structure IIIa'

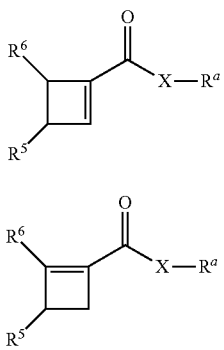
(IIIa)

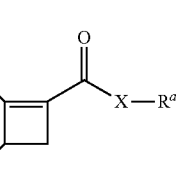
(IIIa')

in the presence of an olefin metathesis catalyst,
wherein X is selected from O, or NH, and
$R^a$ is selected from the group consisting of H, $C_1$-$C_{20}$ alkyl, $C_2$-$C_{20}$alkenyl, $C_3$-$C_8$ cycloalkyl, heterocyclyl, aryl, aralkyl, $C_1$-$C_{20}$ alkoxy, $C_2$-$C_{20}$alkenyloxy, $C_3$-$C_6$ cycloalkyloxy, aryloxy, heterocyclyloxy, $C_1$-$C_{20}$alkylamino, $C_2$-$C_{20}$ alkenylamino, $C_3$-$C_8$ cycloalkylamino, heterocyclylamino, or arylamino and may be substituted with up to three substituents selected from halo, CN, $NO_2$, oxo, alkyl, cycloalkyl, alkenyl, alkynyl, aralkyl, aryl, or a heterocyclic group.

8. The process according claim 1, wherein the cyclobutene has the structure IIIb or IIIb', in which the cyclobutene of structure IIIb is isomerized to a cyclobutene of structure IIIb'

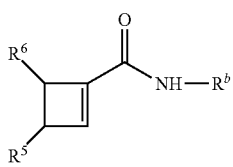
(IIIb)

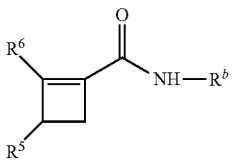
(IIIb')

in the presence of an olefin metathesis catalyst;
wherein $R^b$ is selected from the group consisting of H, $C_1$-$C_{20}$ alkyl, $C_2$-$C_{20}$alkenyl, $C_3$-$C_8$ cycloalkyl, heterocyclyl, aryl, aralkyl, $C_1$-$C_{20}$ alkoxy, $C_2$-$C_{20}$alkenyloxy, $C_3$-$C_6$ cycloalkyloxy, aryloxy, heterocyclyloxy, $C_1$-$C_{20}$ alkylamino, $C_2$-$C_{20}$alkenylamino, $C_3$-$C_8$cycloalkylamino, heterocyclylamino, or arylamino and may be substituted with up to three substituents selected from halo, CN, $NO_2$, oxo, amino, alkyl, cycloalkyl, alkenyl, alkynyl, aralkyl, aryl, or a heterocyclic group.

9. The process according to claim 1, wherein the cyclobutene has the structure IIIc or IIIc', in which the cyclobutene of structure IIIc is isomerized to a cyclobutene of structure IIIc'

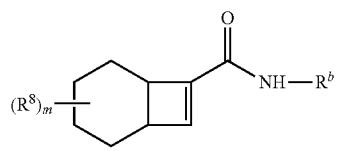
(IIIc)

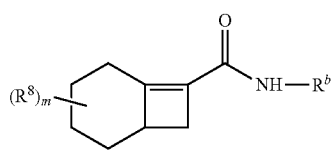
(IIIc')

in the presence of an olefin metathesis catalyst;
wherein $R^b$ is selected from the group consisting of H, $C_1$-$C_{20}$ alkyl, $C_2$-$C_{20}$alkenyl, $C_3$-$C_8$ cycloalkyl, heterocyclyl, aryl, aralkyl, $C_1$-$C_{20}$ alkoxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, or arylamino and may be substituted with up to three substituents selected from halo, CN, $NO_2$, oxo, amino, alkyl, cycloalkyl, alkenyl, alkynyl, aralkyl, aryl, or a heterocyclic group;

m is an integer from 0 to 4, and each $R^8$ is independently selected from the group consisting of aldehyde, $C_1$-$C_{20}$ alkyl, $C_2$-$C_{20}$ alkenyl, $C_3$-$C_6$ cycloalkyl, aryl, heterocyclyl, $C_1$-$C_{20}$ alkoxy, $C_1$-$C_{20}$ acyloxy, $C_2$-$C_{20}$ alkenyloxy, $C_3$-$C_6$ cycloalkyloxy, aryloxy, heterocyclyloxy, $C_1$-$C_{20}$ alkylamino, $C_2$-$C_{20}$ alkenylamino, $C_3$-$C_8$ cycloalkylamino, heterocyclylamino, arylamino, or halogen; and adjacent substitutions of $R^8$ may be taken together to form a 5- to 7-membered ring which may be substituted with up to three substituents selected from halo, CN, $NO_2$, oxo, amino, alkyl, cycloalkyl, alkenyl, alkynyl, aralkyl, aryl, or a heterocyclic group.

10. The process according to claim 9 wherein the cyclohexene is selected from formula IIa and the cyclobutene of structure IIIc is selected from IIIc 1, IIIc2, III3, IIIc4, IIIc5, and IIIc6:

(IIa)

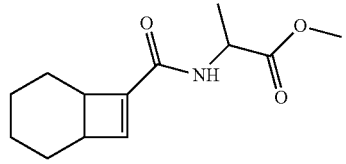
(IIIc1)

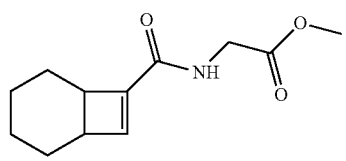
(IIIc2)

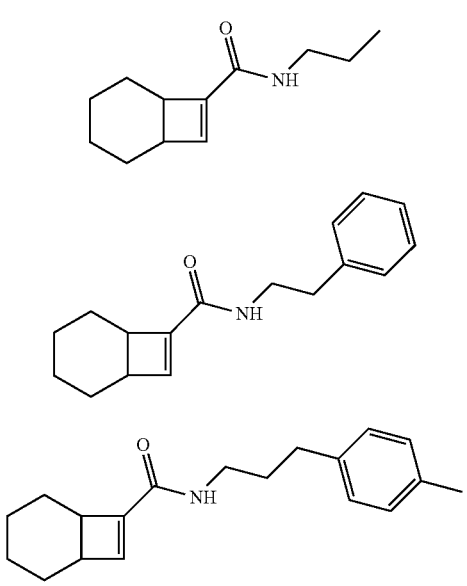

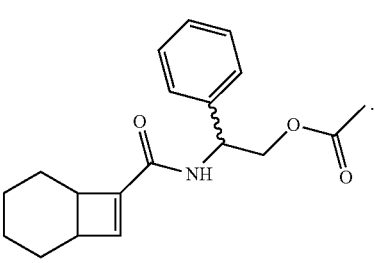

11. The process according to claim 7, wherein $R^5$ and $R^6$ are taken together to form a cyclohexyl ring, which may be optionally substituted.

12. The process according to claim 2, wherein $R^5$ and $R^6$ are taken together to form a cyclohexyl ring, which may be substituted.

13. The process according to claim 8, wherein $R^5$ and $R^6$ are taken together to form a cyclohexyl ring, which may be substituted.

* * * * *